United States Patent
Nagaki et al.

(10) Patent No.: US 9,902,665 B2
(45) Date of Patent: Feb. 27, 2018

(54) METHOD FOR PRODUCING HYDROCARBONS BY NON-OXIDATIVE COUPLING OF METHANE

(71) Applicant: Sabic Global Technologies, B.V., Bergen Op Zoom (NL)

(72) Inventors: Dick A. Nagaki, The Woodlands, TX (US); Zhun Zhao, Katy, TX (US); Myat Noe Zin Myint, Houston, TX (US); Istvan Lengyel, Lake Jackson, TX (US); Aghaddin Mamedov, Sugar Land, TX (US); C. William Gundlach, IV, Pearland, TX (US); Krishnan Sankaranarayanan, Sugar Land, TX (US); Derek Falcone, Houston, TX (US)

(73) Assignee: Sabic Global Technologies, B.V., Bergen Op Zoom (NL)

( * ) Notice: Subject to any disclaimer, the term of this patent is extended or adjusted under 35 U.S.C. 154(b) by 0 days.

(21) Appl. No.: 15/179,478

(22) Filed: Jun. 10, 2016

(65) Prior Publication Data

US 2016/0362351 A1    Dec. 15, 2016

Related U.S. Application Data

(60) Provisional application No. 62/175,005, filed on Jun. 12, 2015.

(51) Int. Cl.
  *C07C 2/76* (2006.01)
  *C07C 5/333* (2006.01)
  (Continued)

(52) U.S. Cl.
  CPC .............. *C07C 2/76* (2013.01); *B01J 21/08* (2013.01); *B01J 23/745* (2013.01);
  (Continued)

(58) Field of Classification Search
  CPC .................. C07C 2/76; C07C 5/32–5/3337
  See application file for complete search history.

(56) References Cited

U.S. PATENT DOCUMENTS

| | | | |
|---|---|---|---|
| 4,136,015 A | 1/1979 | Kamm et al. | |
| 4,423,022 A | 12/1983 | Albano et al. | |
| (Continued) | | | |

FOREIGN PATENT DOCUMENTS

| | | |
|---|---|---|
| EP | 2103586 A1 | 9/2009 |
| WO | 2015018807 A2 | 2/2015 |
| WO | 2015018815 A1 | 2/2015 |

OTHER PUBLICATIONS

Tavakoli, J. et al., "Pyrolysis of Methylene Chloride in Methane/Nitrogen Bath Using a Flow Reactor," Chem. Eng. Comm., 1993, pp. 135-150, vol. 119, Gordon and Breach Science Publishers S.A.
(Continued)

*Primary Examiner* — Sharon Pregler
*Assistant Examiner* — Alyssa L Cepluch
(74) *Attorney, Agent, or Firm* — Conley Rose, P.C.; Rodney B. Carroll

(57) ABSTRACT

A method for producing $C_{2+}$ hydrocarbons and $H_2$ comprising (a) introducing to a reactor a reactant mixture comprising methane, (b) heating the reactant mixture to a preheating temperature to yield a heated mixture, (c) generating free radicals in the heated mixture to form a primary effluent mixture comprising free radicals, $C_{2+}$ hydrocarbons, $H_2$, and unreacted methane, (d) reacting the primary effluent mixture in a secondary reaction zone to form a secondary effluent mixture comprising $C_{2+}$ hydrocarbons, $H_2$, free radicals, and unreacted methane, at a secondary reaction zone temperature that is greater than the preheating temperature, wherein a free radicals amount in the primary effluent mixture is greater than a free radicals amount in the secondary effluent mixture, (e) cooling the secondary effluent mixture to a
(Continued)

Reactor for Non-Oxidative Coupling of Methane quench temperature lower than the secondary reaction zone temperature to yield a product mixture comprising $C_{2+}$ hydrocarbons and $H_2$, and (f) recovering the product mixture.

18 Claims, 18 Drawing Sheets

(51) Int. Cl.
   *B01J 21/08* (2006.01)
   *B01J 23/745* (2006.01)
(52) U.S. Cl.
   CPC ........ *C07C 5/3332* (2013.01); *C07C 2521/08* (2013.01); *C07C 2523/745* (2013.01); *Y02P 20/52* (2015.11); *Y02P 20/582* (2015.11)

(56) References Cited

U.S. PATENT DOCUMENTS

| | | | |
|---|---|---|---|
| 4,724,272 A | 2/1988 | Raniere et al. | |
| 4,814,534 A | 3/1989 | Devries et al. | |
| 5,365,005 A * | 11/1994 | Weill | B01J 12/005 585/415 |
| 7,019,184 B2 | 3/2006 | Allison et al. | |
| 7,022,888 B2 | 4/2006 | Choudhary et al. | |
| 7,183,451 B2 | 2/2007 | Gattis et al. | |
| 8,013,196 B2 | 9/2011 | Mamedov et al. | |
| 2005/0045467 A1 | 3/2005 | Gondal et al. | |
| 2010/0028735 A1 | 2/2010 | Basset et al. | |
| 2010/0191031 A1 | 7/2010 | Sundaram | |
| 2012/0203045 A1* | 8/2012 | Coelho Tsou | B01J 29/06 585/412 |
| 2014/0056766 A1 | 2/2014 | Bedard et al. | |
| 2014/0056767 A1 | 2/2014 | Bedard et al. | |
| 2014/0336432 A1 | 11/2014 | Bao et al. | |

OTHER PUBLICATIONS

Antes, J., et al., "Chemistry and kinetics of chemical vapour deposition of pyrocarbon VII. Confirmation of the influence of the substrate surface area/reactor volume ratio," Carbon, 1999, pp. 2031-2039, vol. 37, Elsevier Science Ltd.
Chang, Shih-Hsin, et al., "Kinetic Parameters for Coupled Bulk and Wall Reactions in a Tubular Flow Reactor," AIChE Journal, Jul. 1987, pp. 1207-1211, vol. 33, No. 7.
Childers, David J., et al., "Modifying structure-sensitive reactions by addition of Zn to Pd," Journal of Catalysis, 2014, pp. 75-84, vol. 318, Elsevier Inc.
Dong, G.L., et al, "Consideration of reaction mechanisms leading to pyrolytic carbon of different textures," Carbon, 2002, pp. 2515-2528, vol. 40, Pergamon, Elsevier Science Ltd.
Guéret, Christophe, et al., "Methane pyrolysis: thermodynamics," Chemical Engineering Science, 1997, pp. 815-827, vol. 52, No. 5, Pergamon, Elsevier Science, Ltd.
Guo, Xiaoguang, et al., "Direct, Nonoxidative Conversion of Methane to Ethylene, Aromatics, and Hydrogen," Science, May 9, 2014, pp. 616-619, vol. 344, and supplementary material, 50 pages, www.sciencemag.org.
Holmen, A., et al., "High-Temperature Pyrolysis of Hydrocarbons. 1. Methane to Acetylene," Ind. Eng. Chem., Process Des. Dev., 1976, pp. 439-444, vol. 15, No. 3.
Holmen, A., et al., "High-Temperature Pyrolysis of Hydrocarbons. 2. Naphtha to Acetylene," Ind. Eng. Chem., Process Des. Dev., 1979, pp. 653-657, vol. 18, No. 4, American Chemical Society.
Holmen, Anders, et al., "Pyrolysis of natural gas: chemistry and process concepts," Fuel Processing Technology, 1995, pp. 249-267, vol. 42, Elsevier Science, B.V.
Hu, Zijun, et al., "Chemistry and kinetics of chemical vapour deposition of pyrocarbon VIII. Carbon deposition from methane at low pressures," Carbon, 2001, pp. 433-441, vol. 39, Pergamon, Elsevier Science, Ltd.

Hu, Z. J., "Influence of the surface area/volume ratio on the chemistry of carbon deposition from methane," Carbon, 2003, pp. 1501-1508, vol. 41, Pergamon, Elsevier Science, Ltd.
Lee, Woo Jin, et al, "Opposite effects of gas flow rate on the rate of formation of carbon during the pyrolysis of ethane and acetylene on a nickel mesh catalyst," Carbon, 2008, pp. 1208-1217, vol. 46, Elsevier Ltd.
Mears, Daivd E., et al., "On the Relative Importance of Intraparticle and Interphase Transport Effects in Gas-Solid Catalysis," Journal of Catalysis, 1973, pp. 283-287, vol. 30, Academic Press Inc.
Olsvik, Ola, et al., "Pyrolysis of Methane in the Presence of Hydrogen," Chem. Eng. Technol., 1995, pp. 349-358, vol. 18, VCH Verlagsgesellschaft mbH.
Olsvik, Ola, et al., "Thermal coupling of methane. A comparison between kinetic model data and experimental data," 1993, 16 pages, Elsevier Science B.V., Amsterdam.
Quah, Eugene B.H., et al., "Effects of radical desorption on catalyst activity and coke formation during the catalytic pyrolysis and oxidation of light alkanes," Applied Catalysis A: General, 2003, pp. 83-94, vol. 250, Elsevier Science, B.V.
Quah, Eugene B.H., et al., "Interinfluence between Reactions on the Catalyst Surface and Reactions in the Gas Phase during the Catalytic Oxidation of Methane with Air," Journal of Catalysis, 2001, pp. 315-323, vol. 197, Academic Press.
Xu, Yuebing, et al., "Performance of a binder-free, spherical-shaped Mo/HZSM-5 catalyst in the non-oxidative CH4 dehydroaromatization in fixed- and fluidized-bed reactors under periodic CH4-H2 switch operation," Chemical Engineering and Processing: Process Intensification, 2013, pp. 90-102, vol. 72, Elsevier B.V.
Trimm, D. L., "Coke formation and minimisation during steam reforming reactions," Catalysis Today, 1997, pp. 233-238, vol. 37, Elsevier Science, B.V.
Van Der Zwet, G.P., et al., "Pyrolysis of Methane and the Role of Surface Area," Catalysis Today, 1989, pp. 365-369, vol. 4, Elsevier Science Publishers B.V., Amsterdam.
Zhang, W.G., et al., "Chemical vapor deposition of carbon from methane at various pressures, partial pressures and substrate surface area/reactor volume ratios," Journal of Materials Science, 2001, pp. 3503-3510, vol. 36, Kluwer Academic Publishers.
Foreign communication from a related counterpart application International Application No. PCT/US2016/036932, International Search Report and Written Opinion, dated Sep. 8, 2016, 14 pages.
Billaud, Francis G., et al., "Thermal coupling of methane in a tubular flow reactor: parametric study," Ind. Eng. Chem. Res., 1993, pp. 1549-1554, No. 32, American Chemical Society.
Filing Receipt and Specification of U.S. Appl. No. 62/175,005, filed Jun. 12, 2015, entitled, "Method for Producing Hydrocarbons by Non-Oxidative Coupling of Methane," 112 pages.
Hüttinger, Klaus J., "CVD in Hot Wall Reactors—The Interaction Between Homogeneous Gas-Phase and Heterogeneous Surface Reactions," Chemical Vapor Disposition, 1998, pp. 151-158, vol. 4, No. 4, Wiley-VCH Verlag GmbH.
Filing Receipt and Specification of International Application No. PCT/US2016/036932, filed on Jun. 10, 2016, entitled, "A Method for Producing Hydrocarbons by Non-Oxidative Coupling of Methane," 128 pages.
Dean, A. M., "Detailed Kinetic Modeling of Autocatalysis in Methane Pyrolysis," J. Phys. Chem., 1990, pp. 1432-1439, vol. 94, American Chemical Society.
Gannon, Richard E., et al., "Encyclopedia of Chemical Technology," Kirk-Othmer, Apr. 18, 2003, John Wiley & Sons, Inc., 1 page of cover and publishing information.
Bartholomé, E., "The BASF-process for production of acetylene by partial oxidation of gaseous hydrocarbons," Special Supplement to Chemical Engineering Science, 1954, pp. 94-104, vol. 3.
Cook, Bruce, et al., "Conversion of methane to aromatics over Mo2C/ZSM-5 catalyst in different reactor types," Applied Catalysis A: General, 2009, pp. 34-41, vol. 365, Elsevier, B.V.
Dautzenberg, F.M., et al, "Catalyst and Reactor Requirements for the Oxidative Coupling of Methane," Catalysis Today, 1992, pp. 503-509, vol. 13, Elsevier Science Publishers, B.V.

(56) References Cited

OTHER PUBLICATIONS

Deutschmann, Olaf, et al., "Modeling the Partial Oxidation of Methane in a Short-Contact-Time Reactor," AIChE Journal, Nov. 1998, pp. 2465-2477, vol. 44, No. 11.

Deutschmann, Olaf, et al., "Natural Gas Conversion in Monolithic Catalysts: Interaction of Chemical Reactions and Transport Phenomena," Studies in Surface Science and Catalysis, 2001, pp. 251-258, Elsevier Science, B.V.

Gimeno, María Pilar, et al., "Counteracting Catalyst Deactivation in Methane Aromatization with a Two Zone Fluidized Bed Reactor," Ind. Eng. Chem. Res., 2010, pp. 996-1000, vol. 49, No. 3, American Chemical Society.

Choudhary, Tushar V., et al., "Nonoxidative Activation of Methane," Catalysis Reviews, 2003, pp. 151-203, vol. 45, No. 1, Marcel Dekker, Inc, New York, NY, USA.

Hoebink, J. H. B. J., et al., "Fixed Bed Reactor Design for Gas Phase Chain Reactions Catalysed by Solids: The Oxidative Coupling of Methane," Chemical Engineering Science, 1994, pp. 5453-5463, vol. 49, No. 24B, Elsevier Science Ltd.

Huang, Jian, et al., "Partial Oxidation of Methane to Methanol through Microwave Plasmas. Reactor Design to Control Free-Radical Reactions," J. Phys. Chem., 1994, pp. 206-210, vol. 98, No. 1, American Chemical Society.

Krummenacher, Jakob J., et al., "High yields of olefins and hydrogen from decane in short contact time reactors: rhodium versus platinum," Journal of Catalysis, 2004, pp. 429-438, vol. 222, Elsevier Inc.

Li, Lin, et al., "Reaction-transport simulations of non-oxidative methane conversion with continuous hydrogen removal-homogeneous-heterogeneous reaction pathways," Chemical Engineering Science, 2001, pp. 1869-1881, vol. 56, Elsevier Science Ltd.

Liu, S.Y., et al., "Nonoxidative Conversion of Methane in Dielectric Barrier Discharge Reactor: Prediction of Reaction Performance Based on Neural Network Model," The Journal of Physical Chemistry, 2014, pp. 10686-10693, vol. 118, American Chemical Society.

Ma, Shuqi, et al., "Recent progress in methane dehydroaromatization: From laboratory curiosities to promising technology," Journal of Energy Chemistry, 2013, pp. 1-20, vol. 22, No. 1, Dalian Institute of Chemical Physics, Chinese Academy of Sciences.

Mleczko, L., et al., "Catalytic oxidative coupling of methane—reaction engineering aspects and process schemes," Fuel Processing Technology, 1995, pp. 217-248, vol. 42, Elsevier Science, B.V.

Schmidt, Lanny D., "Modeling Millisecond Reactors," Studies in Surface Science and Catalysis, 2001, pp. 1-12, Elsevier Science, B.V.

Su, Yee San, et al., "Upper bound on the yield for oxidative coupling of methane," Journal of Catalysis, 2003, pp. 321-333, vol. 218, Elsevier, Inc.

Trioinfetti, Cristiano, et al., "Alkane Activation at Ambient Temperatures: Unusual Selectivities, C—C, C—H Bond Scission versus C—C Bond Coupling," ChemPhysChem Communications, 2008, pp. 533-537, vol. 9, Wiley-VCH Verlag GmbH & Co. KGaA, Weinheim.

Wang, Linsheng, et al., "Dehydrogenation and aromatization of methane under non-oxidizing conditions," Catalysis Letters, 1993, pp. 35-41, vol. 21, J.C. Baltzer AG, Science Publishers.

\* cited by examiner

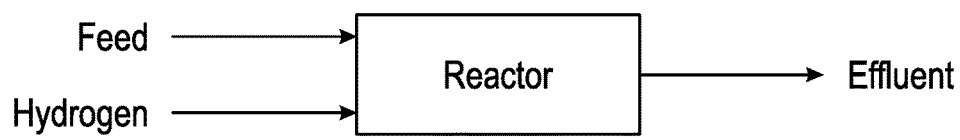
FIG. 1A
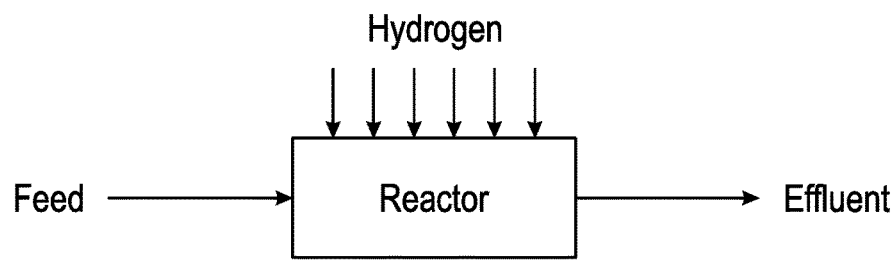
FIG. 1B
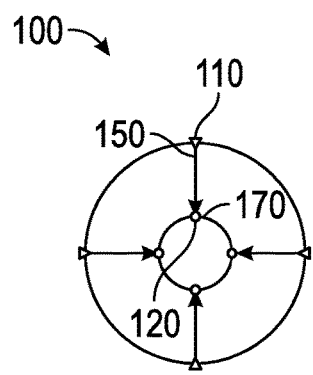
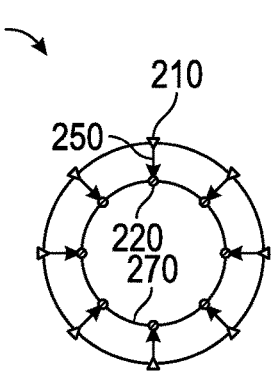
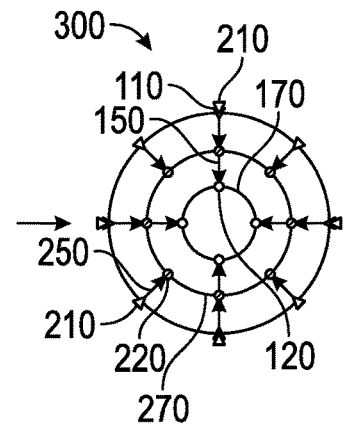
FIG. 2A   FIG. 2B   FIG. 2C

Reactor for Non-Oxidative Coupling of Methane

Modular Reactor with Microchannel Technology

METHOD FOR PRODUCING HYDROCARBONS BY NON-OXIDATIVE COUPLING OF METHANE

CROSS-REFERENCE TO RELATED APPLICATIONS

The present application is a non-provisional of and claims priority to U.S. Provisional Patent Application No. 62/175,005 filed Jun. 12, 2015 and entitled "Method for Producing Hydrocarbons by Non-Oxidative Coupling of Methane," which application is incorporated by reference herein in its entirety.

TECHNICAL FIELD

The present disclosure relates to methods of producing hydrocarbons, more specifically methods of producing $C_{2+}$ hydrocarbons by non-oxidative coupling of methane.

BACKGROUND

Hydrocarbons, and specifically $C_{2+}$ hydrocarbons such as ethylene and aromatic hydrocarbons (e.g., benzene), can be typically used to produce a wide range of products, for example, polymers, plastics, resins, break-resistant containers, packaging materials, adhesives, rubbers, lubricants, dyes, detergents, drugs, explosives, pesticides, etc. Currently, for industrial scale applications, ethylene is produced by heating natural gas condensates and petroleum distillates, which include ethane and higher hydrocarbons, and the produced ethylene is separated from a product mixture by using gas separation processes. Benzene can be produced by a variety of processes, such as for example catalytic reforming, steam cracking, toluene hydrodealkylation, and toluene disproportionation.

Natural gas is an excellent clean energy resource, of which the primary component is methane ($CH_4$). With an abundant supply of natural gas due to an explosive growth in shale gas and innovative drilling procedures (such as horizontal drilling and fracking), a lot of work has been directed towards direct conversion of methane into chemicals and fuels. The challenge of converting natural gas into transportable fuels and chemicals has been spurred by several emerging industrial trends, including rapidly rising demand for $H_2$ (for upgrading lower-quality oils) and a global shortage of aromatic hydrocarbons caused by shifting refinery targets toward gasoline. The commercial processes that are currently in practice convert methane into CO and $H_2$ and then convert the CO and $H_2$ into desired chemicals or fuels in a number of different processes. Methane activation and its selective conversion to chemicals and fuels is difficult due to the strength of the C—H bond in methane and the subsequent higher reactivity of the resulting products such as ethane, ethylene, or methanol.

Conversion of $CH_4$ into various chemicals has the potential of being more economical and environmentally friendly than other processes for producing the same chemicals, but is challenging because $CH_4$ exhibits high C—H bond strength (434 kJ/mol), negligible electron affinity, large ionization energy, and low polarizability. $CH_4$ can be converted to $C_{2+}$ hydrocarbons in the presence of oxygen at high temperatures in a process known as oxidative coupling of methane (OCM). While the overall OCM is exothermic, catalysts are used to overcome the endothermic nature of the C—H bond breakage. Hundreds of catalytic materials have been synthesized and tested for OCM; however, the presence of $O_2$ leads irreversibly to over-oxidation, resulting in a large amount of the thermodynamically stable end products $CO_2$ and $H_2O$, making the carbon utilization efficiency of OCM relatively low. When catalysts are used in the OCM, the exothermic reaction can lead to a large increase in catalyst bed temperature and uncontrolled heat excursions that can lead to catalyst deactivation and a further decrease in ethylene selectivity.

To achieve direct conversion of $CH_4$ efficiently, the challenges lie in cleaving the first C—H bond while suppressing further catalytic dehydrogenation, avoiding both $CO_2$ generation and coke deposition. $CH_4$ can be converted by non-oxidative coupling of methane, direct pyrolysis of methane to acetylene, dehydroaromatization of methane to benzene, etc. However, coke formation continues to be an issue during methane conversion processes. Thus, there is an ongoing need for the development of $CH_4$ conversion processes.

BRIEF SUMMARY

Disclosed herein is a method for producing $C_{2+}$ hydrocarbons and hydrogen comprising (a) introducing a reactant mixture to a reactor, wherein the reactant mixture comprises methane ($CH_4$), and wherein the reactor comprises a preheat zone, a primary reaction zone, a secondary reaction zone, and a quench zone, (b) heating the reactant mixture to a preheating temperature in the preheat zone to yield a heated reactant mixture, (c) generating free radicals in at least a portion of the heated reactant mixture in the primary reaction zone to form a primary effluent mixture comprising free radicals, $C_{2+}$ hydrocarbons, hydrogen, and unreacted methane, (d) reacting at least a portion of the primary effluent mixture in the secondary reaction zone to form a secondary effluent mixture comprising $C_{2+}$ hydrocarbons, hydrogen, free radicals, and unreacted methane, wherein the secondary reaction zone is characterized by a secondary reaction zone temperature, wherein the secondary reaction zone temperature is greater than the preheating temperature, wherein an amount of unreacted methane in the primary effluent mixture is greater than an amount of unreacted methane in the secondary effluent mixture, and wherein an amount of free radicals in the primary effluent mixture is greater than an amount of free radicals in the secondary effluent mixture, (e) cooling at least a portion of the secondary effluent mixture in the quench zone to a quench temperature to yield a product mixture comprising $C_{2+}$ hydrocarbons, hydrogen and unreacted methane, wherein the quench temperature is lower than the secondary reaction zone temperature, and (f) recovering at least a portion of the product mixture from the reactor.

Also disclosed herein is a method for producing $C_{2+}$ hydrocarbons and hydrogen comprising (a) introducing a reactant mixture to a reactor, wherein the reactant mixture comprises methane ($CH_4$), wherein the reactor comprises a preheat zone, a catalyzed reaction zone, an uncatalyzed reaction zone, and a quench zone, and wherein the catalyzed reaction zone comprises a catalyst, (b) heating the reactant mixture to a preheating temperature in the preheat zone to yield a heated reactant mixture, (c) contacting at least a portion of the heated reactant mixture with the catalyst in the catalyzed reaction zone to form a catalyst effluent mixture comprising free radicals, $C_{2+}$ hydrocarbons, hydrogen and unreacted methane, wherein the catalyzed reaction zone is characterized by a catalyzed reaction zone temperature and a catalyzed reaction zone residence time, and wherein the catalyzed reaction zone temperature is greater than the preheating temperature, (d) reacting at least a portion of the catalyst effluent mixture in the uncatalyzed reaction zone to form a reaction zone effluent mixture comprising $C_{2+}$ hydrocarbons, hydrogen, free radicals, and unreacted methane, wherein the uncatalyzed reaction zone is characterized by an uncatalyzed reaction zone temperature and an uncatalyzed reaction zone residence time, wherein the uncatalyzed reaction zone residence time is greater than the catalyzed reaction zone residence time, (e) cooling at least a portion of the reaction zone effluent mixture in the quench zone to a quench temperature to yield a product mixture comprising $C_{2+}$ hydrocarbons, hydrogen, and unreacted methane, wherein the quench temperature is lower than the uncatalyzed reaction zone temperature, and (f) recovering at least a portion of the product mixture from the reactor.

Also disclosed herein is an apparatus for converting a hydrocarbon stream to hydrogen and higher hydrocarbons (e.g., $C_{2+}$ hydrocarbons), wherein the apparatus can have an integrated catalyst-reactor design for achieving desired product selectivity and yields by controlling interphase and intraparticle heat and mass transport inside the apparatus to favor the production of alkyl radicals into the gas phase and by controlling the pyrolysis of products formed from the coupling of the alkyl radicals.

Also disclosed herein is a process for converting a hydrocarbon stream to hydrogen and higher hydrocarbons (e.g., $C_{2+}$ hydrocarbons) in the absence of oxygen, wherein the hydrocarbon stream can comprise low molecular weight hydrocarbons, and wherein the process can produce various products by controlling heat and mass transport in a reaction zone.

BRIEF DESCRIPTION OF THE DRAWINGS

For a detailed description of the preferred embodiments of the disclosed methods, reference will now be made to the accompanying drawings in which:

FIG. 1A displays a reactor configuration for co-feeding hydrogen at the start of the reaction;

FIG. 1B displays a reactor configuration for staged addition of hydrogen;

FIGS. 2A-C displays schematics of injector designs;

DETAILED DESCRIPTION

Figure 3:
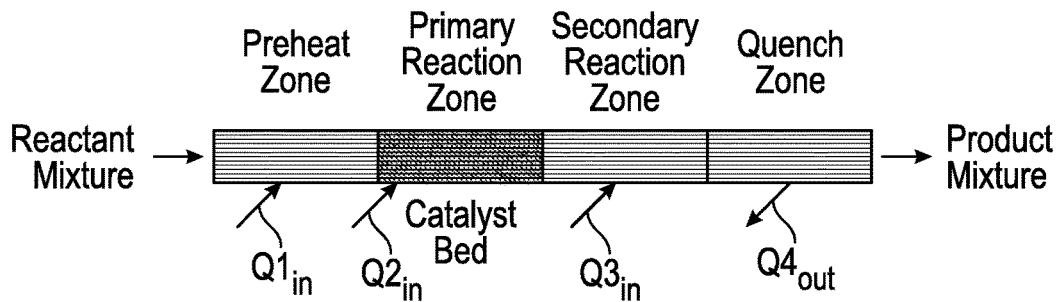
FIG. 3 displays a schematic of a reactor comprising a primary reaction zone comprising a catalyst bed.

Disclosed herein are methods for producing $C_{2+}$ hydrocarbons and hydrogen comprising (a) introducing a reactant mixture to a reactor, wherein the reactant mixture comprises methane ($CH_4$), and wherein the reactor comprises a preheat zone, a primary reaction zone, a secondary reaction zone, and a quench zone; (b) heating the reactant mixture to a preheating temperature in the preheat zone to yield a heated reactant mixture; (c) generating free radicals in at least a portion of the heated reactant mixture in the primary reaction zone to form a primary effluent mixture comprising free radicals, $C_{2+}$ hydrocarbons, hydrogen, and unreacted methane; (d) reacting at least a portion of the primary effluent mixture in the secondary reaction zone to form a secondary effluent mixture comprising $C_{2+}$ hydrocarbons, hydrogen, free radicals, and unreacted methane, wherein the secondary reaction zone is characterized by a secondary reaction zone temperature, wherein the secondary reaction zone temperature is greater than the preheating temperature, wherein an amount of unreacted methane in the primary effluent mixture is greater than an amount of unreacted methane in the secondary effluent mixture, and wherein an amount of free radicals in the primary effluent mixture is greater than an amount of free radicals in the secondary effluent mixture; (e) cooling at least a portion of the secondary effluent mixture in the quench zone to a quench temperature to yield a product mixture comprising $C_{2+}$ hydrocarbons, hydrogen and unreacted methane, wherein the quench temperature is lower than the secondary reaction zone temperature; and (f) recovering at least a portion of the product mixture from the reactor.

Other than in the operating examples or where otherwise indicated, all numbers or expressions referring to quantities of ingredients, reaction conditions, and the like, used in the specification and claims are to be understood as modified in all instances by the term "about." Various numerical ranges are disclosed herein. Because these ranges are continuous, they include every value between the minimum and maximum values. The endpoints of all ranges reciting the same characteristic or component are independently combinable and inclusive of the recited endpoint. Unless expressly indicated otherwise, the various numerical ranges specified in this application are approximations. The endpoints of all ranges directed to the same component or property are inclusive of the endpoint and independently combinable. The term "from more than 0 to an amount" means that the named component is present in some amount more than 0, and up to and including the higher named amount.

The terms "a," "an," and "the" do not denote a limitation of quantity, but rather denote the presence of at least one of the referenced item. As used herein the singular forms "a," "an," and "the" include plural referents.

As used herein, "combinations thereof" is inclusive of one or more of the recited elements, optionally together with a like element not recited, e.g., inclusive of a combination of one or more of the named components, optionally with one or more other components not specifically named that have essentially the same function. As used herein, the term "combination" is inclusive of blends, mixtures, alloys, reaction products, and the like.

Reference throughout the specification to "an embodiment," "another embodiment," "other embodiments," "some embodiments," and so forth, means that a particular element (e.g., feature, structure, property, and/or characteristic) described in connection with the embodiment is included in at least an embodiment described herein, and may or may not be present in other embodiments. In addition, it is to be understood that the described element(s) can be combined in any suitable manner in the various embodiments.

As used herein, the terms "inhibiting" or "reducing" or "preventing" or "avoiding" or any variation of these terms, include any measurable decrease or complete inhibition to achieve a desired result.

As used herein, the term "effective," means adequate to accomplish a desired, expected, or intended result.

As used herein, the terms "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains") are inclusive or open-ended and do not exclude additional, unrecited elements or method steps.

Unless defined otherwise, technical and scientific terms used herein have the same meaning as is commonly understood by one of skill in the art.

Compounds are described herein using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through the carbon of the carbonyl group.

In an embodiment, a method for producing $C_{2+}$ hydrocarbons and hydrogen can comprise introducing a reactant mixture to a reactor, wherein the reactant mixture comprises methane ($CH_4$), and wherein the reactor comprises a preheat zone, a primary reaction zone, a secondary reaction zone, and a quench zone; wherein methane can undergo a non-oxidative coupling of $CH_4$ reaction(s) to form a product mixture. For purposes of the disclosure herein, the term "zone" refers to a space or volume wherein a certain process or step thereof can occur. Further, for purposes of the disclosure herein, the reactor zones should not necessarily be construed as being discrete zones with distinct boundaries. For example, two or more reactor zones can overlap, e.g., a process or step thereof can occur to a certain extent in more than one reactor zone.

Further, while the present disclosure will be discussed in detail in the context of a reactor comprising a quench zone, it should be understood that in some reactor designs/configurations, the quench zone can comprise a zone outside the reactor for lowering the temperature of the secondary effluent mixture, such as a heat exchanger, a heat exchanger for heating up an incoming feed stream, a turbine, etc.

Non-oxidative coupling of $CH_4$ refers to reaction(s) that occur at high temperatures (e.g., over about 700° C.) in the absence of oxygen, wherein methane is converted into hydrocarbons. As an overall reaction, $CH_4$ is converted into hydrogen and ethylene, ethane, acetylene, and higher hydrocarbons, such as for example aromatic hydrocarbons (e.g., benzene, naphthalene, etc.). Generally, $CH_4$ is activated heterogeneously on a catalyst surface, forming methyl free radicals (e.g., —$CH_3$), which then exothermically couple in a gas phase to form ethane ($C_2H_6$). $C_2H_6$ can subsequently undergo dehydrogenation to form ethylene ($C_2H_4$). Higher hydrocarbons can be formed by further propagating the reaction through creation of hydrocarbon radicals.

In an embodiment, the reactant mixture can comprise a hydrocarbon or mixtures of hydrocarbons. In an embodiment, the reactant mixture can be a gaseous mixture. In some embodiments, the hydrocarbon or mixtures of hydrocarbons can comprise natural gas (e.g., $CH_4$), associated petroleum gas, liquefied petroleum gas comprising $C_2$-$C_5$ hydrocarbons, $C_{6+}$ heavy hydrocarbons (e.g., $C_6$ to $C_{24}$ hydrocarbons such as diesel fuel, jet fuel, gasoline, tars, kerosene, etc.), and the like, or combinations thereof. In an embodiment, the reactant mixture can comprise natural gas. Generally, natural gas is composed primarily of methane, but can also contain ethane, propane and heavier hydrocarbons (e.g., iso-butane, n-butane, iso-pentane, n-pentane, etc.), as well as very small quantities of nitrogen, oxygen, carbon dioxide, sulfur compounds, and/or water. In some embodiments, the natural gas can be provided from a variety of sources including, but not limited to, gas fields, oil fields, coal fields, fracking of shale fields, biomass, landfill gas, and the like, or combinations thereof.

In an embodiment, the reactant mixture can comprise a methane feed stream, wherein the methane feed stream can include a stream from a refinery and/or processing plant. For example, light alkanes, including methane, can often be separated in a refinery during processing of crude oil into various products, and a methane feed stream can be provided from the same refinery, a different refinery, and/or a refinery off gas. The methane feed stream can include a stream from combinations of different sources (e.g., streams from different refineries, different streams from the same refinery, etc.). The methane feed stream can be provided from a remote location and initial processing of the stream (e.g., refining or partial refining) can occur at the remote location to remove certain contaminants; the refining or partial refining can occur on site where the non-oxidative coupling of $CH_4$ reaction is conducted; or both.

In some embodiments, the reactant mixture can comprise $CH_4$ as a whole feed. In other embodiments, the reactant mixture can comprise $C_2H_6$ as a whole feed.

In an embodiment, the reactant mixture can exclude oxygen. In an embodiment, the reactant mixture can be substantially free of oxygen, or alternatively essentially free of oxygen. In an embodiment, the reactant mixture can comprise oxygen in an amount of less than about 1 mol %, alternatively less than about 0.5 mol %, alternatively less than about 0.1 mol %, alternatively less than about 0.01 mol %, alternatively less than about 0.001 mol %, or alternatively less than about 0.0001 mol %. In some embodiments, oxygen can be removed from the reactant mixture prior to introducing the reactant mixture to the reactor, e.g., the reactant mixture can be deoxygenated prior to introducing the reactant mixture to the reactor.

In an embodiment, the reactant mixture can exclude sulfur-containing compounds (e.g., $SO_x$, such as for example $SO_2$, S, and/or $RS_yR'$ type compounds). In an embodiment, the reactant mixture can be substantially free of sulfur-containing compounds, or alternatively essentially free of sulfur-containing compounds. In an embodiment, the reactant mixture can comprise sulfur-containing compounds in an amount of less than about 1 mol %, alternatively less than about 0.5 mol %, alternatively less than about 0.1 mol %, alternatively less than about 0.01 mol %, alternatively less than about 0.001 mol %, or alternatively less than about 0.0001 mol %. In some embodiments, sulfur-containing compounds can be removed from the reactant mixture prior to introducing the reactant mixture to the reactor.

In some embodiments, the reactant mixture can comprise sulfur (S) and/or sulfur-containing compounds (e.g., $SO_x$, such as for example $SO_2$, and/or $RS_yR'$ type compounds). Without wishing to be limited by theory, S and/or sulfur-containing compounds can reduce and/or prevent coke formation in a reactor, in a manner similar to reducing and/or preventing coke formation in thermal cracking furnaces such as ethane steam crackers. $SO_x$ compounds can be reduced to $H_2S$ under a reducing environment. Further, without wishing to be limited by theory, while S and/or sulfur-containing compounds could become incorporated into a reaction product and lower selectivity to desired products as well as deactivate certain catalysts, in a reducing environment with plenty of $H_2$ and high temperatures, S and/or sulfur-containing compounds could be converted into $H_2S$, which could help "immunize" the reactor walls by inhibiting coke formation.

In other embodiments, the reactant mixture can exclude S and/or sulfur-containing compounds. In an embodiment, the reactant mixture can be substantially free of S and/or sulfur-containing compounds, or alternatively essentially free of S and/or sulfur-containing compounds. In an embodiment, the reactant mixture can comprise S and/or sulfur-containing compounds in an amount of less than about 1 mol %, alternatively less than about 0.5 mol %, alternatively less than about 0.1 mol %, alternatively less than about 0.01 mol %, alternatively less than about 0.001 mol %, or alternatively less than about 0.0001 mol %. In some embodiments, S and/or sulfur-containing compounds can be removed from the reactant mixture prior to introducing the reactant mixture to the reactor.

In an embodiment, the reactant mixture can further comprise a diluent. In some embodiments, the diluent can be inert with respect to the non-oxidative coupling of $CH_4$ reaction (e.g., "inert diluent"), e.g., the diluent does not participate in the non-oxidative coupling of $CH_4$ reaction. In other embodiments, the diluent can be a reactant or a product of a non-oxidative coupling of $CH_4$ reaction, such as for example hydrogen ($H_2$). In an aspect, an inert diluent can be introduced to the reactor in a staged addition fashion. In embodiments where the diluent is a reactant or a product of a non-oxidative coupling of $CH_4$ reaction, the diluent can also be referred to as an "active diluent" or an "active co-feed," as the diluent can be "active" with respect to shifting the equilibrium of the non-oxidative coupling of $CH_4$ reaction, interacting with a catalyst, etc. As will be appreciated by one of skill in the art, and with the help of this disclosure, the addition to the reactor or any zone thereof of either a product or additional reactant will shift the reaction equilibrium, changing the extent of reaction, the conversion, and the final product mix.

In some configurations, a diluent can be added to a feed stream comprising a reactant mixture before entering the reactor (e.g., before entering the preheat zone of the reactor). Additionally or alternatively, a diluent containing stream can be introduced to the reactor independently of the feed stream comprising the reactant mixture. Nonlimiting examples of inert diluents suitable for use in the present disclosure can include nitrogen, inert gases, argon, neon, helium, krypton, xenon, carbon monoxide, carbon dioxide, and the like, or combinations thereof. Without wishing to be limited by theory, while carbon monoxide and carbon dioxide can be produced during non-oxidative coupling reactions, they are not expected to influence the equilibrium of the non-oxidative coupling reactions to a significant extent, e.g., they are not expected to influence the equilibrium of the non-oxidative coupling reactions to the same extent that hydrogen does, for example; and as such can be considered "inert" diluents. Nonlimiting examples of active diluents suitable for use in the present disclosure can include hydrogen, steam, natural gas components other than methane, ethane, propane, butanes, unsaturated hydrocarbons, and the like, or combinations thereof.

In an embodiment, the diluent (e.g., inert diluent and/or active diluent) can be present in the reactant mixture in an amount of from about 0.01% to about 95%, alternatively from about 0.1% to about 20%, or alternatively from about 1% to about 10%, based on the total volume of the reactant mixture.

In some embodiments, a $H_2$ containing stream can be added to a feed stream comprising a reactant mixture before entering the reactor (e.g., before entering the preheat zone of the reactor), to enrich the reactor environment with $H_2$. Additionally or alternatively, a $H_2$ containing stream can be added to the reactor or a zone thereof to enrich the environment of the reactor or a zone thereof with $H_2$, for example via a $H_2$ containing stream fed directly to the reactor or a zone thereof independently of the feed stream comprising the reactant mixture. Without wishing to be limited by theory, the addition of hydrogen, a product of the non-oxidative coupling reaction, to the reactor or a zone thereof controls the reaction equilibria in both the gas phase (e.g., $H_2$ impacts gas phase reactions) and on the catalytic surface (e.g., $H_2$ impacts surface catalysis reactions), when a catalyst is used in the process. Further, without wishing to be limited by theory, the addition of hydrogen can decrease the production of larger hydrocarbons, such as aromatic hydrocarbons, via hydrogenation and hydrocracking reactions, and consequently the formation of coke can be decreased. Hydrogen can help control the conversion and selectivity. As will be appreciated by one of skill in the art, and with the help of this disclosure, hydrogen can decrease methane conversion. In an embodiment, the addition of hydrogen to the reactor can increase the selectivity to ethylene, when compared to an otherwise similar process that employs the non-oxidative coupling of $CH_4$ reaction without hydrogen addition to the reactor. Further, as will be appreciated by one of skill in the art, and with the help of this disclosure, the amount of hydrogen that is introduced to the reactor has to be optimized for each particular reactor system in order to minimize the decrease in methane conversion and to maximize the increase in selectivity to ethylene.

Referring to FIG. 1A, hydrogen can be introduced to the reactor (e.g., a preheat zone of the reactor) as a co-feed for the feed stream comprising the reactant mixture. In some embodiments, the hydrogen can be introduced to the reactor in an amount of from about 0.01% to about 90%, alternatively from about 0.01% to about 50%, alternatively from about 0.01% to about 10%, or alternatively from about 1% to about 10%, based on the total volume of the reactant mixture. In other embodiments, a volumetric ratio of hydrogen to the feed stream comprising the reactant mixture can be from about 0.01:1 to about 10:1, alternatively from about 0.1:1 to about 5:1, or alternatively from about 0.5:1 to about 2:1.

Referring to FIG. 1B, the addition of hydrogen to the reactor or zone thereof can be staged at various points along a longitudinal length of the reactor. Without wishing to be limited by theory, a staged design of hydrogen addition allows for the precise control of surface radical formation and gas phase reactions. The staged hydrogen addition can also allow for better mixing of hydrogen gas and a reaction stream flowing through the reactor to maximize the effect of hydrogen on conversion and selectivity. While the present disclosure will be discussed in detail in the context of a staged design of hydrogen addition, it should be understood that in some reactor configurations, any suitable active diluent can be introduced to the reactor in a staged addition fashion.

Hydrogen can be added to one or more of the reactor zones. For example, hydrogen can be added to the preheat zone, such as illustrated in FIG. 1A where the hydrogen and the reactant mixture are co-fed to the reactor.

As another example, hydrogen can be added to the primary reaction zone, wherein the hydrogen can suppress coke formation. In order to maintain a desired level of hydrocarbon conversion, hydrogen can be added to the primary reaction zone in an amount of from about 0.01% to about 90%, alternatively from about 0.1% to about 50%, alternatively from about 0.5% to about 10%, or alternatively from about 1% to about 10% based on the total volume of the reactant mixture (e.g., heated reactant mixture). Hydrogen can be added to the primary reaction zone at a temperature that is about the same as a primary reaction zone temperature (e.g., from about 700° C. to about 1,300° C.), to avoid cooling down surface radical generation.

As yet another example, hydrogen can be added to the secondary reaction zone. A higher amount of hydrogen can be added to the secondary reaction zone, when compared to the amount of hydrogen added to the primary reaction zone. Without wishing to be limited by theory, the presence of hydrogen in the secondary reaction zone does not decrease significantly the methane conversion, however, it increases the selectivity to lighter hydrocarbons by promoting hydrocracking reactions and hydrogenation of aromatic hydrocarbons. Hydrogen can be added to the secondary reaction zone in an amount of from about 0.01% to about 90%, alternatively from about 0.1% to about 50%, alternatively from about 0.5% to about 10%, or alternatively from about 1% to about 10%, based on the total volume of the primary effluent mixture. Hydrogen can be added to the secondary reaction zone at a temperature that is about the same as a secondary reaction zone temperature (e.g., from about 700° C. to about 1,300° C.), to promote the propagation of reactions in the secondary reaction zone.

As still yet another example, hydrogen can be added to the quench zone. Hydrogen can be added to the quench zone in an amount of from about 0.01% to about 90%, alternatively from about 0.1% to about 50%, alternatively from about 0.5% to about 10%, or alternatively from about 1% to about 10%, based on the total volume of the secondary effluent mixture. Hydrogen can be added to the quench zone at a temperature that is less than a secondary reaction zone temperature (e.g., from about room temperature to about 700° C.), preferably at room temperature, to achieve quenching of the undergoing reactions.

As will be appreciated by one of skill in the art, and with the help of this disclosure, hydrogen can be added in different reactor zones at different volumetric ratios. For example, hydrogen can be added to the preheat zone at a first volumetric ratio of hydrogen to the reactant mixture; hydrogen can be added to the primary reaction zone at a second volumetric ratio of hydrogen to the heated reactant mixture; hydrogen can be added to the secondary reaction zone at a third volumetric ratio of hydrogen to the primary effluent mixture; hydrogen can be added to the quench zone at a fourth volumetric ratio of hydrogen to the secondary effluent mixture; or combinations thereof. In some embodiments, the first volumetric ratio, the second volumetric ratio, the third volumetric ratio, and the fourth volumetric ratio can all be different from each other; or alternatively at least two of the first volumetric ratio, the second volumetric ratio, the third volumetric ratio, and the fourth volumetric ratio can be the same.

In an embodiment, the reactant mixture can further comprise a promoter (e.g., an initiator, a radical propagation initiator, etc.). For purposes of the disclosure herein a "promoter" refers to a compound that requires less energy input than $CH_4$ for the formation of a free radical. As will be appreciated by one of skill in the art, and with the help of this disclosure, the promoter can be converted into a free radical more easily than the $CH_4$, and such a free radical can "jump start" the radical chain process. In an embodiment, the presence of a promoter in the reactant mixture can allow for using a lower temperature in the preheat zone and/or the primary reaction zone when compared to a temperature in the preheat zone and/or the primary reaction zone in the absence of a promoter.

Nonlimiting examples of promoters suitable for use in the present disclosure include alkanes, ethane, propane, alkenes, naphthalene, functionalized hydrocarbons such as halogenated hydrocarbons, halogenated alkanes, chlorinated alkanes, methyl chloride, methylene chloride, carbon tetrachloride, chloroethane, brominated alkanes, methyl bromide, radical initiators, alcohols, ethers, and the like, or combinations thereof.

In an embodiment, the promoter can be present in the reactant mixture in an amount of from about 0.01 mol % to about 20 mol %, alternatively from about 0.1 mol % to about 10 mol %, or alternatively from about 0.2 mol % to about 1.0 mol %. As will be appreciated by one of skill in the art, and with the help of this disclosure, certain promoters, such as ethane, propane, butane, pentanes, carbon dioxide, and nitrogen, can be inherently present in the natural gas used in the reactant mixture, and as such these promoters will be present in the reactant mixture in an amount based on their abundance in the natural gas used in the reactant mixture.

In an embodiment, a $C_{2+}$ alkane (i.e., an alkane having 2 or more carbon atoms) can be introduced to the reactor. In some configurations, a $C_{2+}$ alkane can be added to a feed stream comprising a reactant mixture before entering the reactor (e.g., before entering the preheat zone of the reactor). Additionally or alternatively, a $C_{2+}$ alkane containing stream can be introduced to the reactor independently of the feed stream comprising the reactant mixture. Nonlimiting examples of a $C_{2+}$ alkanes suitable for use in the present disclosure can include ethane, propanes (e.g., n-propane, iso-propane), butanes, light naphtha (e.g., $C_{5-6}$ alkanes), liquefied petroleum gas (e.g., $C_{3-4}$ alkanes), and the like, or combinations thereof. In some embodiments, $C_{2+}$ alkanes can be isolated (e.g., recovered, separated) from a product mixture recovered from the reactor and can be further recycled to the reactor or a zone thereof.

In an embodiment, the $C_{2+}$ alkane can be present in the reactant mixture in an amount of from about 0.01% to about 100%, alternatively from about 0.1% to about 90%, or alternatively from about 1% to about 25%, based on the total volume of the reactant mixture.

In an embodiment, a reactant mixture to $C_{2+}$ alkanes (e.g., $CH_4/C_2H_6$) volumetric ratio can be from about 1:1 to about 20:1, or alternatively from about 5:1 to about 10:1. In some embodiments, $C_{2+}$ alkanes (e.g., ethane) can be added to the quenching zone alone or with water (e.g., water vapor). In embodiments where the $C_{2+}$ alkanes are added to the quench zone along with water, a volumetric ratio of $C_{2+}$ alkanes (e.g., ethane) to water (e.g., water vapor) can be from about 1:1 to about 1:3.

Without wishing to be limited by theory, the addition of $C_{2+}$ alkanes to the reactor can increase desired unsaturated hydrocarbon yields (e.g., olefin yields), such as ethylene yield in the case of ethane addition, and can help quench gas phase reactions, leading to improved performance by utilizing the $C_{2+}$ alkanes to undergo endothermic reactions (e.g., dehydrogenation), thereby capturing the heat of the non-oxidative reaction and lowering the temperature of the reaction zone effluents (e.g., primary reaction zone effluent, secondary reaction zone effluent). As will be appreciated by one of skill in the art, and with the help of this disclosure, the $C_{2+}$ alkanes may perform more than one function in the reactor. For example, the $C_{2+}$ alkanes, when introduced to the preheat zone and/or the primary reaction zone, can participate in non-oxidative coupling reactions and form radicals. Further, $C_{2+}$ alkanes, when introduced to the secondary reaction zone and/or the quench zone as a "fresh" feed and/or as unreacted $C_{2+}$ alkanes in the primary reaction zone effluent and/or secondary reaction zone effluent, respectively, can undergo endothermic reactions, such as dehydrogenation, and can produce desired unsaturated hydrocarbons (e.g., ethylene, propylene, butylene, etc.). While the present disclosure will be discussed in detail in the context of introducing $C_{2+}$ alkanes to the reactor to undergo endothermic reactions and thereby lower the temperature, it should be understood that any other suitable compound that can undergo endothermic reactions and is compatible with the processes disclosed herein could be introduced to the reactor to lower the temperature.

In some embodiments, a $C_{2+}$ alkane containing stream can be added to a feed stream comprising a reactant mixture before entering the reactor (e.g., before entering the preheat zone of the reactor), to enrich the reactor environment with $C_{2+}$ alkanes. Additionally or alternatively, a $C_{2+}$ alkane containing stream can be added to the reactor or a zone thereof to enrich the environment of the reactor or a zone thereof with $C_{2+}$ alkanes, for example via a $C_{2+}$ alkane containing stream fed directly to the reactor or a zone thereof independently of the feed stream comprising the reactant mixture. Without wishing to be limited by theory, the addition of a $C_{2+}$ alkane, a reactant in the non-oxidative coupling reaction, to the reactor or a zone thereof controls the reaction equilibria in both the gas phase (e.g., $C_{2+}$ alkanes impact gas phase reactions) and on the catalytic surface (e.g., $C_{2+}$ alkanes impact surface catalysis reactions), when a catalyst is used in the process.

In some embodiments, the $C_{2+}$ alkane can be introduced to the reactor (e.g., a preheat zone of the reactor) as a co-feed for the feed stream comprising the reactant mixture. In other embodiments, the addition of the $C_{2+}$ alkane to the reactor or zone thereof can be staged at various points along a longitudinal length of the reactor. Without wishing to be limited by theory, a staged design of $C_{2+}$ alkane addition allows for using the heat of the reactor effluent (e.g., primary reaction zone effluent and/or secondary reaction zone effluent) to generate additional desirable unsaturated hydrocarbons, such as ethylene.

$C_{2+}$ alkanes can be added to one or more of the reactor zones. For example, $C_{2+}$ alkanes can be added to the preheat zone, where the $C_{2+}$ alkanes and the reactant mixture are co-fed to the reactor. As another example, $C_{2+}$ alkanes can be added to the primary reaction zone, wherein a portion of the $C_{2+}$ alkanes can undergo a non-oxidative coupling reaction. $C_{2+}$ alkanes can be added to the primary reaction zone at a temperature that is about the same as a primary reaction zone temperature (e.g., from about 700° C. to about 1,300° C.), to avoid cooling down surface radical generation.

In an embodiment, $C_{2+}$ alkanes can be added to the secondary reaction zone. The $C_{2+}$ alkanes can be added to the secondary reaction zone at a temperature that is lower than the secondary reaction zone temperature, to promote endothermic dehydrogenation reactions in the secondary reaction zone, wherein the endothermic dehydrogenation reactions can produce additional desirable unsaturated hydrocarbons, such as ethylene. In embodiments where the secondary reaction zone temperature is lower than the primary reaction zone temperature, the $C_{2+}$ alkanes can be added to the secondary reaction zone in an amount effective to lower the temperature of the primary reaction effluent to the secondary reaction zone temperature. As will be appreciated by one of skill in the art, and with the help of this disclosure, the amount of $C_{2+}$ alkanes added to the secondary reaction zone is dependent on the amount of unreacted $C_{2+}$ alkanes present in the primary reaction zone effluent.

In another embodiment, $C_{2+}$ alkanes can be added to the quench zone. $C_{2+}$ alkanes can be added to the quench zone at a temperature that is less than a secondary reaction zone temperature (e.g., from about room temperature to about 700° C.), to capture the heat via endothermic dehydrogenation reactions and achieve concurrently quenching of the undergoing radical propagation reactions.

Addition of additives (e.g., diluents, promoters, quenching agents such as diluents used as quenching agents, $C_{2+}$ alkanes, and the like, or combinations thereof) to the reactor can be done in any suitable manner. In some embodiments, an injection nozzle can be used for introducing additives to the reactor. In other embodiments, an assembly (e.g., injector assembly) of a plurality of injection nozzles can be radially distributed within a reactor (e.g., a reactor tube) for introducing additives to the reactor, such as for example as depicted in FIGS. 2A-C. The nozzles may inject additives at different radial depths. The number of nozzles in an assembly may be 1 to about 50, alternatively 2 to about 40, or alternatively 3 to about 30. As will be appreciated by one of skill in the art, and with the help of this disclosure, while an arrangement of the nozzles can be aligned in transverse planes, the nozzles may be distributed in any other manner suitable to achieve a desired angular distribution and radial distribution in a stream flowing through a reactor. In some configurations, an injector assembly can be a separate component (e.g., separate from a body of the reactor) disposed in the body of the reactor. In other configurations, the injector assembly can be integral with the body of the reactor.

Referring to FIGS. 2A-C, a more uniform distribution and/or radial penetration of additive can be achieved with a design having a plurality of injection nozzles, wherein the injection nozzles can be radially distributed between one or more (e.g., two) assemblies on multiple planes. FIG. 2A displays an injector assembly 100 comprising four nozzles 110 characterized by a penetration depth 170 (e.g., nozzles 110 configured to inject an additive to a radial depth as indicated by 170). Each of the nozzles 110 can disperse 150 an additive for an even distribution centered around a target area 120. FIG. 2B displays an injector assembly 200 comprising injection nozzles 210 characterized by a penetration depth 270 (e.g., nozzles 210 configured to inject an additive to a radial depth as indicated by 270). Each of the nozzles 210 can disperse 250 an additive for an even distribution centered around a target area 220. FIG. 2C displays an injector assembly 300 that combines the injector assembly 100 and the injector assembly 200, wherein each nozzle can be configured to deliver an additive to a desired target location for a given stream velocity.

In an embodiment, a design for the addition of additives (e.g., diluents, promoters, quenching agents such as diluents used as quenching agents, $C_{2+}$ alkanes, and the like, or combinations thereof) to a reactor can include, but is not limited to, one or more injection quills (e.g., a tubular injection insert through a reactor wall or port, wherein the insert extends into an inner volume of the reactor) for introducing the additives in a center of the reactor. In an embodiment, an injection quill can be placed on either side of a reactor mixer (e.g., before and/or after a mixer in a reactor). In an embodiment, an injection quill can be placed either side of an injection nozzle and/or plurality of injection nozzles (e.g., before and/or after an injection nozzle and/or plurality of injection nozzles), wherein the injection nozzle and/or plurality of injection nozzles (e.g., FIG. 2) can be configured to inject material (e.g., additives) into a respective stream from the sides of the reactor(s) inside the reactor.

In an embodiment, a method for producing $C_{2+}$ hydrocarbons and hydrogen can comprise introducing the reactant mixture to a reactor, wherein the reactor can comprise a tubular reactor, a continuous flow reactor, a riser reactor, a reformer reactor, a fixed bed reactor, a shock tube reactor, a multi-tubular reactor, a membrane reactor, a dual flow reactor, a gauze reactor, a fluidized bed reactor, a moving bed reactor, a continuous stirred-tank reactor (CSTR), a plug flow reactor (PFR), a microchannel reactor, a modular reactor, a modular microchannel reactor, a honeycombed monolithic reactor, a honeycombed wall filter monolithic reactor, and the like, or combinations thereof. In an embodiment, the reactor can comprise a reformer reactor, a fixed bed reactor, a fluidized bed reactor, a moving bed reactor, and the like, or combinations thereof.

Generally, a CSTR is an open system reactor, wherein material is free to enter or exit the system. CSTRs operate on a steady-state basis, wherein reactor conditions do not change over time, and wherein reactants are continuously introduced into the reactor, while products are continuously removed. CSTRs are very well mixed (e.g., by using an apparatus that causes mixing, such as a swirl mixer), such that reactor contents have relatively uniform properties, such as for example temperature, density, etc. throughout. It is generally considered that conditions in a CSTR's exit stream are the same as conditions inside the CSTR.

In another embodiment, the reactor can have a sudden change in an inner diameter (as opposed to using an apparatus that causes mixing) wherein such sudden diameter change can cause back mixing, and wherein a degree of back mixing can be dependent upon a reactor design and/or process conditions.

Generally, a PFR, which can also be referred to as a flow tube reactor, can comprise a fluid flowing through the PFR as a series of "plugs," each plug having an uniform composition (e.g., each plug is thoroughly mixed, as is the case with a CSTR) and traveling in an axial direction of the reactor. Fluid flow is continuous through the PFR, usually at steady state, and is configured such that conversion of chemicals and other dependent variables are functions of position within the reactor rather than of time. The fluid flowing through the PFR is mixed in the radial direction, but not in the axial direction (forwards or backwards).

Two of the principal reactions in converting alkanes to olefins and aromatics (e.g., aromatic hydrocarbons) are homolytic scission of the C—H bond and dehydrogenation of alkanes, both being endothermic reactions and promoted by a rise in temperature, and therefore necessitate high temperatures. These two reactions (e.g., homolytic scission of the C—H bond and dehydrogenation of alkanes) can also cause an increase in the number of molecules, which in turn means that they can be promoted by low partial pressures of the hydrocarbons to be processed (e.g., reactant mixture), and for that reason a partial pressure of reactants in a reactor can be reduced as much as possible by addition of a diluent to the reactant mixture. As will be appreciated by one of skill in the art, and with the help of this disclosure, in order to increase a selectivity of the process (e.g., non-oxidative coupling of methane reactions) towards olefins and/or aromatics production, it is desirable: for a temperature of a feed stream (e.g., reactant mixture) to not exceed an optimum reaction temperature for a given composition of the reactant mixture in the preheat zone, so as to not promote fouling or coking in the preheat zone or downstream in a reaction zone; maintenance of such optimum reaction temperature in a reaction zone; optimization and/or reduction of the residence time of a feed (e.g., reactant mixture) in the primary reaction zone; optimization and/or reduction of partial pressure of the reactant mixture in the primary reaction zone; maintenance of an optimum reaction temperature in the secondary reaction zone; optimization and/or reduction of the residence time of a feed (e.g., primary effluent mixture) in the secondary reaction zone; optimization and/or reduction of partial pressure of the primary effluent mixture in the secondary reaction zone; and rapid and efficient quenching of reaction effluents (e.g., secondary effluent mixture). Such desirable features for increasing a selectivity towards olefins and/or aromatics could be achieved by a general method scheme comprising: a) preheating a feed stream (e.g., reactant mixture), wherein the feed stream can be diluted with an inert gas; b) heating the feed stream at high temperatures, using catalyst(s) at flows to optimize a residence time of hydrocarbons in a catalytic reaction zone, and producing a reactive effluent stream in the catalytic reaction zone; c) heating the reactive effluent stream at high temperatures at flows to optimize a residence time of the reactive effluent stream in the secondary reaction zone; and d) rapid quenching of a product effluent of the secondary reaction zone. Reactor designs can essentially be directed towards obtaining optimal shorter residence times and a reduction in a pressure drop by reducing reactor lengths and increasing a heat flow density. An increase in the heat flow density can be achieved by increasing a temperature of reactor walls and/or by reducing a diameter of pipes used in reactor design (e.g., microchannels), which enables a s/v ratio to be increased, wherein s is a heat exchange surface and v is a reaction volume. In an embodiment, the s/v ratio can be from about $1.0 \text{ m}^{-1}$ to about $1,000 \text{ m}^{-1}$, alternatively from about $10 \text{ m}^{-1}$ to about $500 \text{ m}^{-1}$, alternatively from about $100 \text{ m}^{-1}$ to about $500 \text{ m}^{-1}$, alternatively from about $120 \text{ m}^{-1}$ to about $500 \text{ m}^{-1}$, alternatively from about $120 \text{ m}^{-1}$ to about $200 \text{ m}^{-1}$, alternatively up to about $200 \text{ m}^{-1}$, or alternatively up to about $1,000 \text{ m}^{-1}$. In an embodiment, the reactor can comprise special alloys that allow operating at high reaction temperatures, including, but not limited to a superalloy, duplex stainless steel, super duplex stainless steel, nickel-based high temperature low creep superalloy (e.g., INCONEL 718 alloy, which is an austenite nickel-chromium based superalloy), HAYNES 214 alloy, INCOLOY 800H, HK40, and HP40 for example. In an embodiment, the reactor can further comprise an inner shell consisting of a carbide, a nitride, titanium diboride, a sialon ceramic, zirconia, thoria, a carbon-carbon composite, tungsten, tantalum, molybdenium, chromium, nickel, and the like, alloys thereof, or combinations thereof. In an embodiment, the reactor can comprise smaller diameter pipes (e.g., microchannels), placed in parallel with each other in order to maintain a satisfactory capacity and still provide a suitable pressure drop (e.g., in a manner similar to pyrolysis pipe stills). Elongated oval and dumb-bell shaped cross-sections of pipes can improve heat flow density, when compared to round cross-sections. In some embodiments, the reactor (e.g., reactor walls, reactor zone walls) can comprise an inner surface, such as quartz or ceramic. In other embodiments, the reactor (e.g., reactor walls, reactor zone walls) can be comprised of a material, such as quartz or ceramic. In yet other embodiments, an inner reactor surface (e.g., an inner reactor wall surface, an inner reactor zone wall surface) can be lined or coated with a material, such as quartz or ceramic. In still yet other embodiments, the reactor (e.g., reactor walls, reactor zone walls) can comprise an inner chemically reactive surface. For purposes of the disclosure herein, the term "chemically reactive material" refers to a material that can participate in a reaction that occurs in the reactor or a zone thereof; and/or a material that can change a local concentration of reactants and/or products associated with a reaction that occurs in the reactor or a zone thereof. For example, the reaction can be the non-oxidative coupling of a hydrocarbon (e.g., methane), wherein the chemically reactive material can comprise a catalyst; a quenching reaction or a radical termination reaction, wherein the chemically reactive material can comprise a radical trap or terminator material; etc. In some configurations, the chemically reactive material/surfaces can enhance a function of a particular reactor zone, such as for example catalysis of oxidative coupling reactions in a reaction zone (e.g., primary reaction zone; secondary reaction zone); a radical trap or terminator in the quench zone; a selective membrane; etc. In still yet other embodiments, the reactor (e.g., reactor walls, reactor zone walls) can be comprised of a chemically reactive material. In still yet other embodiments, an inner reactor surface (e.g., an inner reactor wall surface, an inner reactor zone wall surface) can be lined or coated with a chemically reactive material (e.g., a selective membrane) that can allow a component to selectively pass or diffuse through the chemically reactive material. As will be appreciated by one of skill in the art, and with the help of this disclosure, such a selective membrane can cause a change in process chemistry, for example when the component that can selectively pass through the membrane is either reacting in or is produced by the oxidative coupling reaction (e.g., hydrogen, ethane, ethylene, etc.). In some configurations, the inner reactor surface can be lined with a membrane that selectively allows H. or $H_2$ to pass through the membrane layer, and to be further recovered as $H_2$ or a derivative thereof (e.g., a compound that incorporates the H. or $H_2$ that passed through the membrane). In still yet other embodiments, an inner reactor surface (e.g., an inner reactor wall surface, an inner reactor zone wall surface) can be lined or coated with a chemically reactive material.

In some embodiments, the uncatalyzed reaction zone can comprise a chemically reactive material that can preferentially react or interact with one or more components of a catalyst effluent mixture (e.g., an effluent from a catalyzed reaction zone). In other embodiments, the uncatalyzed reaction zone can comprise a mixture of chemically reactive materials, wherein the mixture can preferentially react with one or more components of the catalyst effluent mixture. The chemically reactive material can enable the coupling of components of the catalyst effluent mixture, thereby changing a product mixture distribution (e.g., changing a composition of the product mixture), when compared to a product mixture produced in the absence of the chemically reactive material in the uncatalyzed reaction zone.

In an embodiment, a method for producing $C_{2+}$ hydrocarbons and hydrogen can comprise heating the reactant mixture to a preheating temperature in the preheat zone to yield a heated reactant mixture. In an embodiment, the preheating temperature can be from about 200° C. to about 800° C., alternatively from about 550° C. to about 950° C., or alternatively from about 700° C. to about 1200° C. In an embodiment, the reactant mixture can be heated by using any suitable methodology, such as for example by external heat exchange, electric heating, electric arc heating, microwave heating, radiant heating produced by burning a portion of the reactant mixture with oxygen to directly heat the reactor, $H_2$ combustion, natural gas combustion, solar heating, infrared heating, microwave heating, thermally coupled exothermic reactions with an endothermic reaction (e.g., selective oxidation reactions coupled with radical generation), isothermal pyrolysis wherein heat can be supplied through a reactor wall by resistance heating, and the like, or combinations thereof.

In some embodiments, the reactant mixture can be heated to a temperature (e.g., preheating temperature) lower than a temperature at which homogeneous pyrolysis occurs that would lead to alkane (e.g., $CH_4$) activation (e.g., methyl radical formation) and formation of hydrogen, alkenes, alkynes and coke. As will be appreciated by one of skill in the art, and with the help of this disclosure, the preheating temperature should not be high enough as to prematurely cause a gas phase homolytic bond cleavage of methane and/or surface catalyzed reactions with the reactor walls (e.g., to generate radicals in the reactant mixture in the preheat zone).

In some embodiments, the preheating temperature can be non-uniform radially and/or along a length of the preheat zone. The preheating temperature can be characterized by a gradient along the length of the preheat zone. For example, the preheating temperature can gradually increase along the length of the preheat zone. The preheating temperature can have any suitable temperature profile effective for achieving a desired reactant mixture temperature as the reactant mixture enters the primary reaction zone.

In other embodiments, the preheating temperature can be uniform along the length of the preheat zone, e.g., the preheat zone temperature can be substantially the same along the length of the preheat zone.

As will be appreciated by one of skill in the art, and with the help of this disclosure, while coupling of free radicals (e.g., methyl radicals) is exothermic, heat input is necessary for promoting the formation of methyl radicals from $CH_4$, as the C—H bonds of $CH_4$ are very stable, and the formation of methyl radicals from $CH_4$ is endothermic. Further, as will be appreciated by one of skill in the art, and with the help of this disclosure, while the non-oxidative coupling of $CH_4$ reaction(s) does not occur in the preheat zone, the preheating temperature brings the methane molecules energetically closer to a point where the formation of methyl radicals can occur.

In an embodiment, the preheat zone can be characterized by a preheat zone residence time. Generally, the preheat zone residence time refers to the average amount of time that a compound such as methane (e.g., a molecule of that compound) spends in that particular preheat zone. In an embodiment, the preheat zone can be characterized by a preheat zone residence time effective for the reactant mixture to reach the preheating temperature.

In an embodiment, the preheat zone residence time can be from about 1.0 millisecond (ms) to about 1 second (s), alternatively from about 10.0 ms to about 10 s, or alternatively from about 10.0 s to about 100 s.

In an embodiment, a method for producing $C_{2+}$ hydrocarbons and hydrogen can comprise generating free radicals in at least a portion of the heated reactant mixture in the primary reaction zone to form a primary effluent mixture comprising free radicals, $C_{2+}$ hydrocarbons, hydrogen, and unreacted methane. For purposes of the disclosure herein, the primary reaction zone can also be referred to as "radical generation zone," and the terms "radical generation zone" and "primary reaction zone" can be used interchangeably. In some configurations, the primary reaction zone can be a physically separated zone from the preheat zone and the secondary reaction zone. In other configurations, the primary reaction zone can be integrated with other zones, such as but not limited to the secondary reaction zone. In still yet other configurations, the primary reaction zone can be coupled with a zone that would supply some or all of the heat required for the process, such as but not limited to the preheat zone.

In an embodiment, the free radicals can be generated in the primary reaction zone by any suitable methodology. In some embodiments, the free radicals can be generated catalytically, wherein the primary reaction zone can be a catalyzed reaction zone. In other embodiments, the free radicals can be generated in the primary reaction zone by plasma sources, such as for example dielectric barrier discharge, cold plasma, corona discharge, glow discharge, gliding arc, spark discharge, microwave plasma, and the like, or combinations thereof. In yet other embodiments, the free radicals can be generated in the primary reaction zone by a supersonic hot gas stream. In still yet other embodiments, the free radicals can be generated in the primary reaction zone by photo-dissociation under irradiation with ultraviolet (UV) or visible radiation, such as for example by irradiation with ultraviolet photons, vacuum-ultraviolet (VUV) photons, etc. Some of these methods can be combined with each other. For example, the free radicals can be generated in the primary reaction zone by photocatalysis, wherein the free radicals are generated by irradiation with UV radiation in the presence of a catalyst. Methods for generating free radicals are described in more detail in J. Phys. Chem. 1994, vol. 98, pp 206-210; Catalysis Reviews 2003, vol. 45, No. 1, pp. 151-203; J. Phys. Chem. C 2014, vol. 118, pp 10686-10693; U.S. Publication Nos. 20140056766 A1 and 20140056767 A1; and U.S. Pat. Nos. 4,136,015; 4,724,272 and 7,183,451; each of which is incorporated by reference herein its entirety.

In an embodiment, a method for producing $C_{2+}$ hydrocarbons and hydrogen can comprise heating the primary reaction zone to a primary reaction zone temperature. In an embodiment, the primary reaction zone can be characterized by a primary reaction zone temperature effective for generating free radicals and/or promoting free radical generation. Generating methyl radicals from $CH_4$ is a highly endothermic process that requires energy input, which could be thermal energy provided in the form of heating the entire primary reaction zone; plasma energy in an isolated part of the primary reaction zone, optionally coupled with heating at least a portion of the primary reaction zone; kinetic energy to the $CH_4$ molecules (e.g., accelerating the $CH_4$ molecules in a supersonic hot gas stream), optionally coupled with heating at least a portion of the primary reaction zone; and the like, or combinations thereof.

In an embodiment, the primary reaction zone temperature can be equal to or greater than about 700° C., alternatively equal to or greater than about 800° C., alternatively equal to or greater than about 900° C., alternatively from about 700° C. to about 1,300° C., alternatively from about 800° C. to about 1,200° C., or alternatively from about 900° C. to about 1,100° C. In some embodiments, the primary reaction zone temperature can be greater than the preheating temperature. In an embodiment, the primary reaction zone can be heated by using any suitable methodology, such as for example by external heat exchange, electric heating, electric arc heating, microwave heating, radiant heating produced by burning a portion of the reactant mixture with oxygen to directly heat the reactor, $H_2$ combustion, natural gas combustion, solar heating, infrared heating, microwave heating, thermally coupled exothermic reactions with an endothermic reaction (e.g., selective oxidation reactions coupled with the radical generation), isothermal pyrolysis wherein heat can be supplied through a reactor wall by resistance heating, and the like, or combinations thereof.

In an embodiment, the heated reactant mixture entering the primary reaction zone can be characterized by a heated reactant mixture pressure effective for achieving a desired amount of free radicals (e.g., a first amount of free radicals) in the primary effluent mixture (e.g., a concentration of free radicals in a gas phase) and/or a desired amount of species formed from the free radicals (such as $C_{2+}$ hydrocarbons) in the primary effluent mixture (e.g., a concentration of species formed from the free radicals in a gas phase). In an embodiment, the heated reactant mixture entering the primary reaction zone can be characterized by a heated reactant mixture pressure of from about 0.1 bar (100 kPa) to about 40 bar (4,000 kPa), alternatively from about 1 bar to about 20 bar, or alternatively from about 2 bar to about 10 bar.

In an embodiment, a pressure of a feed gas (e.g., reactant mixture) can be from about 0.1 bar (100 kPa) to about 40 bar (4,000 kPa), alternatively from about 1 bar to about 20 bar, or alternatively from about 2 bar to about 10 bar, to achieve a desired conversion and/or selectivity.

In an embodiment, the primary reaction zone can be characterized by a primary reaction zone residence time. Generally, the primary reaction zone residence time refers to the average amount of time that a compound such as methane (e.g., a molecule of that compound that does not undergo a chemical reaction in the primary reaction zone) spends in that particular primary reaction zone. In an embodiment, the primary reaction zone can be characterized by a primary reaction zone residence time effective for achieving a desired amount of free radicals (e.g., a first amount of free radicals) in the primary effluent mixture (e.g., a concentration of free radicals in a gas phase) and/or a desired amount of species formed from the free radicals (such as $C_{2+}$ hydrocarbons) in the primary effluent mixture (e.g., a concentration of species formed from the free radicals in a gas phase). As will be appreciated by one of skill in the art, and with the help of this disclosure, if higher primary reaction zone temperatures are used, then lower primary reaction zone residence times (e.g., contact times in the case of a catalyzed reaction zone) might be used to maintain a desired selectivity and provide for coke-free operations.

In an embodiment, the primary reaction zone residence time can be from about 0.01 ms to about 100 ms, alternatively from about 0.1 ms to about 100 ms, alternatively from about 10 ms to about 10 s, or alternatively from about 100 ms to about 100 s.

In some embodiments, the primary reaction zone temperature and/or the primary reaction zone residence time can be modified such that a desired concentration of a specific component(s) can be achieved. For example, a shorter residence time and a lower temperature could maximize the formation of ethane in the primary reaction zone. Further, for example, a shorter residence time and a higher temperature could maximize the formation of free radicals from methane in the primary reaction zone. When ethane is present in the primary reaction zone, a lower temperature would be effective to promote the formation of free radicals from ethane.

In some embodiments, the free radicals can be generated catalytically, wherein the primary reaction zone can be a catalyzed reaction zone comprising a catalyst. In an embodiment, the catalyzed reaction zone can comprise a catalyst bed comprising a catalyst.

In an embodiment, a method for producing $C_{2+}$ hydrocarbons and hydrogen can comprise contacting at least a portion of the heated reactant mixture with the catalyst in the catalyzed reaction zone to form a catalyst effluent mixture comprising free radicals, hydrocarbons (e.g., $C_{2+}$ hydrocarbons), hydrogen and unreacted methane.

In an embodiment, a method for producing $C_{2+}$ hydrocarbons and hydrogen can comprise heating the catalyzed reaction zone to a catalyzed reaction zone temperature. In an embodiment, the catalyzed reaction zone can be characterized by a catalyzed reaction zone temperature effective for generating free radicals and/or promoting free radical generation. Generating methyl radicals from $CH_4$ is a highly endothermic process that requires energy input, which could be thermal energy provided in the form of heating the entire catalyzed reaction zone. In an embodiment, the catalyzed reaction zone can be heated by using any suitable methodology, for example by external heat exchange, electric heating, electric arc heating, microwave heating, radiant heating produced by burning a portion of the reactant mixture with oxygen to directly heat the reactor, $H_2$ combustion, natural gas combustion, solar heating, infrared heating, microwave heating, thermally coupled exothermic reactions with an endothermic reaction (e.g., selective oxidation reactions coupled with the radical generation), isothermal pyrolysis wherein heat can be supplied through a reactor wall by resistance heating, and the like, or combinations thereof.

In an embodiment, the catalyzed reaction zone temperature can be equal to or greater than about 600° C., alternatively equal to or greater than about 800° C., alternatively equal to or greater than about 900° C., alternatively from about 700° C. to about 1,300° C., alternatively from about 750° C. to about 1,200° C., or alternatively from about 950° C. to about 1,180° C. As will be appreciated by one of skill in the art, and with the help of this disclosure, different catalysts have different deactivation temperatures, and as such the catalyzed reaction zone temperature can vary based on the type of catalyst used. In an embodiment, the catalyzed reaction zone temperature can be greater than the preheating temperature.

In an embodiment, the heated reactant mixture entering the catalyzed reaction zone can be characterized by a heated reactant mixture pressure effective for achieving a desired amount of free radicals (e.g., a first amount of free radicals) in the primary effluent mixture (e.g., a concentration of free radicals in a gas phase) and/or a desired amount of species formed from the free radicals (such as $C_{2+}$ hydrocarbons) in the primary effluent mixture (e.g., a concentration of species formed from the free radicals in a gas phase). In an embodiment, the heated reactant mixture entering the catalyzed reaction zone can be characterized by a heated reactant mixture pressure of from about 0.1 bar (100 kPa) to about 40 bar (4,000 kPa), alternatively from about 1 bar to about 20 bar, or alternatively from about 2 bar to about 10 bar.

In an embodiment, the catalyzed reaction zone can be characterized by a catalyzed reaction zone residence time. Generally, the catalyzed reaction zone residence time refers to the average amount of time that a compound such as methane (e.g., a molecule of that compound that does not undergo a chemical reaction in the catalyzed reaction zone) spends in that particular catalyzed reaction zone. In an embodiment, the catalyzed reaction zone can be characterized by a catalyzed reaction zone residence time effective for achieving a desired amount of free radicals (e.g., a first amount of free radicals) in the catalyst effluent mixture (e.g., a concentration of free radicals in a gas phase) and/or a desired amount of species formed from the free radicals (such as $C_{2+}$ hydrocarbons) in the catalyst effluent mixture (e.g., a concentration of species formed from the free radicals in a gas phase).

In an embodiment, the catalyzed reaction zone residence time can be from about 0.01 ms to about 3,500 ms, alternatively from about 0.025 ms to about 2,500 ms, alternatively from about 0.05 ms to about 1,500 ms, alternatively from about 0.075 ms to about 1,000 ms, alternatively from about 0.1 ms to about 500 ms, alternatively from about 0.25 ms to about 250 ms, alternatively from about 0.5 ms to about 225 ms, alternatively from about 1 ms to about 200 ms, alternatively from about 10 ms to about 175 ms, or alternatively from about 50 ms to about 150 ms.

In an embodiment, the catalyzed reaction zone can be a reactor wall comprising a catalyst coating, wherein a temperature can be at or above the temperature necessary to generate gas phase alkyl radicals (e.g., methyl radicals in the case of methane). In such embodiment, the catalyzed reaction zone residence time can be the residence time in a space (e.g., volume, region, etc.) that is at or above the temperature at which gas phase species can generate gas phase radicals. The catalyzed reaction zone residence time can be from about 0.01 ms to about 10 s, alternatively from about 0.05 ms to about 2 s, or alternatively from about 0.1 ms to about 1 s. As will be appreciated by one of skill in the art, and with the help of this disclosure, the catalyzed reaction zone residence time depends on the reactor design, process temperature, process pressure, and reactor dimensions.

In an embodiment, the catalyst bed can be heated such that a catalyst surface can be characterized by a catalyzed reaction zone temperature effective to achieve a desired conversion (e.g., methane conversion) and a desired concentration of free radicals in the catalyst effluent mixture. In such embodiment, the catalyzed reaction zone can be characterized by a catalyzed reaction zone residence time effective to achieve a desired conversion (e.g., methane conversion) and a desired concentration of free radicals in the catalyst effluent mixture.

In an embodiment, the catalyzed reaction zone can comprise a catalyst, wherein the catalyst catalyzes the non-oxidative coupling of $CH_4$ reaction (e.g., catalyst promotes the formation of free radicals from $CH_4$ and other hydrocarbons, for example a promoter such as ethane). In an embodiment, the catalyst can enable coupling of products, thereby changing a product mixture distribution (e.g., changing a composition of the product mixture), when compared to a product mixture produced in the absence of the catalyst in the catalyzed reaction zone. In another embodiment, the catalyst can enable both free radical generation and coupling of products.

In an embodiment, the catalysts suitable for use in the present disclosure can be supported catalysts and/or unsupported catalysts. In some embodiments, the supported catalyst can comprise a support, wherein the support can be catalytically active (e.g., the support can catalyze a non-oxidative coupling of $CH_4$ reaction; the support promotes the generation of free radicals; etc.). In other embodiments, the supported catalyst can comprise a support, wherein the support can be catalytically inactive (e.g., the support cannot catalyze a non-oxidative coupling of $CH_4$ reaction). In yet other embodiments, the supported catalyst can comprise a catalytically active support and a catalytically inactive support. Catalysts suitable for use in the present disclosure are described in more detail in U.S. Publication No. 20140336432 A1, which is incorporated by reference herein in its entirety.

In an embodiment, the catalyst can be characterized by a particle size of from about 10 nm to about 10 cm, alternatively from about 100 nm to about 1 cm, alternatively from about 500 nm to about 10 mm, alternatively from about 1 micron to about 1 mm, alternatively from about 10 microns to about 750 microns, or alternatively from about 50 microns to about 500 microns.

In an embodiment, the catalyst can comprise a catalytically active site attached via a single atom bond to a surface of a support particle in a catalyst bed; wherein the catalyst can be attached to an additional shaped support; and/or the catalyst can be attached to the reactor wall itself. In an embodiment, the catalyst can be characterized by small clusters or groupings of single metal atoms or a mixture of metal atoms consisting of metal or nonmetal atom dimers, metal or nonmetal atom trimers, larger nanostructures and/or nanoalloys of metals and/or nonmetals, or combinations thereof supported on a formed support and/or a reactor wall. The nanostructures and/or nanoalloys can contain a mixture of metals and nonmetals.

In an embodiment, the catalyst can comprise a metal oxide, wherein the metal oxide can be an oxide of a catalytically active metal.

In an embodiment, the catalyst can comprise a catalytically active metal, such as for example an alkali metal, an alkaline earth metal, a transition metal, and the like, or combinations thereof.

Nonlimiting examples of catalytically active metals suitable for use in the present disclosure include Li, Na, K, Mg, Al, B, Ca, Sr, Ba, Y, La, Ti, Zr, Ce, V, Nb, Ta, Cr, Mo, W, Re, Fe, Ru, Co, Rh, Ir, Ni, Pd, Pt, Cu, Zn, Ge, In, Sn, Pb, Bi, Mn, Pr, Nd, Pm, Sm, Eu, Gd, Tb, Dy, Ho, Er, Tm, Yb, alloys thereof, intermetallic alloys thereof, oxides thereof, carbides thereof, nitrides thereof, silicides thereof, silicates thereof, germanides thereof, germanates thereof, titanates thereof, zirconates thereof, phosphides thereof, and the like, or combinations thereof. In an embodiment, the catalytically active metal can comprise Li, K, Mg, Al, Ca, Sr, Ba, Ti, Ce, Mn, Zn, Co, Ni, Fe, alloys thereof, intermetallic alloys thereof, oxides thereof, carbides thereof, nitrides thereof, silicides thereof, silicates thereof, germanides thereof, germanates thereof, titanates thereof, zirconates thereof, phosphides thereof, and the like, or combinations thereof.

In an embodiment, the catalytically active metal can be present in the catalyst in an amount of from about 0.001 wt. % to about 10 wt. %, alternatively from about 0.01 wt. % to about 7.5 wt. %, or alternatively from about 0.1 wt. % to about 5 wt. %, based on the total weight of the catalyst.

In some embodiments, the catalyst can exclude silicon. In an embodiment, the catalyst can be substantially free of silicon, or alternatively essentially free of silicon. In an embodiment, the catalyst can comprise silicon in an amount of less than about 1 wt. %, alternatively less than about 0.5 wt. %, alternatively less than about 0.1 wt. %, alternatively less than about 0.01 wt. %, alternatively less than about 0.001 wt. %, or alternatively less than about 0.0001 wt. %.

In an embodiment, the catalyst can exclude silicon, and the catalytically active metal can comprise Li, Na, K, Mg, Al, B, Ca, Sr, Ba, Y, La, Ti, Zr, Ce, V, Nb, Ta, Cr, Mo, W, Re, Fe, Ru, Co, Rh, Ir, Ni, Pd, Pt, Cu, Zn, Ge, In, Sn, Pb, Bi, Mn, Pr, Nd, Pm, Sm, Eu, Gd, Tb, Dy, Ho, Er, Tm, Yb, alloys thereof, intermetallic alloys thereof, oxides thereof, carbides thereof, nitrides thereof, germanides thereof, germanates thereof, titanates thereof, zirconates thereof, phosphides thereof, and the like, or combinations thereof. In some embodiments, the catalytically active metals can comprise Ti, alloys thereof, intermetallic alloys thereof, oxides thereof, carbides thereof, nitrides thereof, germanides thereof, germanates thereof, titanates thereof, zirconates thereof, phosphides thereof, and the like, or combinations thereof.

In an embodiment, the catalytically active metals can be doped in a lattice of amorphous-molten-state materials made from one or more of B, Al, Si, Ti, Zr, and Ge bonded with one or more of C, N and O. In such embodiment, doping can be lattice doping, wherein dopant metals (e.g., catalytically active metals) can exchange with lattice elements in doped materials (e.g., doped silicon-based materials, doped titanium-based materials, doped zirconium-based materials, doped germanium-based materials, phosphorous-based materials, and the like, or combinations thereof), and the dopant metals can form or not form a specific chemical bonding (e.g., ionic bond) with other elements except for elements that were bonded to the lattice elements that were exchanged, which could lead to the dopant metals being confined in a lattice of doped materials, resulting in a specific catalytic performance. For purposes of the disclosure herein, the term "amorphous-molten-state material" refers to both the dopant metal and the doped materials (e.g., doped silicon-based materials, doped titanium-based materials, doped zirconium-based materials, doped germanium-based materials, phosphorous-based materials, and the like, or combinations thereof) being in a molten state or having a surface in a molten state during catalyst preparation, and then being formed into amorphous materials with long-range disorder and short-range order upon cooling.

In an embodiment, the dopant metals can be present in the catalyst in an amount of from about 0.001 wt. % to about 10 wt. %, alternatively from about 0.01 wt. % to about 7.5 wt. %, or alternatively from about 0.1 wt. % to about 5 wt. %, based on the total weight of the catalyst.

In an embodiment the catalyst can be prepared by using any suitable methodology, such as for example solid phase doping, chemical vapor deposition (CVD), vapor phase axial deposition (VAD), laser induced chemical vapor deposition (LCVD), doped sol-gel, porous Si compound impregnation, ion exchange, liquid phase deposition methods, mechanical alloying, wash coating methods, and the like, or combinations thereof.

In an embodiment, the catalyst can comprise a metal doped silicon-based material, a metal doped titanium-based material, a metal doped zirconium-based material, a metal doped germanium-based material, phosphorous-based materials, and the like, or combinations thereof; wherein a silicon-based material, a titanium-based material, a zirconium-based material, a germanium-based material, phosphorous-based materials, and the like, or combinations thereof can comprise one or more of O, C, and N. In such embodiment, the catalyst can be prepared by doping metal dopants in a lattice of the silicon-based material, the titanium-based material, the zirconium-based material, the germanium-based material, the phosphorous-based material, and the like, or combinations thereof; forming a molten material; and solidifying the molten material to form metal doped amorphous-molten-state materials (e.g., the metal doped silicon-based material, the metal doped titanium-based material, the metal doped zirconium-based material, the metal doped germanium-based material, the phosphorous-based material, and the like, or combinations thereof). Upon solidifying, the metal doped amorphous-molten-state materials can be subjected to grinding and/or molding.

In embodiments wherein the metal doped amorphous-molten-state materials are ground up, the resulting particle size of the metal doped amorphous-molten-state materials can be from about 10 nm to about 10 cm. As will be appreciated by one of skill in the art, and with the help of this disclosure, catalyst particles must provide a balance of active sites and low diffusional resistance and tortuosity, to allow for an optimal diffusional path length for reactants and generated radical species formed.

In embodiments wherein the metal doped amorphous-molten-state materials are molded, the metal doped amorphous-molten-state materials can be melted and then manufactured to obtain a specific shape (e.g., honeycomb-shaped monolithic catalyst), or it can be directly manufactured into a tubular reactor (without addition of a catalyst).

In an embodiment, metal dopant precursors can be used for doping metal dopants in the lattice of the silicon-based material, the titanium-based material, the zirconium-based material, the germanium-based material, the phosphorous-based material, and the like, or combinations thereof. Non-limiting examples of metal dopant precursors suitable for use in the present disclosure include elemental metals (e.g., catalytically active metals), nitrates thereof, halides thereof, sulfates thereof, carbonates thereof, hydroxides thereof, metal carbonyls, organometallic alkoxides having from 1 to 5 C atoms, organic acid salts having from 1 to 5 C atoms, and the like, or combinations thereof.

In an embodiment, a silicon source can be used for preparing silicon-based materials for doping with dopant metals. In such embodiment, the silicon source can comprise a liquid silicon source and/or a solid silicon source.

In an embodiment, the liquid silicon source can comprise tetraethyl silicates, silicon tetrachlorides, organic silane compounds, and the like, or combinations thereof. The organic silane compounds can be represented by Formula I and/or Formula II:

Formula I

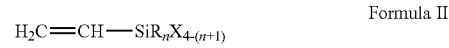

Formula II wherein n can be 0, 1 or 2; wherein R' can be represented by Formula III, Formula IV, Formula V, arylene, and the like:

Formula III wherein m can be 1 or equal to or greater than 3;

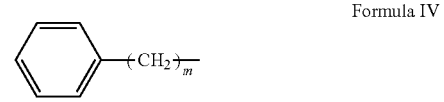

Formula IV wherein m can be 0, 1 or 2;

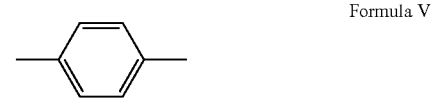

Formula V wherein R can be a hydroxyl group or a methyl group; wherein R" can be —Cl, —NH$_2$, —HNCH$_2$CH$_2$NH$_2$, —NHR$^1$, —N$_3$, —NCO, —SH, —CH—CH$_2$, —OCOCMe-CH$_2$, or a compound represented by Formula VI, Formula VII or Formula VIII:

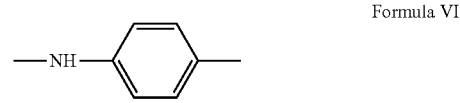

Formula VI

-continued

—OCH$_2$—HC—CH$_2$
\\O/     Formula VII

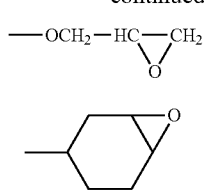
    Formula VIII wherein R$^1$ can be an alkyl group, an alkenyl group, or an aryl group, wherein R$^1$ can have from 1 to 5 C atoms; and wherein X can be a carbon-containing functional group which can be hydrolyzed or condensed, such as for example —Cl, —OMe, —OCH$_2$CH$_3$, —OCH$_2$CH$_2$OCH$_3$, or —OAc.

In an embodiment, the solid silicon source can comprise silica, silicon carbide, silicon nitride, elemental silicon. In an embodiment, the solid silicon source can be characterized by a solid silicon source particle size of from about 10 nm to about 200 microns. In an embodiment, the solid silicon source can be characterized by a solid silicon source specific surface area of from about 0.01 m$^2$/g to about 500 m$^2$/g.

For purposes of the disclosure herein, the metal doped amorphous-molten-state materials can be represented as A@SiO$_2$, A@SiC, A@Si$_3$N$_4$, A@SiC$_x$O$_y$ (4x+2y=4), A@SiO$_y$N$_z$ (2y+3z=4), A@SiC$_x$N$_z$ (4x+3z=4), A@SiC$_x$O$_y$N$_z$ (4x+2y+3z=4; x, y and z are not simultaneously equal to zero), wherein x can be from 0 to 1, y can be from 0 to 2, and z can be from 0 to 4/3, and wherein A represents the dopant metal(s).

In A@SiO$_2$, by partially or completely replacing Si atoms, metal element A is inserted in the lattice of silica (Si), and bonds with the adjacent O atoms (A-O). In A@SiC, by partially or completely replacing Si atoms, the metal element A is inserted in the lattice of silicon carbide (SiC), and bonds with the adjacent C or Si atoms (A-C or Si-A). In A@Si$_3$N$_4$, by partially or completely replacing Si atoms, the metal element A is inserted in the lattice of silicon nitride (Si$_3$N$_4$), and bonds with the adjacent N atoms (A-N). In A@SiC$_x$O$_y$, by partially or completely replacing Si or C atoms, the metal element A is inserted in the lattice of SiC$_x$O$_y$, and bonds with the adjacent C, O or Si atoms (A-C, A-O or A-Si). In A@SiO$_y$N$_z$, by partially or completely replacing Si or N atoms, the metal element A is inserted in the lattice of SiO$_y$N$_z$, and bonds with the adjacent N, O or Si atoms (A-N, A-O or A-Si). In A@SiC$_x$N$_z$, by partially or completely replacing Si or C atoms, the metal element A is inserted in the lattice of SiC$_x$N$_z$, and bonds with the adjacent C, N or Si atoms (A-C, A-N or A-Si). In A@SiC$_x$O$_y$N$_z$, by partially or completely replacing Si, N or C atoms, the metal element A is inserted in the lattice of SiC$_x$O$_y$N$_z$, and bonds with the adjacent C, N, O or Si atoms (A-C, A-O, A-N or A-Si). In some embodiments, A can include but is not limited to B, Al, Ti, Zr, Ge, and the like, or combinations thereof.

In some embodiments, the catalyst can further exclude a catalytically active metal. In an embodiment, the catalyst can be substantially free of catalytically active metal, or alternatively essentially free of catalytically active metal. In an embodiment, the catalyst can comprise a catalytically active metal in an amount of less than about 1 wt. %, alternatively less than about 0.5 wt. %, alternatively less than about 0.1 wt. %, alternatively less than about 0.01 wt. %, alternatively less than about 0.001 wt. %, or alternatively less than about 0.0001 wt. %.

In an embodiment, the catalyst can exclude a catalytically active metal, and the catalyst can comprise a silicon based material; Si bonded with one or more of C, N and O; silica; quartz, α-quartz, β-quartz; cristobalite; tridymite, α-tridymite, β-tridymite; silica glass; and the like; or combinations thereof.

In some embodiments, the catalyst can comprise monoliths (e.g., honeycombed, wall-filters, foams, etc.), wherein the monoliths can be made of high-temperature metals and/or ceramics (e.g., metals and/or ceramics that are characterized by a thermal stability of up to equal to or greater than about 900° C.).

In an embodiment, a method for producing C$_{2+}$ hydrocarbons and hydrogen can comprise reacting at least a portion of the primary effluent mixture in the secondary reaction zone to form a secondary effluent mixture comprising C$_{2+}$ hydrocarbons, hydrogen, free radicals, and unreacted methane. For purposes of the disclosure herein, the secondary reaction zone can also be referred to as "radical propagation zone," "thermal cracking zone," and/or "gas phase cracking zone." When the primary reaction zone is a catalyzed reaction zone, the secondary reaction zone can also be referred to as "uncatalyzed reaction zone."

In some embodiments, the secondary reaction zone can exclude a catalyst (e.g., uncatalyzed reaction zone). In other embodiments, the secondary reaction zone can comprise a catalyst, such as for example in a riser reactor.

In an embodiment, a method for producing C$_{2+}$ hydrocarbons and hydrogen can comprise heating the secondary reaction zone to a secondary reaction zone temperature. In an embodiment, the secondary reaction zone can be characterized by a secondary reaction zone temperature effective for propagating the non-oxidative coupling of CH$_4$ reaction, and/or for propagating reactions of ethane formed from the coupling of methyl radicals. Generally, the "propagation" refers to the free radicals reacting with stable molecules to form new free radicals, wherein the new free radicals go on to generate yet more free radicals, and so on. Propagation can involve hydrogen abstraction or addition of the radical to double bonds.

In an embodiment, the secondary reaction zone temperature can be equal to or greater than about 700° C., alternatively equal to or greater than about 800° C., alternatively equal to or greater than about 900° C., alternatively from about 700° C. to about 1,300° C., alternatively from about 800° C. to about 1,200° C., or alternatively from about 900° C. to about 1,100° C. In some embodiments, the secondary reaction zone temperature can be greater than the preheating temperature. In other embodiments, the secondary reaction zone temperature can be about the same as the primary reaction zone temperature. In yet other embodiments, the secondary reaction zone temperature can be lower than the primary reaction zone temperature. As will be appreciated by one of skill in the art, and with the help of this disclosure, the higher the secondary reaction zone temperature, the higher the probability that thermal cracking reactions would occur.

In an embodiment, the secondary reaction zone can be heated by using any suitable methodology, such as for example by external heat exchange, electric heating, electric arc heating, microwave heating, radiant heating produced by burning a portion of the reactant mixture with oxygen to directly heat the reactor, H$_2$ combustion, natural gas combustion, solar heating, infrared heating, microwave heating, thermally coupled exothermic reactions with an endothermic reaction (e.g., selective oxidation reactions coupled with the radical generation), isothermal pyrolysis wherein heat can be supplied through a reactor wall by resistance heating, and the like, or combinations thereof.

In some embodiments, the secondary reaction zone temperature can be non-uniform along a length of the secondary reaction zone. The secondary reaction zone temperature can be characterized by a gradient along the length of the secondary reaction zone. For example, the secondary reaction zone temperature can gradually decrease along the length between the primary reaction zone and the quench zone. The secondary reaction zone temperature can have any suitable temperature profile effective for achieving a desired conversion and selectivity.

In other embodiments, the secondary reaction zone temperature can be uniform along the length of the secondary reaction zone, e.g., the secondary reaction zone temperature can be substantially the same along the length of the secondary reaction zone.

In an embodiment, the secondary reaction zone can be characterized by a secondary reaction zone residence time. Generally, the secondary reaction zone residence time refers to the average amount of time that a compound such as methane (e.g., a molecule of that compound that does not undergo a chemical reaction in the secondary reaction zone) spends in that particular secondary reaction zone. In an embodiment, the secondary reaction zone can be characterized by a secondary reaction zone residence time effective for achieving a desired amount of species formed (such as $C_{2+}$ hydrocarbons) from the free radicals in the secondary effluent mixture (e.g., a concentration of species formed from the free radicals in a gas phase).

In an embodiment, the secondary reaction zone residence time can be from about 0.1 ms to about 10 s, alternatively from about 1 ms to about 8 s, alternatively from about 10 ms to about 5 s, alternatively from about 100 ms to about 2 s, or alternatively from about 250 ms to about 1 s. In some embodiments, the secondary reaction zone residence time can be greater than the primary reaction zone residence time.

In an embodiment, the primary reaction zone residence time and/or the secondary reaction zone residence time can be modified such that a desired concentration of free radicals can be achieved in the primary reaction zone and/or the secondary reaction zone, respectively.

In an embodiment, an amount of unreacted methane in the primary effluent mixture can be greater than an amount of unreacted methane in the secondary effluent mixture. As will be appreciated by one of skill in the art, and with the help of this disclosure, as a gas mixture travels along different zones of the reactor, subsequent thermal reactions will continue, and during reaction propagation in the secondary reaction zone, more alkane molecules will be engaged in the reaction, thereby causing a decrease in the amount of alkanes in the gas mixture present in and exiting the secondary reaction zone (e.g., secondary effluent mixture) when compared to the amount of alkanes in the gas mixture present in and exiting the primary reaction zone (e.g., primary effluent mixture).

In an embodiment, an amount of free radicals in the primary effluent mixture can be greater than an amount of free radicals in the secondary effluent mixture. As will be appreciated by one of skilled in the art, and with the help of this disclosure, free radicals in the secondary effluent mixture will almost instantaneously be converted to non-radical species once the secondary effluent mixture enters the quench zone, where the non-oxidative coupling of $CH_4$ reaction(s) stops.

In some embodiments, the secondary reaction zone temperature and/or the secondary reaction zone residence time can be modified such that a desired concentration in a specific component(s) can be achieved. For example, a shorter residence time and/or a lower temperature could maximize the formation of ethylene in the secondary reaction zone. Further, for example, a longer residence time could maximize the formation of aromatic hydrocarbons (e.g., benzene, naphthalene) in the secondary reaction zone. A secondary reaction zone temperature profile and/or the secondary reaction zone residence time can be set in such a manner that the propagation of the non-oxidative coupling of $CH_4$ reaction is driven to maximize the selectivity to either ethylene or aromatic hydrocarbons. Generally, aromatic hydrocarbons can be produced during the non-oxidative coupling of $CH_4$ by dehydroaromatization. Methane dehydroaromatization can include dehydrogenation and coupling of $CH_4$ to ethylene, which can then be consecutively oligomerized to benzene. Without wishing to be limited by theory, two methyl radicals can combine to form ethane ($C_2H_6$) via a strongly exothermic process, and $C_2H_6$ can undergo dehydrogenation readily, giving ethylene ($C_2H_4$) and hydrogen. Further, without wishing to be limited by theory, by abstraction of hydrogen from $C_2H_4$ (during the propagation of the non-oxidative coupling of $CH_4$ reaction) the resulting $.C_2H_3$ radical tends to react with additional $C_2H_4$ molecules, and further dehydrogenation and cyclization can lead to benzene ($C_6H_6$). Further, without wishing to be limited by theory, $C_6H_6$ can also be readily dehydrogenated by .H and, after further chain growth and cyclization, can yield the thermodynamically more stable naphthalene.

In other embodiments, hydrocracking to ethane or higher alkanes can occur in the secondary reaction zone. In such embodiments, selectivity and product distribution can depend on temperature and residence time. Ethane can be further dehydrogenated to ethylene, propane can be further dehydrogenated to propylene, etc. The hydrogen generated in the primary reaction zone can act as a diluent to the primary effluent mixture (e.g., reactive effluent produced in the primary reaction zone); inhibit dehydrogenation reactions; effectively increase selectivity to lighter hydrocarbons; depress formation of heavies and carbon; and the like; or combinations thereof. The effect of hydrogen depends on temperature, with hydrogen dilution becoming more important at higher reaction temperatures.

In an embodiment, a method for producing $C_{2+}$ hydrocarbons and hydrogen can comprise cooling at least a portion of the secondary effluent mixture in the quench zone to a quench temperature to yield a product mixture comprising $C_{2+}$ hydrocarbons, hydrogen and unreacted methane. As will be appreciated by one of skill in the art, and with the help of this disclosure, the secondary effluent mixture is cooled almost instantaneously upon entering the quench zone, and as such the non-oxidative coupling of $CH_4$ reaction does not proceed further in the quench zone.

In an embodiment, a method for producing $C_{2+}$ hydrocarbons and hydrogen can comprise cooling the quench zone to a quench temperature. In an embodiment, the quench zone can be characterized by a quench temperature effective for terminating or stopping the non-oxidative coupling of $CH_4$ reaction (e.g., terminating or stopping the propagation of the non-oxidative coupling of $CH_4$ reaction). Generally, chain termination can occur when two free radicals react with each other to form a stable, non-radical adduct, such as for example a hydrocarbon like ethane, benzene, naphthalene, etc.

In an embodiment, the quench temperature can be equal to or less than about 700° C., alternatively equal to or less than about 500° C., alternatively equal to or less than about 250° C., alternatively from about room temperature to about 700° C., alternatively from about 50° C. to about 500° C., or alternatively from about 100° C. to about 250° C. In an embodiment, the quench temperature can be lower than the secondary reaction zone temperature.

In an embodiment, the quench zone can be cooled by using any suitable methodology, such as for example by external heat exchange, external heat exchange to preheat the reactant mixture, removing supplied heat, removing heat, removing heat via an endothermic reaction (e.g., cracking of ethane, propane, or light naphtha to olefins, such as ethylene, propylene, etc.), expansive cooling (to remove kinetic energy), converting thermal energy into work by using a turbine for example, dilution, endothermic reactions (e.g., ethane dehydrogenation to ethylene), addition of $C_{2+}$ alkanes (e.g., ethane, propane, light naphtha, etc.), and the like, or combinations thereof. In an embodiment, the quench zone can be cooled by using a heat exchanger, wherein a design of the heat exchanger can include, without limitation, heat exchanger tubes that can be vertical or canted off vertical, filled or not filled with stacked inert spheres, wherein the inert spheres can increase the heat exchange between an effluent and heat transfer media. In some embodiments, reactor walls that define the quench zone or cooling zone can aid in transferring heat to a circulated coolant by serving as cooling fins, wherein the circulated coolant may or may not be under high pressure. In other embodiments, cooling passageways can include one or more channels in the quench zone. In yet other embodiments, the cooling passageways can include one or more tubes or generally hollow tunnels formed in the quench zone for flowing cooling fluid. The cooling passageways can be designed in a variety of orientations and can extend axially along the quench zone, radially though the quench zone, circumferentially about the quench zone, any other suitable orientation known in the art, and the like, or combinations thereof.

In an embodiment, the quench zone can be cooled by using heat exchangers placed in transfer lines for product effluents (e.g., secondary effluent mixture), and such heat exchangers can be referred to as "transfer-line exchangers." Such transfer-line exchangers can provide for a sudden drop (as rapidly as possible) in a temperature of effluent gases (e.g., secondary effluent mixture) to temperatures at which secondary reactions do not take place. An optimal temperature to which the secondary effluent mixture is lowered at an outlet of the quenching zone (e.g., quench temperature) can vary in accordance with a composition of the secondary effluent mixture. If the secondary effluent mixture contains certain levels of condensed polyaromatics, excessive fouling can occur if the quench temperature is dropped to a temperature too low below the optimal quench temperature. In such cases, the quench zone can be cooled in two stages comprising a first cooling stage and a second cooling stage, wherein the first cooling stage can be carried out by indirect quenching to a temperature of about 450-500° C., and wherein the second cooling stage can comprise direct cooling by introducing cold liquids into exchanger effluents.

In another embodiment, the quench zone can be cooled by spraying a quench fluid such as steam, water, oil, or liquid product into the quench zone; conveying through or into water, natural gas feed, or liquid products; preheating other streams; generating steam; expanding in a kinetic energy quench, such as a Joule Thompson expander, choke nozzle, or turbo expander; and the like, or combinations thereof. Using certain quench fluids can induce further chemical reactions to occur, creating additional reactive hydrocarbon products, increasing the overall energy and economic efficiency of the process, particularly when recovered or recycled streams from downstream processing streams are used as quench fluids.

In some embodiments, quenching can be accomplished in a single stage or step. In other embodiments, quenching can be accomplished in multiple stages by using different cooling means, cooling fluids, or both.

In an embodiment, the quench zone can be incorporated within the reactor, can comprise a separate vessel or device from the reactor, or both. A cooling system for the quench zone can incorporate various mechanisms known in the art to provide an optimum combination for highest operating efficiency.

In some embodiments, the quench temperature can be non-uniform along a length of the quench zone. The quench temperature can be characterized by a gradient along the length of the quench zone. For example, the quench temperature can gradually decrease along the length of the quench zone. The quench temperature can have any suitable temperature profile effective for achieving a desired conversion and selectivity.

In other embodiments, the quench temperature can be uniform along the length of the quench zone, e.g., the quench temperature can be substantially the same along the length of the quench zone.

In an embodiment, the quench zone can be characterized by a quench zone residence time. Generally, the quench zone residence time refers to the average amount of time that a compound such as ethylene (e.g., a molecule of that compound) spends in that particular quench zone. In an embodiment, the quench zone can be characterized by a quench zone residence time effective for achieving a desired temperature (e.g., quench temperature) for the product mixture exiting the reactor.

In an embodiment, the quench zone residence time can be from about 0.01 ms to about 10 s, alternatively from about 0.1 ms to about 9 s, alternatively from about 1 ms to about 7 s, alternatively from about 10 ms to about 5 s, or alternatively from about 10 ms to about 1 s.

In some embodiments, the reactor can be characterized by a substantially uniform inner diameter across its length, e.g., across all reactor zones (e.g., preheat zone, primary reaction zone, secondary reaction zone, quench zone). In other embodiments, the reactor can be characterized by a substantially uniform inner diameter across at least two reactor zones. For example, the inner diameter can be substantially the same in the preheat zone, the primary reaction zone, and the secondary reaction zone, and the inner diameter can be larger in the quench zone, for example to facilitate cooling. Inner diameters of each zone can have any values and profiles effective to achieve a desired conversion and/or selectivity. Further, inner diameters of a particular zone can be substantially uniform across each individual zone, or alternatively, the inner diameter of a particular zone can vary across a length of that particular zone.

In an embodiment, the reactor can be characterized by an inner diameter of from about 0.1 mm to about 5,000 mm, alternatively from about 15 mm to about 1,000 mm, or alternatively from about 25 mm to about 180 mm.

In an embodiment, the reactor can characterized by an inner diameter of from about 1 cm to about 200 cm, alternatively from about 5 cm to about 100, or alternatively from about 15 cm to about 30 cm.

In an embodiment, the reactor can be characterized by a length of from about 10 mm to about 100 m, alternatively from about 100 mm to about 75 m, alternatively from about 500 mm to about 60 m, alternatively from about 1 m to about 50 m, or alternatively from about 5 m to about 20 m.

In an embodiment, the preheat zone can be characterized by a length of from about 0.15 m to about 25 m, alternatively from about 0.3 m to about 10 m, or alternatively from about 0.5 m to about 5 m.

In an embodiment, the primary reaction zone can be characterized by a length of from about 0.025 m to about 2 m, alternatively from about 0.05 m to about 1.5 m, or alternatively from about 0.15 m to about 1 m.

In an embodiment, the secondary reaction zone can be characterized by a length of from about 0.15 m to about 5 m, alternatively from about 0.3 m to about 2 m, or alternatively from about 0.6 m to about 1.2 m.

In an embodiment, the quench zone can be characterized by a length of from about 0.05 m to about 5 m, alternatively from about 0.15 m to about 2.5 m, or alternatively from about 0.3 m to about 1 m.

In an embodiment, a converging-diverging nozzle can be used between any two reactor zones to help mixing a gas mixture flowing between the zones. For example, a converging-diverging nozzle can be used between the primary reaction zone and the secondary reaction zone. As another example, a converging-diverging nozzle can be used between the secondary reaction zone and the quench zone.

In an embodiment, the reactor can further comprise gas inlets along the length of the reactor, for optionally introducing a gas or gas mixture into the reactor in any of the reactor zones. For example, the reactor can comprise gas inlets in the primary reaction zone for allowing introducing hot gas into the reactor to create a supersonic hot gas stream for radical generation. As another example, the reactor can comprise gas inlets in the quench zone for allowing introducing cold gas into the reactor to cool the secondary effluent mixture entering the quench zone.

In an embodiment, the primary reaction zone can be placed outside the reactor, and a gas stream comprising a primary effluent mixture can be introduced into the reactor concentrically through gas inlets into the secondary reaction zone. In such embodiment, a stream of methane (e.g., preheated methane) can be flowing through the reactor and it can encounter the primary effluent mixture comprising free radicals in the secondary reaction zone.

In an embodiment, the reactant mixture comprising methane can be preheated outside the reactor and can be introduced into the reactor concentrically through gas inlets into the primary reaction zone. In such embodiment, the radicals can be generated by plasma in the primary reaction zone.

In some embodiments, the reactor can be characterized by a substantially uniform total pressure across its reactor zones (e.g., preheat zone, primary reaction zone, secondary reaction zone, quench zone). In other embodiments, the reactor can be characterized by a substantially uniform total pressure across at least two reactor zones. For example, the total pressure can be substantially the same in the preheat zone, the primary reaction zone, and the secondary reaction zone, and the total pressure can be lower in the quench zone, for example to facilitate cooling. Total pressure of each zone can have any values and profiles effective to achieve a desired conversion, selectivity, yield, etc.

In an embodiment, the reactor can be characterized by a total pressure of from about 0.1 bar to about 40 bar, alternatively from about 1 bar to about 20 bar, or alternatively from about 2 bar to about 10 bar.

As will be appreciated by one of skill in the art and with the help of this disclosure, each reactor zone contains a gas mixture, and each component of each gas mixture in each zone is characterized by a partial pressure. Further, as will be appreciated by one of skill in the art and with the help of this disclosure, partial pressures and the total pressure of each zone can be controlled to optimize yields. In an embodiment, each zone can be characterized by individual components partial pressures effective to achieve a desired conversion and/or selectivity. Further, as will be appreciated by one of skill in the art and with the help of this disclosure, each component partial pressure in each zone can be related to a concentration of that particular component in that particular zone.

In an embodiment, the primary reaction zone can be characterized by a free radical concentration and/or partial pressure (e.g., $.CH_3$ concentration and/or partial pressure, $.C_2H_5$ concentration and/or partial pressure, etc.) effective to achieve a desired conversion and/or selectivity. As will be appreciated by one of skill in the art and with the help of this disclosure, the higher the concentration of radicals in a particular zone, the smaller the dilution effect of $CH_4$.

In some embodiments, the catalyst bed can be heated such that a catalyst surface can be at an appropriate temperature and with an appropriate contact time to achieve a desired conversion and concentration of radicals in the primary effluent mixture, thereby achieving a desired overall conversion.

In an embodiment, the secondary reaction zone can be characterized by a free radical concentration and/or partial pressure (e.g., $.CH_3$ concentration and/or partial pressure, $.C_2H_5$ concentration and/or partial pressure, etc.) effective to achieve a desired conversion and/or selectivity.

In an embodiment, the reactor can be characterized by a gas hourly space velocity (GHSV) of from about 1,000 $h^{-1}$ to about 500,000 $h^{-1}$, alternatively from about 1,500 $h^{-1}$ to about 100,000 $h^{-1}$, alternatively from about 2,000 $h^{-1}$ to about 50,000 $h^{-1}$, or alternatively from about 4,000 $h^{-1}$ to about 25,000 $h^{-1}$. Generally, the GHSV relates a reactant (e.g., reactant mixture) gas flow rate to a reactor volume. GHSV is usually measured at standard temperature and pressure. In an embodiment, the reactor can be characterized by a GHSV (or GHSV profile) effective to achieve a desired conversion and/or selectivity.

In an embodiment, the reactor can be characterized by a weight hourly space velocity (WHSV) of from about 1,000 $h^{-1}$ to about 500,000 $h^{-1}$, alternatively from about 1,500 $h^{-1}$ to about 100,000 $h^{-1}$ alternatively from about 2,000 $h^{-1}$ to about 50,000 $h^{-1}$, or alternatively from about 4,000 $h^{-1}$ to about 25,000 $h^{-1}$. In such embodiment, the reactor comprises a catalyst. Generally, the WHSV refers to a mass of reagents fed per hour divided by a mass of catalyst used in a particular reactor. In an embodiment, the reactor can be characterized by a WHSV (or WHSV profile) effective to achieve a desired conversion and/or selectivity.

In some embodiments, at least a portion of the reactor can be characterized by a laminar flow. In such embodiments, the at least a portion of reactor can be characterized by a GHSV of from about 1,000 $h^{-1}$ to about 500,000 $h^{-1}$, alternatively from about 1,500 $h^{-1}$ to about 100,000 $h^{-1}$, alternatively from about 2,000 $h^{-1}$ to about 50,000 $h^{-1}$, or alternatively from about 4,000 $h^{-1}$ to about 25,000 $h^{-1}$.

In other embodiments, at least a portion of the reactor can be characterized by a turbulent flow. In such embodiments, the at least a portion of reactor can be characterized by a GHSV of from about 1,000 $h^{-1}$ to about 500,000 $h^{-1}$, alternatively from about 1,500 $h^{-1}$ to about 100,000 $h^{-1}$, alternatively from about 2,000 $h^{-1}$ to about 50,000 $h^{-1}$, or alternatively from about 4,000 $h^{-1}$ to about 25,000 $h^{-1}$.

In yet other embodiments, at least one portion of one reactor zone can be characterized by a laminar flow and at least one portion of one reactor zone can be characterized by a turbulent flow.

In an embodiment, the primary reaction zone and the secondary reaction zone can be characterized by a laminar flow. In some embodiments, the laminar flow could be ensured by the use of monolith (e.g., honeycomb monolith) catalysts in the primary reaction zone. In an embodiment, the reactor can be characterized by a flow profile (e.g., laminar and/or turbulent flow) effective to achieve a desired conversion and/or selectivity.

As will be appreciated by one of skill in the art and with the help of this disclosure, due to high temperatures required for this process, optimal process designs can be achieved in which this novel reactor design would be integrated into chemical producing processes where the energy integration is optimized in the context of the process.

In an embodiment, the catalyst and the reactor can be part of an integrated design (e.g., integrated catalyst-reactor) comprising a reactor shell that may include a single layer of material; a single composite structure; multiple reactor shells with one or more shells positioned within one or more of the other shells; or combinations thereof. The reactor shell can include various zones, components and/or modules. The reactor shell of the integrated catalyst-reactor for catalytic pyrolysis of hydrocarbons can comprise a zone (e.g., region) for gas phase cracking of higher alkanes formed from the coupling of the alkyl radicals that are formed on a catalytic surface and then desorbed into the gas phase. In some embodiments, an outer layer of the reactor shell can provide structural support and/or allow for managing the heat transport of the process. The reactor shell can be stable under the process conditions as disclosed herein. The reactor shell may have inner layers containing catalytically active sites and/or for resisting deterioration due to operating conditions in a reactor chamber.

In an embodiment, the reactor shell can comprises an outer shell comprising a superalloy, duplex stainless steel, super duplex stainless steel, nickel-based high temperature low creep superalloy (e.g., INCONEL 718 alloy, which is an austenite nickel-chromium based superalloy), and the like, or combinations thereof.

In an embodiment, the reactor shell can comprise an inner shell consisting of a carbide, a nitride, titanium diboride, a sialon ceramic, zirconia, thoria, a carbon-carbon composite, tungsten, tantalum, molybdenium, chromium, nickel, and the like, alloys thereof, or combinations thereof. In some configurations, an inner reactor shell can be coated with an aluminum carbide coating that can provide resistance to carburization and creep.

In an embodiment, the reactor shell can comprise an inner coating. The inner coating can be applied by using any suitable coating process, including but not limited to pack cementation process (CVD), gas phase coating (CVD), thermal spraying, plasma spraying, gas phase coating, physical vapor deposition, and the like, or combinations thereof. In some configurations, the inner coating can comprise nickel aluminide, wherein near surface regions of the coating can be enriched with aluminum. In other configurations, the inner coating can comprise silica and/or modified silica comprising catalytically active sites. In yet other configurations, the inner coating can comprise zirconia and/or modified zirconia containing catalytically active sites.

In an embodiment, alkane (e.g., methane) conversion and product selectivity can be modulated by controlling radical chain reactions of alkyl (e.g., methyl, ethyl, etc.) radicals in a stream of alkane(s) by controlling reactor configuration (e.g., design) and/or process parameters, such as for example partial pressures of free radicals, residence time, heat flux, temperature profiles, gas mixtures compositions, rate of quenching in the secondary reaction zone, etc.

In an embodiment, the primary effluent mixture can comprise free radicals. By generating a flow of radicals in front of a heated empty zone (e.g., secondary reaction zone), final product selectivity can be controlled by controlling the residence time and temperature profile of the secondary reaction zone where the radical propagation occurs.

In embodiments where the primary reaction zone comprises a catalyst, conversion and product selectivity can be affected by catalyst composition, feed (e.g., reactant mixture) composition, preheating temperature, catalyst surface temperature, contact time with the catalyst bed, intra-particle and inter-particle mass and heat transfer, secondary reaction zone temperature, temperature profile of the secondary reaction zone, secondary reaction zone residence time, rate of quenching, etc.

In an embodiment, a methane conversion can be from about 1% to about 85%, alternatively from about 10% to about 60%, or alternatively from about 20% to about 50%. Generally, a conversion of a reagent or reactant refers to the percentage (usually mol %) of reagent that reacted to both undesired and desired products, based on the total amount (e.g., moles) of reagent present before any reaction took place. For purposes of the disclosure herein, the conversion of a reagent is a % conversion based on moles converted. For example, the methane conversion can be calculated by using equation (1):

$$CH_4 \text{ conversion} = \frac{C_{CH_4}^{in} - C_{CH_4}^{out}}{C_{CH_4}^{in}} \times 100\% \qquad (1)$$

wherein $C^{in}_{CH_4}$=number of moles of carbon (C) from $CH_4$ that entered the reactor as part of the reactant mixture; and $C^{out}_{CH_4}$=number of moles of C from $CH_4$ that was recovered from the reactor as part of the product mixture.

In an embodiment, the product mixture comprises $C_{2+}$ hydrocarbons, wherein the $C_{2+}$ hydrocarbons can comprise ethylene, ethane, acetylene, propylene, propane, aromatic hydrocarbons (e.g., benzene, substituted benzenes, naphthalene), and the like, or combinations thereof. In an embodiment, the $C_{2+}$ hydrocarbons can further comprise acetylene, $C_3$-$C_6$ hydrocarbons, alkyl-benzenes, polycyclic aromatic hydrocarbons, and the like, or combinations thereof.

Generally, a selectivity to a desired product or products refers to how much desired product was formed divided by the total products formed, both desired and undesired. For purposes of the disclosure herein, the selectivity to a desired product is a % selectivity based on moles converted into the desired product. Further, for purposes of the disclosure herein, a C, selectivity (e.g., $C_{2+}$ selectivity, $C_{2=}$ selectivity, etc.) can be calculated by dividing a number of moles of carbon (C) from $CH_4$ that were converted into the desired product by the total number of moles of C from $CH_4$ that were converted, which can be calculated as $C^{in}_{CH_4}$-$C^{out}_{CH_4}$=number of moles of C from $CH_4$ that were converted into $C_2H_4$; $C_{C6H6}$=number of moles of C from $CH_4$ that were converted into $C_6H_6$; $C_{C10H8}$=number of moles of C from $CH_4$ that were converted into $C_{10}H_8$; etc.

In an embodiment, a $C_{2+}$ selectivity (e.g., selectivity to $C_{2+}$ hydrocarbons) refers to the number of moles of C of $C_{2+}$ hydrocarbons that were formed divided by the total number of moles of C from CH$_4$ that were converted. For example, the C$_{2+}$ selectivity can be calculated by using equation (2):

$$C_{2+} \text{ selectivity} = \frac{\text{moles of C of C}_{2+} \text{ hydrocarbons formed}}{C_{CH_4}^{in} - C_{CH_4}^{out}} \times 100\% \quad (2)$$

In an embodiment, the C$_{2+}$ selectivity (e.g., selectivity to C$_{2+}$ hydrocarbons) can be from about 5% to about 100%, alternatively from about 20% to about 100%, or alternatively from about 50% to about 100%.

In an embodiment, a selectivity to ethylene (C$_{2=}$ selectivity) can be from about 2% to about 85%, alternatively from about 10% to about 65%, or alternatively from about 15% to about 50%. For example, the selectivity to ethylene can be calculated by using equation (3):

$$C_{2=} \text{ selectivity} = \frac{\text{moles of C of C}_2\text{H}_4 \text{ formed}}{C_{CH_4}^{in} - C_{CH_4}^{out}} \times 100\% \quad (3)$$

In an embodiment, a selectivity to benzene (C$_6$H$_6$ selectivity) can be from about 0.0% to about 60%, alternatively from about 5% to about 40%, or alternatively from about 15% to about 30%. For example, the selectivity to benzene can be calculated by using equation (4):

$$C_6H_6 \text{ selectivity} = \frac{\text{moles of C of C}_6\text{H}_6 \text{ formed}}{C_{CH_4}^{in} - C_{CH_4}^{out}} \times 100\% \quad (4)$$

In an embodiment, a selectivity to naphthalene (C$_{10}$H$_8$ selectivity) can be from about 0.0% to about 60%, alternatively from about 5% to about 40%, or alternatively from about 15% to about 30%. For example, the selectivity to naphthalene can be calculated by using equation (5):

$$C_{10}H_8 \text{ selectivity} = \frac{\text{moles of C of C}_{10}\text{H}_8 \text{ formed}}{C_{CH_4}^{in} - C_{CH_4}^{out}} \times 100\% \quad (5)$$

In an embodiment, a selectivity to aromatic hydrocarbons (AH selectivity) can be from about 0% to about 95%, alternatively from about 5% to about 60%, or alternatively from about 20% to about 50%. For example, the selectivity to AH can be calculated by using equation (6):

$$AH \text{ selectivity} = \frac{\text{moles of C of AH formed}}{C_{CH_4}^{in} - C_{CH_4}^{out}} \times 100\% \quad (6)$$

In an embodiment, a selectivity to hydrogen (H$_2$ selectivity) can be from about 40% to about 100%, alternatively from about 60% to about 100%, or alternatively from about 80% to about 100%. For example, the selectivity to hydrogen can be calculated by using equation (7):

$$H_2 \text{ selectivity} = \frac{\text{moles of H of H}_2 \text{ formed}}{4 \times (C_{CH_4}^{in} - C_{CH_4}^{out})} \times 100\% \quad (7)$$

In an embodiment, a method for producing C$_{2+}$ hydrocarbons and hydrogen can comprise recovering at least a portion of the product mixture from the reactor.

In an embodiment, the product mixture can comprise at least a portion of unreacted methane and optional diluent. In such embodiments, at least a portion of the diluent can be separated from the product mixture to yield a recovered diluent. The diluent can be separated from the product mixture by using any suitable separation technique. In an embodiment, at least a portion of the diluent can be separated from the product mixture by distillation. In an embodiment, at least a portion of the recovered diluent can be recycled to the reactant mixture.

In an embodiment, at least a portion of the unreacted methane can be separated from the product mixture to yield recovered methane. Methane can be separated from the product mixture by using any suitable separation technique, such as for example distillation (e.g., cryogenic distillation), pressure swing adsorption, temperature swing adsorption, selective membranes, and the like, or combinations thereof. In an embodiment, at least a portion of the recovered methane can be recycled to the reactant mixture.

In an embodiment, at least a portion of the C$_{2+}$ hydrocarbons can be separated from the product mixture to yield recovered C$_{2+}$ hydrocarbons. The C$_{2+}$ hydrocarbons can be separated from the product mixture by using any suitable separation technique. In an embodiment, at least a portion of the C$_{2+}$ hydrocarbons can be separated from the product mixture by distillation (e.g., cryogenic distillation), pressure swing adsorption, temperature swing adsorption, selective membranes, and the like, or combinations thereof.

In some embodiments, at least a portion of ethylene can be separated from the product mixture by using any suitable separation technique (e.g., distillation), pressure swing adsorption, temperature swing adsorption, selective membranes, and the like, or combinations thereof.

In some embodiments, at least a portion of H$_2$ can be separated from the product mixture to yield recovered hydrogen by using any suitable separation technique (e.g., distillation), pressure swing adsorption, temperature swing adsorption, selective membranes, and the like, or combinations thereof. The recovered hydrogen can be used in other processes such as for example hydrogenations, hydrocracking processes, hydrotreating processes, etc.

In some embodiments, at least a portion of the aromatic hydrocarbons (e.g., benzene, naphthalene) can be separated from the product mixture by using any suitable separation technique, such as for example distillation, flashing tank adsorption, scrubbing with any suitable liquid or solvent to absorb and separate aromatic hydrocarbons from light hydrocarbons, and the like, or combinations thereof.

In some embodiments, the product mixture can be fed into a stream cracker separation stream and the recovered gases can be further used in other processes.

Referring to the embodiment of FIG. 3, a method for producing C$_{2+}$ hydrocarbons and hydrogen can comprise (a) introducing a reactant mixture to a reactor, wherein the reactant mixture comprises methane (CH$_4$), wherein the reactor comprises a preheat zone, a catalyzed reaction zone (e.g., a primary reaction zone comprising a catalyst bed), an uncatalyzed reaction zone (e.g., a secondary reaction zone), and a quench zone, and wherein the catalyzed reaction zone comprises a catalyst comprising quartz pieces, such as for example chips, beads, rings, quartz felt, quartz wool, coated quartz, modified quartz, and the like, or combinations thereof; (b) heating the reactant mixture (Q1$_{in}$) to a preheating temperature of less than about 700° C. in the preheat zone to yield a heated reactant mixture; (c) contacting at least a portion of the heated reactant mixture with the catalyst in the catalyzed reaction zone to form a catalyst effluent mixture comprising free radicals, hydrocarbons, hydrogen and unreacted methane, wherein the catalyzed reaction zone is characterized by a catalyzed reaction zone temperature ($Q2_{in}$) of from about 900° C. to about 1,150° C. and by a catalyzed reaction zone residence time; (d) reacting at least a portion of the catalyst effluent mixture in the uncatalyzed reaction zone to form a reaction zone effluent mixture comprising $C_{2+}$ hydrocarbons, hydrogen, free radicals, and unreacted methane, wherein the uncatalyzed reaction zone is characterized by an uncatalyzed reaction zone temperature ($Q3_{in}$) of from about 900° C. to about 1,150° C. and by an uncatalyzed reaction zone residence time, wherein the uncatalyzed reaction zone residence time is at least 5 times greater than the catalyzed reaction zone residence time; (e) cooling at least a portion of the reaction zone effluent mixture ($Q4_{out}$) in the quench zone to a quench temperature to yield a product mixture comprising $C_{2+}$ hydrocarbons, hydrogen, and unreacted methane, wherein the quench temperature is lower than the uncatalyzed reaction zone temperature; and (f) recovering at least a portion of the product mixture from the reactor. In an embodiment, the quartz pieces can have a size of from about 10 nm to about 10 cm. In such embodiment, the formation of coke is minimized. In an embodiment, the main hydrocarbon formed in the catalyzed reaction zone can be ethane, and ethane can be converted to the desired product(s), such as ethylene and benzene, in the uncatalyzed reaction zone. In an embodiment, the product mixture can comprise benzene, wherein at least a portion of benzene can be separated from the product mixture by distillation. The $C_{2+}$ hydrocarbons can comprise ethylene, wherein at least a portion of ethylene can be separated from the product mixture by cryogenic distillation. In an embodiment, the reactant mixture can further comprise ethane or a higher hydrocarbon as a promoter, wherein the promoter can "jump start" the radical formation process in the catalyzed reaction zone. For purposes of the disclosure herein, "Qi" (e.g., Q1, Q2, Q3, Q4) refers to the heat transfer between the reactor and its surrounding medium, such as for example a heat exchanger. A positive Qi going "in" represents that heat is being transferred to that particular reactor zone, e.g., that particular reactor zone is being heated. For example, $Q1_{in}$ in FIG. 3 indicates that heat is being transferred into the preheat zone, e.g., the preheat zone is being heated. A positive Qi going "out" represents that heat is being transferred from that particular reactor zone, e.g., that particular reactor zone is being cooled. For example, $Q4_{out}$ in FIG. 3 indicates that heat is being transferred from the quench zone, e.g., the quench zone is being cooled. A negative Qi going "in" represents that heat is being transferred from that particular reactor zone, e.g., that particular reactor zone is being cooled. For example, $-Q4_{in}$ in FIGS. 4A-H indicates that heat is being transferred from the quench zone, e.g., the quench zone is being cooled.

In an embodiment, a method for producing $C_{2+}$ hydrocarbons and hydrogen can comprise (a) introducing a reactant mixture to a reactor, wherein the reactant mixture comprises methane ($CH_4$), wherein the reactor comprises a preheat zone, a catalyzed reaction zone, an uncatalyzed reaction zone, and a quench zone, and wherein the catalyzed reaction zone comprises a catalyst comprising monoliths (e.g., honeycombed, wall-filters, foams, etc.) made of high temperature ceramics or metals; (b) heating the reactant mixture to a preheating temperature of less than about 700° C. in the preheat zone to yield a heated reactant mixture; (c) contacting at least a portion of the heated reactant mixture with the catalyst in the catalyzed reaction zone to form a catalyst effluent mixture comprising free radicals, $C_{2+}$ hydrocarbons, hydrogen and unreacted methane, wherein the catalyzed reaction zone is characterized by a catalyzed reaction zone temperature of from about 900° C. to about 1,150° C. and by a catalyzed reaction zone residence time of from about 50 ms to about 150 ms; (d) reacting at least a portion of the catalyst effluent mixture in the uncatalyzed reaction zone to form a reaction zone effluent mixture comprising $C_{2+}$ hydrocarbons, hydrogen, free radicals, and unreacted methane, wherein the uncatalyzed reaction zone is characterized by an uncatalyzed reaction zone temperature of from about 900° C. to about 1,150° C. and by an uncatalyzed reaction zone residence time, wherein the uncatalyzed reaction zone residence time is at least 5 times greater than the catalyzed reaction zone residence time; (e) expansive cooling at least a portion of the reaction zone effluent mixture in the quench zone to a quench temperature to yield a product mixture comprising $C_{2+}$ hydrocarbons, hydrogen, and unreacted methane, wherein the quench temperature is lower than the uncatalyzed reaction zone temperature; and (f) recovering at least a portion of the product mixture from the reactor. In such embodiment, a converging-diverging nozzle can be used between any two zones to help mixing.

In an embodiment, a method for producing $C_{2+}$ hydrocarbons and hydrogen can comprise (a) introducing a reactant mixture to a reactor, wherein the reactant mixture comprises methane ($CH_4$), and wherein the reactor comprises a preheat zone, a primary reaction zone, a secondary reaction zone, and a quench zone; (b) heating the reactant mixture to a preheating temperature in the preheat zone to yield a heated reactant mixture; (c) generating free radicals in at least a portion of the heated reactant mixture in the primary reaction zone by using a dielectric barrier discharge to form a primary effluent mixture comprising free radicals, $C_{2+}$ hydrocarbons, hydrogen, and unreacted methane, wherein conversion of the reactant mixture (e.g., methane, ethane, etc.) to free radicals is strongly dependent on discharge power; (d) reacting at least a portion of the primary effluent mixture in the secondary reaction zone to form a secondary effluent mixture comprising $C_{2+}$ hydrocarbons, hydrogen, free radicals, and unreacted methane, wherein the secondary reaction zone is characterized by a secondary reaction zone temperature, wherein the secondary reaction zone temperature is greater than the preheating temperature, wherein an amount of unreacted methane in the primary effluent mixture is greater than an amount of unreacted methane in the secondary effluent mixture, and wherein an amount of free radicals in the primary effluent mixture is greater than an amount of free radicals in the secondary effluent mixture; (e) cooling at least a portion of the secondary effluent mixture in the quench zone to a quench temperature to yield a product mixture comprising $C_{2+}$ hydrocarbons, hydrogen and unreacted methane, wherein the quench temperature is lower than the secondary reaction zone temperature; and (f) recovering at least a portion of the product mixture from the reactor. In such embodiment, conversion and selectivity are dependent on process conditions and reactor design, such as for example temperature profile of each zone, residence time of each zone, concentration of reactive species (e.g., free radicals) to propagate to give the desired product selectivity and feed conversion.

Referring to the embodiments of FIGS. 4A-4H, schematics of reactor designs are displayed, wherein the reactor comprises a preheat zone, a primary reaction zone comprising a catalyst (e.g., catalytic reaction zone), a secondary reaction zone, and a quench zone, indicating heat input (Qi). In such embodiments, temperatures, residence times, pressures, flow dynamics and mixing characteristics, reactor diameter and lengths of each of the four zones could have different values to optimize each zone and the reactor could be of singular construction (same reactor could comprise all four zones) or could comprise different types of reactors for at least two of the zones.

Figure 4A:
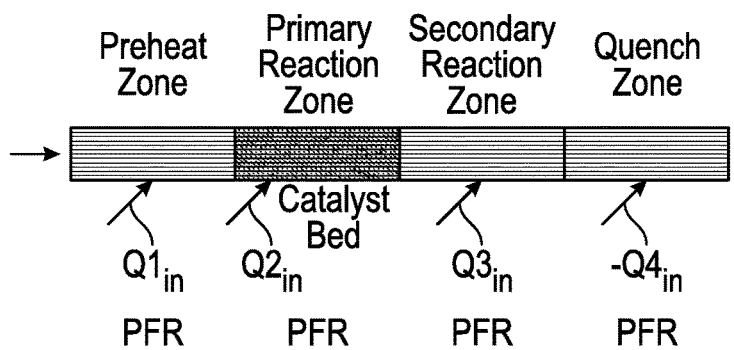
FIGS. 4A-4H display schematics of reactor designs comprising a preheat zone, a primary reaction zone comprising a catalyst, a secondary reaction zone, and a quench zone, indicating heat input (Qi) and reactor type per zone.

Referring to the embodiment of FIG. 4A, a method for producing $C_{2+}$ hydrocarbons and hydrogen can comprise (a) introducing a reactant mixture to a reactor, wherein the reactant mixture comprises methane ($CH_4$), wherein the reactor comprises a preheat zone, a catalyzed reaction zone (e.g., a primary reaction zone comprising a catalyst bed), an uncatalyzed reaction zone (e.g., a secondary reaction zone), and a quench zone; (b) heating the reactant mixture ($Q1_{in}$) to a preheating temperature in the preheat zone to yield a heated reactant mixture; wherein the preheat zone comprises a PFR; wherein the preheat zone is designed to minimize a radial temperature gradient, to minimize compositional and/or flow gradients of the heated reactant mixture reaching the catalyzed reactor zone in the reactor, to minimize energy input, and the like, or combinations thereof; wherein the preheat zone comprises a preheater, wherein the preheater is designed to minimize a pressure drop across the preheat zone, to maximize heat transfer to the reactant mixture, to minimize energy input, to optimize flow of the heated reactant mixture into the catalyzed reaction zone, and the like, or combinations thereof; and wherein a design of the preheat zone and/or a design of the preheater can depend on a design of the catalyzed reaction zone for required heat, mass transfer, fluid dynamics, and the like, or combinations thereof; (c) contacting at least a portion of the heated reactant mixture with the catalyst bed in the catalyzed reaction zone to form a catalyst effluent mixture comprising free radicals, hydrocarbons, hydrogen and unreacted methane; wherein the catalyzed reaction zone is characterized by a catalyzed reaction zone temperature; wherein the catalyzed reaction zone is heated to the catalyzed reaction zone temperature ($Q2_{in}$); wherein the catalyzed reaction zone temperature is greater than the preheating temperature; wherein the catalyzed reaction zone comprises a PFR; wherein the catalyzed reaction zone is designed to optimize heat transfer to the catalyst, to minimize energy costs, to maximize mass transfer of reactants to catalytic sites, to maximize mass transfer of products away from the catalytic sites, and the like, or combinations thereof; wherein the catalyst comprises particles, and wherein flow rates are optimized to maximize intra-particle and/or inter-particle mass transfer based on a stream composition; wherein heat transfer is optimized to maintain a desired temperature at a catalyst surface and/or in a gas phase within the catalyzed reaction zone, while minimizing energy input; and wherein the catalyzed reaction zone can be optionally designed to optimize catalyzed reaction zone conditions along a length of the catalyzed reaction zone as a composition of the gas phase changes due to conversion of reactants, wherein the catalyzed reaction zone conditions comprise variable catalyst formulation (e.g., catalyst composition, catalyst particle size, catalyst particle form, etc.), temperature, flow rate, mixing, fluid dynamics, staged addition of desired feeds and/or additives, and the like, or combinations thereof; (d) reacting at least a portion of the catalyst effluent mixture in the uncatalyzed reaction zone to form a reaction zone effluent mixture comprising $C_{2+}$ hydrocarbons, hydrogen, free radicals, and unreacted methane; wherein the uncatalyzed reaction zone is characterized by an uncatalyzed reaction zone temperature; wherein the uncatalyzed reaction zone is heated to the uncatalyzed reaction zone temperature ($Q3_{in}$); wherein the uncatalyzed reaction zone comprises a PFR; wherein the uncatalyzed reaction zone is designed to optimize process conditions in the uncatalyzed reaction zone to obtain desired product yields while minimizing energy input, wherein the process conditions comprise temperature, temperature gradients, residence time, pressure, mixing and/or fluid dynamics, and the like, or combinations thereof; wherein gas phase reactions and/or reactions with reactor walls are optimized to obtain desired product yields; and wherein the uncatalyzed reaction zone is designed to optimize mixing in any staged addition of additives and/or agents that promote a desired production of $C_{2+}$ hydrocarbons and/or aromatic hydrocarbons, and/or limited formation of polycyclic aromatics and coke; (e) cooling at least a portion of the reaction zone effluent mixture ($-Q4_{in}$) in the quench zone to a quench temperature to yield a product mixture comprising $C_{2+}$ hydrocarbons, hydrogen, and unreacted methane; wherein the quench temperature is lower than the uncatalyzed reaction zone temperature; wherein the quench zone comprises a PFR; and wherein the quench zone is designed to optimize heat transfer to the reaction zone effluent mixture, to optimize quenching quickly and uniformly, while recovering high quality energy from the quench zone, and the like, or combinations thereof; and (f) recovering at least a portion of the product mixture from the reactor. In some embodiments of FIG. 4A, the quench zone can comprise an inner reactor wall comprising quench zone structures (e.g., fins) to increase heat removal. In other embodiments of FIG. 4A, the quench zone can comprise stacks and/or strings of particulates (e.g., spheres, ovals, etc.) to increase turbulence, thereby increasing heat transfer within the quench zone. In yet other embodiments of FIG. 4A, a quenching fluid (e.g., quenching agent, water, steam, etc.) can be introduced into the quench zone by using any suitable methodology, such as for example by using spray bars.

Figure 4B:
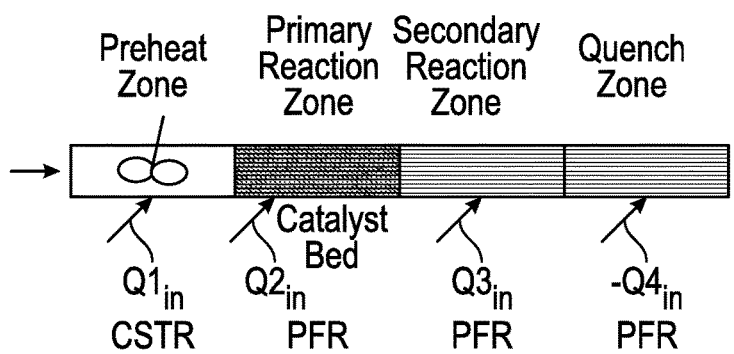

Referring to the embodiment of FIG. 4B, a method for producing $C_{2+}$ hydrocarbons and hydrogen can comprise (a) introducing a reactant mixture to a reactor, wherein the reactant mixture comprises methane ($CH_4$), wherein the reactor comprises a preheat zone, a catalyzed reaction zone (e.g., a primary reaction zone comprising a catalyst bed), an uncatalyzed reaction zone (e.g., a secondary reaction zone), and a quench zone; (b) heating the reactant mixture ($Q1_{in}$) to a preheating temperature in the preheat zone to yield a heated reactant mixture; wherein the preheat zone comprises a CSTR; wherein the preheat zone is designed to minimize a radial temperature gradient, to minimize compositional and/or flow gradients of the heated reactant mixture reaching the catalyzed reactor zone in the reactor, to minimize energy input, and the like, or combinations thereof; wherein the preheat zone comprises a preheater, wherein the preheater is designed to minimize a pressure drop across the preheat zone, to maximize heat transfer to the reactant mixture, to minimize energy input, to optimize flow of the heated reactant mixture into the catalyzed reaction zone, and the like, or combinations thereof; and wherein a design of the preheat zone and/or a design of the preheater can depend on a design of the catalyzed reaction zone for required heat, mass transfer, fluid dynamics, and the like, or combinations thereof; (c) contacting at least a portion of the heated reactant mixture with the catalyst bed in the catalyzed reaction zone to form a catalyst effluent mixture comprising free radicals, hydrocarbons, hydrogen and unreacted methane; wherein the catalyzed reaction zone is characterized by a catalyzed reaction zone temperature; wherein the catalyzed reaction zone is heated to the catalyzed reaction zone temperature ($Q2_{in}$); wherein the catalyzed reaction zone temperature is greater than the preheating temperature; wherein the catalyzed reaction zone comprises a PFR; wherein the catalyzed reaction zone is designed to optimize heat transfer to the catalyst, to minimize energy costs, to maximize mass transfer of reactants to catalytic sites, to maximize mass transfer of products away from the catalytic sites, and the like, or combinations thereof; wherein the catalyst comprises particles, and wherein flow rates are optimized to maximize intra-particle and/or inter-particle mass transfer based on a stream composition; wherein heat transfer is optimized to maintain a desired temperature at a catalyst surface and/or in a gas phase within the catalyzed reaction zone, while minimizing energy input; and wherein the catalyzed reaction zone can be optionally designed to optimize catalyzed reaction zone conditions along a length of the catalyzed reaction zone as a composition of the gas phase changes due to conversion of reactants, wherein the catalyzed reaction zone conditions comprise variable catalyst formulation (e.g., catalyst composition, catalyst particle size, catalyst particle form, etc.), temperature, flow rate, mixing, fluid dynamics, staged addition of desired feeds and/or additives, and the like, or combinations thereof; (d) reacting at least a portion of the catalyst effluent mixture in the uncatalyzed reaction zone to form a reaction zone effluent mixture comprising $C_{2+}$ hydrocarbons, hydrogen, free radicals, and unreacted methane; wherein the uncatalyzed reaction zone is characterized by an uncatalyzed reaction zone temperature; wherein the uncatalyzed reaction zone is heated to the uncatalyzed reaction zone temperature ($Q3_{in}$); wherein the uncatalyzed reaction zone comprises a PFR; wherein the uncatalyzed reaction zone is designed to optimize process conditions in the uncatalyzed reaction zone to obtain desired product yields while minimizing energy input, wherein the process conditions comprise temperature, temperature gradients, residence time, pressure, mixing and/or fluid dynamics, and the like, or combinations thereof; wherein gas phase reactions and/or reactions with reactor walls are optimized to obtain desired product yields; and wherein the uncatalyzed reaction zone is designed to optimize mixing in any staged addition of additives and/or agents that promote a desired production of $C_{2+}$ hydrocarbons and/or aromatic hydrocarbons, and/or limited formation of polycyclic aromatics and coke; (e) cooling at least a portion of the reaction zone effluent mixture ($-Q4_{in}$) in the quench zone to a quench temperature to yield a product mixture comprising $C_{2+}$ hydrocarbons, hydrogen, and unreacted methane; wherein the quench temperature is lower than the uncatalyzed reaction zone temperature; wherein the quench zone comprises a PFR; and wherein the quench zone is designed to optimize heat transfer to the reaction zone effluent mixture, to optimize quenching quickly and uniformly, while recovering high quality energy from the quench zone, and the like, or combinations thereof; and (f) recovering at least a portion of the product mixture from the reactor. In some embodiments of FIG. 4B, the quench zone can comprise an inner reactor wall comprising quench zone structures (e.g., fins) to increase heat removal. In other embodiments of FIG. 4B, the quench zone can comprise stacks and/or strings of particulates (e.g., spheres, ovals, etc.) to increase turbulence, thereby increasing heat transfer within the quench zone. In yet other embodiments of FIG. 4B, a quenching fluid (e.g., quenching agent, water, steam, etc.) can be introduced into the quench zone by using any suitable methodology, such as for example by using spray bars.

Figure 4C:
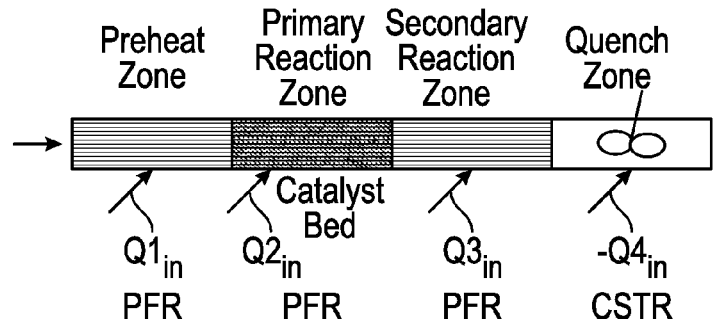

Referring to the embodiment of FIG. 4C, a method for producing $C_{2+}$ hydrocarbons and hydrogen can comprise (a) introducing a reactant mixture to a reactor, wherein the reactant mixture comprises methane ($CH_4$), wherein the reactor comprises a preheat zone, a catalyzed reaction zone (e.g., a primary reaction zone comprising a catalyst bed), an uncatalyzed reaction zone (e.g., a secondary reaction zone), and a quench zone; (b) heating the reactant mixture ($Q1_{in}$) to a preheating temperature in the preheat zone to yield a heated reactant mixture; wherein the preheat zone comprises a PFR; wherein the preheat zone is designed to minimize a radial temperature gradient, to minimize compositional and/or flow gradients of the heated reactant mixture reaching the catalyzed reactor zone in the reactor, to minimize energy input, and the like, or combinations thereof; wherein the preheat zone comprises a preheater, wherein the preheater is designed to minimize a pressure drop across the preheat zone, to maximize heat transfer to the reactant mixture, to minimize energy input, to optimize flow of the heated reactant mixture into the catalyzed reaction zone, and the like, or combinations thereof; and wherein a design of the preheat zone and/or a design of the preheater can depend on a design of the catalyzed reaction zone for required heat, mass transfer, fluid dynamics, and the like, or combinations thereof; (c) contacting at least a portion of the heated reactant mixture with the catalyst bed in the catalyzed reaction zone to form a catalyst effluent mixture comprising free radicals, hydrocarbons, hydrogen and unreacted methane; wherein the catalyzed reaction zone is characterized by a catalyzed reaction zone temperature; wherein the catalyzed reaction zone is heated to the catalyzed reaction zone temperature ($Q2_{in}$); wherein the catalyzed reaction zone temperature is greater than the preheating temperature; wherein the catalyzed reaction zone comprises a PFR; wherein the catalyzed reaction zone is designed to optimize heat transfer to the catalyst, to minimize energy costs, to maximize mass transfer of reactants to catalytic sites, to maximize mass transfer of products away from the catalytic sites, and the like, or combinations thereof; wherein the catalyst comprises particles, and wherein flow rates are optimized to maximize intra-particle and/or inter-particle mass transfer based on a stream composition; wherein heat transfer is optimized to maintain a desired temperature at a catalyst surface and/or in a gas phase within the catalyzed reaction zone, while minimizing energy input; and wherein the catalyzed reaction zone can be optionally designed to optimize catalyzed reaction zone conditions along a length of the catalyzed reaction zone as a composition of the gas phase changes due to conversion of reactants, wherein the catalyzed reaction zone conditions comprise variable catalyst formulation (e.g., catalyst composition, catalyst particle size, catalyst particle form, etc.), temperature, flow rate, mixing, fluid dynamics, staged addition of desired feeds and/or additives, and the like, or combinations thereof; (d) reacting at least a portion of the catalyst effluent mixture in the uncatalyzed reaction zone to form a reaction zone effluent mixture comprising $C_{2+}$ hydrocarbons, hydrogen, free radicals, and unreacted methane; wherein the uncatalyzed reaction zone is characterized by an uncatalyzed reaction zone temperature; wherein the uncatalyzed reaction zone is heated to the uncatalyzed reaction zone temperature ($Q3_{in}$); wherein the uncatalyzed reaction zone comprises a PFR; wherein the uncatalyzed reaction zone is designed to optimize process conditions in the uncatalyzed reaction zone to obtain desired product yields while minimizing energy input, wherein the process conditions comprise temperature, temperature gradients, residence time, pressure, mixing and/or fluid dynamics, and the like, or combinations thereof; wherein gas phase reactions and/or reactions with reactor walls are optimized to obtain desired product yields; and wherein the uncatalyzed reaction zone is designed to optimize mixing in any staged addition of additives and/or agents that promote a desired production of $C_{2+}$ hydrocarbons and/or aromatic hydrocarbons, and/or limited formation of polycyclic aromatics and coke; (e) cooling at least a portion of the reaction zone effluent mixture ($-Q4_{in}$) in the quench zone to a quench temperature to yield a product mixture comprising $C_{2+}$ hydrocarbons, hydrogen, and unreacted methane; wherein the quench temperature is lower than the uncatalyzed reaction zone temperature; wherein the quench zone comprises a CSTR; and wherein the quench zone is designed to optimize heat transfer to the reaction zone effluent mixture, to optimize quenching quickly and uniformly, while recovering high quality energy from the quench zone, and the like, or combinations thereof; and (f) recovering at least a portion of the product mixture from the reactor. In some embodiments of FIG. 4C, the quench zone can comprise an inner reactor wall comprising quench zone structures (e.g., fins) to increase heat removal. In other embodiments of FIG. 4C, the quench zone can comprise stacks and/or strings of particulates (e.g., spheres, ovals, etc.) to increase turbulence, thereby increasing heat transfer within the quench zone. In yet other embodiments of FIG. 4C, a quenching fluid (e.g., quenching agent, water, steam, etc.) can be introduced into the quench zone by using any suitable methodology, such as for example by using spray bars.

Figure 4D:
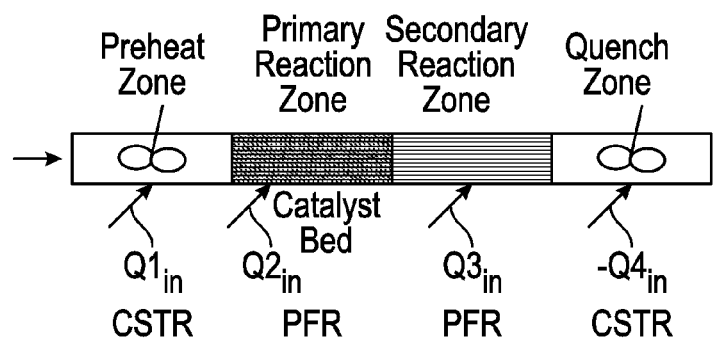

Referring to the embodiment of FIG. 4D, a method for producing $C_{2+}$ hydrocarbons and hydrogen can comprise (a) introducing a reactant mixture to a reactor, wherein the reactant mixture comprises methane ($CH_4$), wherein the reactor comprises a preheat zone, a catalyzed reaction zone (e.g., a primary reaction zone comprising a catalyst bed), an uncatalyzed reaction zone (e.g., a secondary reaction zone), and a quench zone; (b) heating the reactant mixture ($Q1_{in}$) to a preheating temperature in the preheat zone to yield a heated reactant mixture; wherein the preheat zone comprises a CSTR; wherein the preheat zone is designed to minimize a radial temperature gradient, to minimize compositional and/or flow gradients of the heated reactant mixture reaching the catalyzed reactor zone in the reactor, to minimize energy input, and the like, or combinations thereof; wherein the preheat zone comprises a preheater, wherein the preheater is designed to minimize a pressure drop across the preheat zone, to maximize heat transfer to the reactant mixture, to minimize energy input, to optimize flow of the heated reactant mixture into the catalyzed reaction zone, and the like, or combinations thereof; and wherein a design of the preheat zone and/or a design of the preheater can depend on a design of the catalyzed reaction zone for required heat, mass transfer, fluid dynamics, and the like, or combinations thereof; (c) contacting at least a portion of the heated reactant mixture with the catalyst bed in the catalyzed reaction zone to form a catalyst effluent mixture comprising free radicals, hydrocarbons, hydrogen and unreacted methane; wherein the catalyzed reaction zone is characterized by a catalyzed reaction zone temperature; wherein the catalyzed reaction zone is heated to the catalyzed reaction zone temperature ($Q2_{in}$); wherein the catalyzed reaction zone temperature is greater than the preheating temperature; wherein the catalyzed reaction zone comprises a PFR; wherein the catalyzed reaction zone is designed to optimize heat transfer to the catalyst, to minimize energy costs, to maximize mass transfer of reactants to catalytic sites, to maximize mass transfer of products away from the catalytic sites, and the like, or combinations thereof; wherein the catalyst comprises particles, and wherein flow rates are optimized to maximize intra-particle and/or inter-particle mass transfer based on a stream composition; wherein heat transfer is optimized to maintain a desired temperature at a catalyst surface and/or in a gas phase within the catalyzed reaction zone, while minimizing energy input; and wherein the catalyzed reaction zone can be optionally designed to optimize catalyzed reaction zone conditions along a length of the catalyzed reaction zone as a composition of the gas phase changes due to conversion of reactants, wherein the catalyzed reaction zone conditions comprise variable catalyst formulation (e.g., catalyst composition, catalyst particle size, catalyst particle form, etc.), temperature, flow rate, mixing, fluid dynamics, staged addition of desired feeds and/or additives, and the like, or combinations thereof; (d) reacting at least a portion of the catalyst effluent mixture in the uncatalyzed reaction zone to form a reaction zone effluent mixture comprising $C_{2+}$ hydrocarbons, hydrogen, free radicals, and unreacted methane; wherein the uncatalyzed reaction zone is characterized by an uncatalyzed reaction zone temperature; wherein the uncatalyzed reaction zone is heated to the uncatalyzed reaction zone temperature ($Q3_{in}$); wherein the uncatalyzed reaction zone comprises a PFR; wherein the uncatalyzed reaction zone is designed to optimize process conditions in the uncatalyzed reaction zone to obtain desired product yields while minimizing energy input, wherein the process conditions comprise temperature, temperature gradients, residence time, pressure, mixing and/or fluid dynamics, and the like, or combinations thereof; wherein gas phase reactions and/or reactions with reactor walls are optimized to obtain desired product yields; and wherein the uncatalyzed reaction zone is designed to optimize mixing in any staged addition of additives and/or agents that promote a desired production of $C_{2+}$ hydrocarbons and/or aromatic hydrocarbons, and/or limited formation of polycyclic aromatics and coke; (e) cooling at least a portion of the reaction zone effluent mixture ($-Q4_{in}$) in the quench zone to a quench temperature to yield a product mixture comprising $C_{2+}$ hydrocarbons, hydrogen, and unreacted methane; wherein the quench temperature is lower than the uncatalyzed reaction zone temperature, and wherein the quench zone comprises a CSTR; and wherein the quench zone is designed to optimize heat transfer to the reaction zone effluent mixture, to optimize quenching quickly and uniformly, while recovering high quality energy from the quench zone, and the like, or combinations thereof; and (f) recovering at least a portion of the product mixture from the reactor. In some embodiments of FIG. 4D, the quench zone can comprise an inner reactor wall comprising quench zone structures (e.g., fins) to increase heat removal. In other embodiments of FIG. 4D, the quench zone can comprise stacks and/or strings of particulates (e.g., spheres, ovals, etc.) to increase turbulence, thereby increasing heat transfer within the quench zone. In yet other embodiments of FIG. 4D, a quenching fluid (e.g., quenching agent, water, steam, etc.) can be introduced into the quench zone by using any suitable methodology, such as for example by using spray bars.

Figure 4E:
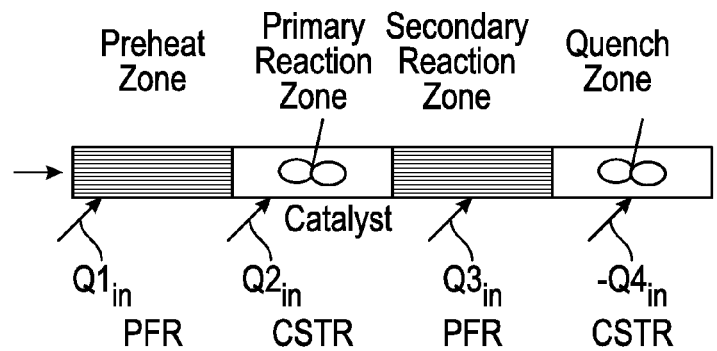

Referring to the embodiment of FIG. 4E, a method for producing $C_{2+}$ hydrocarbons and hydrogen can comprise (a) introducing a reactant mixture to a reactor, wherein the reactant mixture comprises methane ($CH_4$), wherein the reactor comprises a preheat zone, a catalyzed reaction zone (e.g., a primary reaction zone comprising a catalyst), an uncatalyzed reaction zone (e.g., a secondary reaction zone), and a quench zone; (b) heating the reactant mixture ($Q1_{in}$) to a preheating temperature in the preheat zone to yield a heated reactant mixture; wherein the preheat zone comprises a PFR; wherein the preheat zone is designed to minimize a radial temperature gradient, to minimize compositional and/or flow gradients of the heated reactant mixture reaching the catalyzed reactor zone in the reactor, to minimize energy input, and the like, or combinations thereof; wherein the preheat zone comprises a preheater, wherein the preheater is designed to minimize a pressure drop across the preheat zone, to maximize heat transfer to the reactant mixture, to minimize energy input, to optimize flow of the heated reactant mixture into the catalyzed reaction zone, and the like, or combinations thereof; and wherein a design of the preheat zone and/or a design of the preheater can depend on a design of the catalyzed reaction zone for required heat, mass transfer, fluid dynamics, and the like, or combinations thereof; (c) contacting at least a portion of the heated reactant mixture with the catalyst in the catalyzed reaction zone to form a catalyst effluent mixture comprising free radicals, hydrocarbons, hydrogen and unreacted methane; wherein the catalyzed reaction zone is characterized by a catalyzed reaction zone temperature; wherein the catalyzed reaction zone is heated to the catalyzed reaction zone temperature ($Q2_{in}$); wherein the catalyzed reaction zone temperature is greater than the preheating temperature; wherein the catalyzed reaction zone comprises a CSTR; wherein the catalyzed reaction zone is designed to optimize heat transfer to the catalyst, to minimize energy costs, to maximize mass transfer of reactants to catalytic sites, to maximize mass transfer of products away from the catalytic sites, and the like, or combinations thereof; wherein the catalyst comprises particles, and wherein flow rates are optimized to maximize intra-particle and/or inter-particle mass transfer based on a stream composition; wherein heat transfer is optimized to maintain a desired temperature at a catalyst surface and/or in a gas phase within the catalyzed reaction zone, while minimizing energy input; and wherein the catalyzed reaction zone can be optionally designed to optimize catalyzed reaction zone conditions along a length of the catalyzed reaction zone as a composition of the gas phase changes due to conversion of reactants, wherein the catalyzed reaction zone conditions comprise variable catalyst formulation (e.g., catalyst composition, catalyst particle size, catalyst particle form, etc.), temperature, flow rate, mixing, fluid dynamics, staged addition of desired feeds and/or additives, and the like, or combinations thereof; (d) reacting at least a portion of the catalyst effluent mixture in the uncatalyzed reaction zone to form a reaction zone effluent mixture comprising $C_{2+}$ hydrocarbons, hydrogen, free radicals, and unreacted methane; wherein the uncatalyzed reaction zone is characterized by an uncatalyzed reaction zone temperature; wherein the uncatalyzed reaction zone is heated to the uncatalyzed reaction zone temperature ($Q3_{in}$); wherein the uncatalyzed reaction zone comprises a PFR; wherein the uncatalyzed reaction zone is designed to optimize process conditions in the uncatalyzed reaction zone to obtain desired product yields while minimizing energy input, wherein the process conditions comprise temperature, temperature gradients, residence time, pressure, mixing and/or fluid dynamics, and the like, or combinations thereof; wherein gas phase reactions and/or reactions with reactor walls are optimized to obtain desired product yields; and wherein the uncatalyzed reaction zone is designed to optimize mixing in any staged addition of additives and/or agents that promote a desired production of $C_{2+}$ hydrocarbons and/or aromatic hydrocarbons, and/or limited formation of polycyclic aromatics and coke; (e) cooling at least a portion of the reaction zone effluent mixture ($-Q4_{in}$) in the quench zone to a quench temperature to yield a product mixture comprising $C_{2+}$ hydrocarbons, hydrogen, and unreacted methane, wherein the quench temperature is lower than the uncatalyzed reaction zone temperature, and wherein the quench zone comprises a CSTR; and wherein the quench zone is designed to optimize heat transfer to the reaction zone effluent mixture, to optimize quenching quickly and uniformly, while recovering high quality energy from the quench zone, and the like, or combinations thereof; and (f) recovering at least a portion of the product mixture from the reactor. In some embodiments of FIG. 4E, the quench zone can comprise an inner reactor wall comprising quench zone structures (e.g., fins) to increase heat removal. In other embodiments of FIG. 4E, the quench zone can comprise stacks and/or strings of particulates (e.g., spheres, ovals, etc.) to increase turbulence, thereby increasing heat transfer within the quench zone. In yet other embodiments of FIG. 4E, a quenching fluid (e.g., quenching agent, water, steam, etc.) can be introduced into the quench zone by using any suitable methodology, such as for example by using spray bars.

Figure 4F:
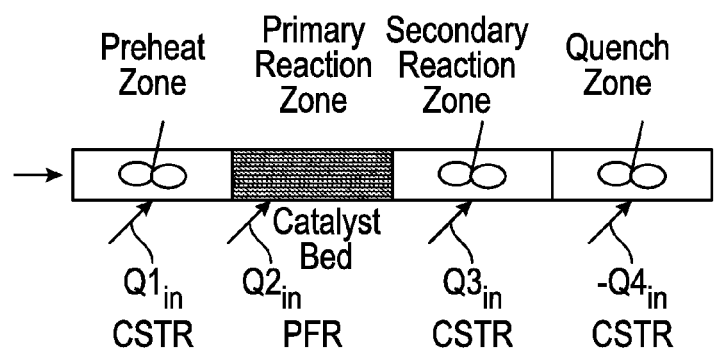

Referring to the embodiment of FIG. 4F, a method for producing $C_{2+}$ hydrocarbons and hydrogen can comprise (a) introducing a reactant mixture to a reactor, wherein the reactant mixture comprises methane ($CH_4$), wherein the reactor comprises a preheat zone, a catalyzed reaction zone (e.g., a primary reaction zone comprising a catalyst bed), an uncatalyzed reaction zone (e.g., a secondary reaction zone), and a quench zone; (b) heating the reactant mixture ($Q1_{in}$) to a preheating temperature in the preheat zone to yield a heated reactant mixture; wherein the preheat zone comprises a CSTR; wherein the preheat zone is designed to minimize a radial temperature gradient, to minimize compositional and/or flow gradients of the heated reactant mixture reaching the catalyzed reactor zone in the reactor, to minimize energy input, and the like, or combinations thereof; wherein the preheat zone comprises a preheater, wherein the preheater is designed to minimize a pressure drop across the preheat zone, to maximize heat transfer to the reactant mixture, to minimize energy input, to optimize flow of the heated reactant mixture into the catalyzed reaction zone, and the like, or combinations thereof; and wherein a design of the preheat zone and/or a design of the preheater can depend on a design of the catalyzed reaction zone for required heat, mass transfer, fluid dynamics, and the like, or combinations thereof; (c) contacting at least a portion of the heated reactant mixture with the catalyst bed in the catalyzed reaction zone to form a catalyst effluent mixture comprising free radicals, hydrocarbons, hydrogen and unreacted methane; wherein the catalyzed reaction zone is characterized by a catalyzed reaction zone temperature; wherein the catalyzed reaction zone is heated to the catalyzed reaction zone temperature ($Q2_{in}$); wherein the catalyzed reaction zone temperature is greater than the preheating temperature; wherein the catalyzed reaction zone comprises a PFR; wherein the catalyzed reaction zone is designed to optimize heat transfer to the catalyst, to minimize energy costs, to maximize mass transfer of reactants to catalytic sites, to maximize mass transfer of products away from the catalytic sites, and the like, or combinations thereof; wherein the catalyst comprises particles, and wherein flow rates are optimized to maximize intra-particle and/or inter-particle mass transfer based on a stream composition; wherein heat transfer is optimized to maintain a desired temperature at a catalyst surface and/or in a gas phase within the catalyzed reaction zone, while minimizing energy input; and wherein the catalyzed reaction zone can be optionally designed to optimize catalyzed reaction zone conditions along a length of the catalyzed reaction zone as a composition of the gas phase changes due to conversion of reactants, wherein the catalyzed reaction zone conditions comprise variable catalyst formulation (e.g., catalyst composition, catalyst particle size, catalyst particle form, etc.), temperature, flow rate, mixing, fluid dynamics, staged addition of desired feeds and/or additives, and the like, or combinations thereof; (d) reacting at least a portion of the catalyst effluent mixture in the uncatalyzed reaction zone to form a reaction zone effluent mixture comprising $C_{2+}$ hydrocarbons, hydrogen, free radicals, and unreacted methane; wherein the uncatalyzed reaction zone is characterized by an uncatalyzed reaction zone temperature; wherein the uncatalyzed reaction zone is heated to the uncatalyzed reaction zone temperature ($Q3_{in}$); wherein the uncatalyzed reaction zone comprises a CSTR; wherein the uncatalyzed reaction zone is designed to optimize process conditions in the uncatalyzed reaction zone to obtain desired product yields while minimizing energy input, wherein the process conditions comprise temperature, temperature gradients, residence time, pressure, mixing and/or fluid dynamics, and the like, or combinations thereof; wherein gas phase reactions and/or reactions with reactor walls are optimized to obtain desired product yields; and wherein the uncatalyzed reaction zone is designed to optimize mixing in any staged addition of additives and/or agents that promote a desired production of $C_{2+}$ hydrocarbons and/or aromatic hydrocarbons, and/or limited formation of polycyclic aromatics and coke; (e) cooling at least a portion of the reaction zone effluent mixture ($-Q4_{in}$) in the quench zone to a quench temperature to yield a product mixture comprising $C_{2+}$ hydrocarbons, hydrogen, and unreacted methane, wherein the quench temperature is lower than the uncatalyzed reaction zone temperature, and wherein the quench zone comprises a CSTR; and wherein the quench zone is designed to optimize heat transfer to the reaction zone effluent mixture, to optimize quenching quickly and uniformly, while recovering high quality energy from the quench zone, and the like, or combinations thereof; and (f) recovering at least a portion of the product mixture from the reactor. In some embodiments of FIG. 4F, the quench zone can comprise an inner reactor wall comprising quench zone structures (e.g., fins) to increase heat removal. In other embodiments of FIG. 4F, the quench zone can comprise stacks and/or strings of particulates (e.g., spheres, ovals, etc.) to increase turbulence, thereby increasing heat transfer within the quench zone. In yet other embodiments of FIG. 4F, a quenching fluid (e.g., quenching agent, water, steam, etc.) can be introduced into the quench zone by using any suitable methodology, such as for example by using spray bars.

Figure 4G:
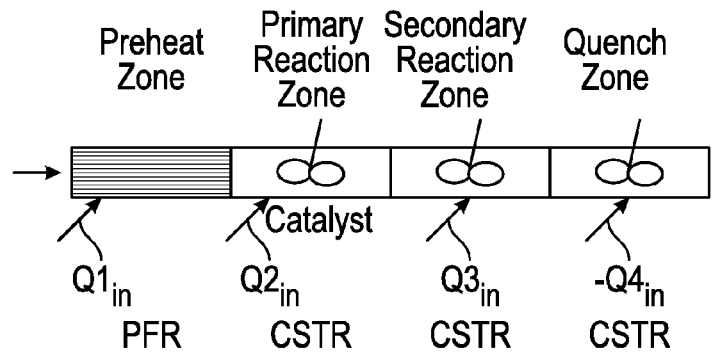

Referring to the embodiment of FIG. 4G, a method for producing $C_{2+}$ hydrocarbons and hydrogen can comprise (a) introducing a reactant mixture to a reactor, wherein the reactant mixture comprises methane ($CH_4$), wherein the reactor comprises a preheat zone, a catalyzed reaction zone (e.g., a primary reaction zone comprising a catalyst), an uncatalyzed reaction zone (e.g., a secondary reaction zone), and a quench zone; (b) heating the reactant mixture ($Q1_{in}$) to a preheating temperature in the preheat zone to yield a heated reactant mixture; wherein the preheat zone comprises a PFR; wherein the preheat zone is designed to minimize a radial temperature gradient, to minimize compositional and/or flow gradients of the heated reactant mixture reaching the catalyzed reactor zone in the reactor, to minimize energy input, and the like, or combinations thereof; wherein the preheat zone comprises a preheater, wherein the preheater is designed to minimize a pressure drop across the preheat zone, to maximize heat transfer to the reactant mixture, to minimize energy input, to optimize flow of the heated reactant mixture into the catalyzed reaction zone, and the like, or combinations thereof; and wherein a design of the preheat zone and/or a design of the preheater can depend on a design of the catalyzed reaction zone for required heat, mass transfer, fluid dynamics, and the like, or combinations thereof; (c) contacting at least a portion of the heated reactant mixture with the catalyst in the catalyzed reaction zone to form a catalyst effluent mixture comprising free radicals, hydrocarbons, hydrogen and unreacted methane; wherein the catalyzed reaction zone is characterized by a catalyzed reaction zone temperature; wherein the catalyzed reaction zone is heated to the catalyzed reaction zone temperature ($Q2_{in}$); wherein the catalyzed reaction zone temperature is greater than the preheating temperature; wherein the catalyzed reaction zone comprises a CSTR; wherein the catalyzed reaction zone is designed to optimize heat transfer to the catalyst, to minimize energy costs, to maximize mass transfer of reactants to catalytic sites, to maximize mass transfer of products away from the catalytic sites, and the like, or combinations thereof; wherein the catalyst comprises particles, and wherein flow rates are optimized to maximize intra-particle and/or inter-particle mass transfer based on a stream composition; wherein heat transfer is optimized to maintain a desired temperature at a catalyst surface and/or in a gas phase within the catalyzed reaction zone, while minimizing energy input; and wherein the catalyzed reaction zone can be optionally designed to optimize catalyzed reaction zone conditions along a length of the catalyzed reaction zone as a composition of the gas phase changes due to conversion of reactants, wherein the catalyzed reaction zone conditions comprise variable catalyst formulation (e.g., catalyst composition, catalyst particle size, catalyst particle form, etc.), temperature, flow rate, mixing, fluid dynamics, staged addition of desired feeds and/or additives, and the like, or combinations thereof; (d) reacting at least a portion of the catalyst effluent mixture in the uncatalyzed reaction zone to form a reaction zone effluent mixture comprising $C_{2+}$ hydrocarbons, hydrogen, free radicals, and unreacted methane; wherein the uncatalyzed reaction zone is characterized by an uncatalyzed reaction zone temperature; wherein the uncatalyzed reaction zone is heated to the uncatalyzed reaction zone temperature ($Q3_{in}$); wherein the uncatalyzed reaction zone comprises a CSTR; wherein the uncatalyzed reaction zone is designed to optimize process conditions in the uncatalyzed reaction zone to obtain desired product yields while minimizing energy input, wherein the process conditions comprise temperature, temperature gradients, residence time, pressure, mixing and/or fluid dynamics, and the like, or combinations thereof; wherein gas phase reactions and/or reactions with reactor walls are optimized to obtain desired product yields; and wherein the uncatalyzed reaction zone is designed to optimize mixing in any staged addition of additives and/or agents that promote a desired production of $C_{2+}$ hydrocarbons and/or aromatic hydrocarbons, and/or limited formation of polycyclic aromatics and coke; (e) cooling at least a portion of the reaction zone effluent mixture ($-Q4_{in}$) in the quench zone to a quench temperature to yield a product mixture comprising $C_{2+}$ hydrocarbons, hydrogen, and unreacted methane, wherein the quench temperature is lower than the uncatalyzed reaction zone temperature, and wherein the quench zone comprises a CSTR; and wherein the quench zone is designed to optimize heat transfer to the reaction zone effluent mixture, to optimize quenching quickly and uniformly, while recovering high quality energy from the quench zone, and the like, or combinations thereof; and (f) recovering at least a portion of the product mixture from the reactor. In some embodiments of FIG. 4G, the quench zone can comprise an inner reactor wall comprising quench zone structures (e.g., fins) to increase heat removal. In other embodiments of FIG. 4G, the quench zone can comprise stacks and/or strings of particulates (e.g., spheres, ovals, etc.) to increase turbulence, thereby increasing heat transfer within the quench zone. In yet other embodiments of FIG. 4G, a quenching fluid (e.g., quenching agent, water, steam, etc.) can be introduced into the quench zone by using any suitable methodology, such as for example by using spray bars.

Figure 4H:
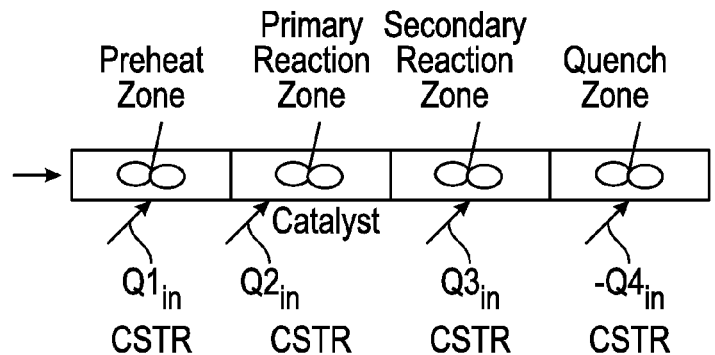

Referring to the embodiment of FIG. 4H, a method for producing $C_{2+}$ hydrocarbons and hydrogen can comprise (a) introducing a reactant mixture to a reactor, wherein the reactant mixture comprises methane ($CH_4$), wherein the reactor comprises a preheat zone, a catalyzed reaction zone (e.g., a primary reaction zone comprising a catalyst), an uncatalyzed reaction zone (e.g., a secondary reaction zone), and a quench zone; (b) heating the reactant mixture ($Q1_{in}$) to a preheating temperature in the preheat zone to yield a heated reactant mixture; wherein the preheat zone comprises a CSTR; wherein the preheat zone is designed to minimize a radial temperature gradient, to minimize compositional and/or flow gradients of the heated reactant mixture reaching the catalyzed reactor zone in the reactor, to minimize energy input, and the like, or combinations thereof; wherein the preheat zone comprises a preheater, wherein the preheater is designed to minimize a pressure drop across the preheat zone, to maximize heat transfer to the reactant mixture, to minimize energy input, to optimize flow of the heated reactant mixture into the catalyzed reaction zone, and the like, or combinations thereof; and wherein a design of the preheat zone and/or a design of the preheater can depend on a design of the catalyzed reaction zone for required heat, mass transfer, fluid dynamics, and the like, or combinations thereof; (c) contacting at least a portion of the heated reactant mixture with the catalyst in the catalyzed reaction zone to form a catalyst effluent mixture comprising free radicals, hydrocarbons, hydrogen and unreacted methane; wherein the catalyzed reaction zone is characterized by a catalyzed reaction zone temperature; wherein the catalyzed reaction zone is heated to the catalyzed reaction zone temperature ($Q2_{in}$); wherein the catalyzed reaction zone temperature is greater than the preheating temperature; wherein the catalyzed reaction zone comprises a CSTR; wherein the catalyzed reaction zone is designed to optimize heat transfer to the catalyst, to minimize energy costs, to maximize mass transfer of reactants to catalytic sites, to maximize mass transfer of products away from the catalytic sites, and the like, or combinations thereof; wherein the catalyst comprises particles, and wherein flow rates are optimized to maximize intra-particle and/or inter-particle mass transfer based on a stream composition; wherein heat transfer is optimized to maintain a desired temperature at a catalyst surface and/or in a gas phase within the catalyzed reaction zone, while minimizing energy input; and wherein the catalyzed reaction zone can be optionally designed to optimize catalyzed reaction zone conditions along a length of the catalyzed reaction zone as a composition of the gas phase changes due to conversion of reactants, wherein the catalyzed reaction zone conditions comprise variable catalyst formulation (e.g., catalyst composition, catalyst particle size, catalyst particle form, etc.), temperature, flow rate, mixing, fluid dynamics, staged addition of desired feeds and/or additives, and the like, or combinations thereof; (d) reacting at least a portion of the catalyst effluent mixture in the uncatalyzed reaction zone to form a reaction zone effluent mixture comprising $C_{2+}$ hydrocarbons, hydrogen, free radicals, and unreacted methane; wherein the uncatalyzed reaction zone is characterized by an uncatalyzed reaction zone temperature; wherein the uncatalyzed reaction zone is heated to the uncatalyzed reaction zone temperature ($Q3_{in}$); wherein the uncatalyzed reaction zone comprises a CSTR; wherein the uncatalyzed reaction zone is designed to optimize process conditions in the uncatalyzed reaction zone to obtain desired product yields while minimizing energy input, wherein the process conditions comprise temperature, temperature gradients, residence time, pressure, mixing and/or fluid dynamics, and the like, or combinations thereof; wherein gas phase reactions and/or reactions with reactor walls are optimized to obtain desired product yields; and wherein the uncatalyzed reaction zone is designed to optimize mixing in any staged addition of additives and/or agents that promote a desired production of $C_{2+}$ hydrocarbons and/or aromatic hydrocarbons, and/or limited formation of polycyclic aromatics and coke; (e) cooling at least a portion of the reaction zone effluent mixture ($-Q4_{in}$) in the quench zone to a quench temperature to yield a product mixture comprising $C_{2+}$ hydrocarbons, hydrogen, and unreacted methane, wherein the quench temperature is lower than the uncatalyzed reaction zone temperature, and wherein the quench zone comprises a CSTR; and wherein the quench zone is designed to optimize heat transfer to the reaction zone effluent mixture, to optimize quenching quickly and uniformly, while recovering high quality energy from the quench zone, and the like, or combinations thereof; and (f) recovering at least a portion of the product mixture from the reactor. In some embodiments of FIG. 4H, the quench zone can comprise an inner reactor wall comprising quench zone structures (e.g., fins) to increase heat removal. In other embodiments of FIG. 4H, the quench zone can comprise stacks and/or strings of particulates (e.g., spheres, ovals, etc.) to increase turbulence, thereby increasing heat transfer within the quench zone. In yet other embodiments of FIG. 4H, a quenching fluid (e.g., quenching agent, water, steam, etc.) can be introduced into the quench zone by using any suitable methodology, such as for example by using spray bars.

Referring to the embodiments of FIGS. 5A-5F, schematics of reactor designs are displayed, wherein the reactor comprises a preheat zone, a primary reaction zone comprising a catalyst (e.g., catalytic reaction zone), a secondary reaction zone, and a quench zone, indicating heat input (Qi). In such embodiments, temperatures, residence times, pressures, flow dynamics and mixing characteristics, reactor diameter and lengths of each of the four zones could have different values to optimize each zone and the reactor could be of singular construction (same reactor could comprise all four zones) or could comprise different types of reactors for at least two of the zones.

Figure 5A:
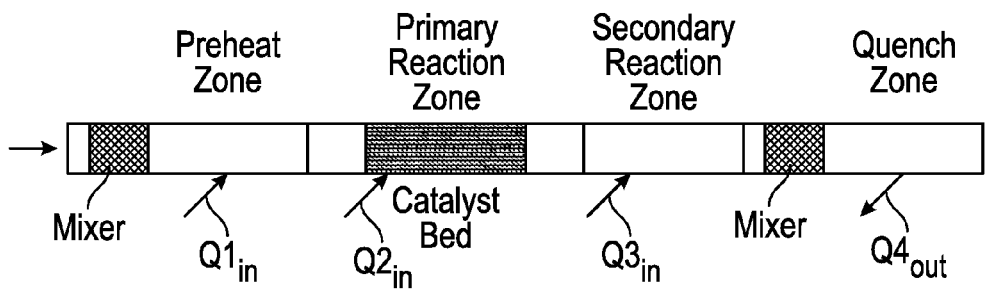
FIGS. 5A-5F display schematics of reactor designs comprising a preheat zone, a primary reaction zone comprising a catalyst, a secondary reaction zone, and a quench zone, indicating heat input (Qi)

Referring to the embodiment of FIG. 5A, a method for producing $C_{2+}$ hydrocarbons and hydrogen can comprise (a) introducing a reactant mixture to a reactor, wherein the reactant mixture comprises methane ($CH_4$), wherein the reactor comprises a preheat zone, a catalyzed reaction zone (e.g., a primary reaction zone comprising a catalyst bed), an uncatalyzed reaction zone (e.g., a secondary reaction zone), and a quench zone; (b) heating the reactant mixture ($Q1_{in}$) to a preheating temperature in the preheat zone to yield a heated reactant mixture; wherein the preheat zone comprises a mixer; wherein the reactant mixture and/or the heated reactant mixture is mixed in the preheat zone; wherein the mixer is designed to minimize a radial temperature gradient, to minimize compositional and/or flow gradients of the heated reactant mixture reaching the catalyzed reactor zone in the reactor, to minimize energy input, to minimize a pressure drop across the preheat zone, to maximize heat transfer to the reactant mixture, to optimize flow of the heated reactant mixture into the catalyzed reaction zone, and the like, or combinations thereof; and wherein a design of the preheat zone and/or a design of the mixer can depend on a design of the catalyzed reaction zone for required heat, mass transfer, fluid dynamics, and the like, or combinations thereof; (c) contacting at least a portion of the heated reactant mixture with the catalyst bed in the catalyzed reaction zone to form a catalyst effluent mixture comprising free radicals, hydrocarbons, hydrogen and unreacted methane; wherein the catalyzed reaction zone is characterized by a catalyzed reaction zone temperature; wherein the catalyzed reaction zone is heated to the catalyzed reaction zone temperature ($Q2_{in}$); wherein the catalyzed reaction zone temperature is greater than the preheating temperature; wherein the catalyzed reaction zone is designed to optimize heat transfer to the catalyst, to minimize energy costs, to maximize mass transfer of reactants to catalytic sites, to maximize mass transfer of products away from the catalytic sites, and the like, or combinations thereof; wherein the catalyst comprises particles, and wherein flow rates are optimized to maximize intra-particle and/or inter-particle mass transfer based on a stream composition; wherein heat transfer is optimized to maintain a desired temperature at a catalyst surface and/or in a gas phase within the catalyzed reaction zone, while minimizing energy input; and wherein the catalyzed reaction zone can be optionally designed to optimize catalyzed reaction zone conditions along a length of the catalyzed reaction zone as a composition of the gas phase changes due to conversion of reactants, wherein the catalyzed reaction zone conditions comprise variable catalyst formulation (e.g., catalyst composition, catalyst particle size, catalyst particle form, etc.), temperature, flow rate, mixing, fluid dynamics, staged addition of desired feeds and/or additives, and the like, or combinations thereof; (d) reacting at least a portion of the catalyst effluent mixture in the uncatalyzed reaction zone to form a reaction zone effluent mixture comprising $C_{2+}$ hydrocarbons, hydrogen, free radicals, and unreacted methane; wherein the uncatalyzed reaction zone is characterized by an uncatalyzed reaction zone temperature; wherein the uncatalyzed reaction zone is heated to the uncatalyzed reaction zone temperature ($Q3_{in}$); wherein the uncatalyzed reaction zone is designed to optimize process conditions in the uncatalyzed reaction zone to obtain desired product yields while minimizing energy input, wherein the process conditions comprise temperature, temperature gradients, residence time, pressure, mixing and/or fluid dynamics, and the like, or combinations thereof; wherein gas phase reactions and/or reactions with reactor walls are optimized to obtain desired product yields; and wherein the uncatalyzed reaction zone is designed to optimize mixing in any staged addition of additives and/or agents that promote a desired production of $C_{2+}$ hydrocarbons and/or aromatic hydrocarbons, and/or limited formation of polycyclic aromatics and coke; (e) cooling at least a portion of the reaction zone effluent mixture ($Q4_{out}$) in the quench zone to a quench temperature to yield a product mixture comprising $C_{2+}$ hydrocarbons, hydrogen, and unreacted methane; wherein the quench temperature is lower than the uncatalyzed reaction zone temperature; wherein the quench zone comprises a mixer; and wherein the reaction zone effluent mixture and/or the product mixture is mixed in the quench zone to optimize heat transfer to the reaction zone effluent mixture, to optimize quenching quickly and uniformly, while recovering high quality energy from the quench zone, and the like, or combinations thereof; and (f) recovering at least a portion of the product mixture from the reactor. In some embodiments of FIG. 5A, the quench zone can comprise an inner reactor wall comprising quench zone structures (e.g., fins) to increase heat removal. In other embodiments of FIG. 5A, the quench zone can comprise stacks and/or strings of particulates (e.g., spheres, ovals, etc.) to increase turbulence, thereby increasing heat transfer within the quench zone. In yet other embodiments of FIG. 5A, a quenching fluid (e.g., quenching agent, water, steam, etc.) can be introduced into the quench zone by using any suitable methodology, such as for example by using spray bars.

Figure 5B:
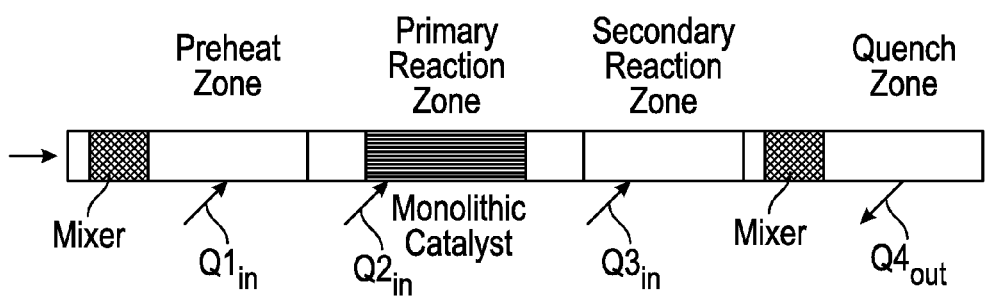

Referring to the embodiment of FIG. 5B, a method for producing $C_{2+}$ hydrocarbons and hydrogen can comprise (a) introducing a reactant mixture to a reactor, wherein the reactant mixture comprises methane ($CH_4$), wherein the reactor comprises a preheat zone, a catalyzed reaction zone (e.g., a primary reaction zone comprising a catalyst bed), an uncatalyzed reaction zone (e.g., a secondary reaction zone), and a quench zone; (b) heating the reactant mixture ($Q1_{in}$) to a preheating temperature in the preheat zone to yield a heated reactant mixture; wherein the preheat zone comprises a mixer; wherein the reactant mixture and/or the heated reactant mixture is mixed in the preheat zone; wherein the mixer is designed to minimize a radial temperature gradient, to minimize compositional and/or flow gradients of the heated reactant mixture reaching the catalyzed reactor zone in the reactor, to minimize energy input, to minimize a pressure drop across the preheat zone, to maximize heat transfer to the reactant mixture, to optimize flow of the heated reactant mixture into the catalyzed reaction zone, and the like, or combinations thereof; and wherein a design of the preheat zone and/or a design of the mixer can depend on a design of the catalyzed reaction zone for required heat, mass transfer, fluid dynamics, and the like, or combinations thereof; (c) contacting at least a portion of the heated reactant mixture with the catalyst bed in the catalyzed reaction zone to form a catalyst effluent mixture comprising free radicals, hydrocarbons, hydrogen and unreacted methane; wherein the catalyzed reaction zone is characterized by a catalyzed reaction zone temperature; wherein the catalyzed reaction zone is heated to the catalyzed reaction zone temperature ($Q2_{in}$); wherein the catalyzed reaction zone temperature is greater than the preheating temperature; wherein the catalyst bed comprises a monolithic catalyst, alternatively a honeycomb catalyst, alternatively a honeycombed wall filter design catalyst, alternatively a monolithic foam of ceramic construction, alternatively a monolithic foam of metal construction, and the like, or combinations thereof, wherein the monolithic foam of ceramic and/or metal construction can comprise an active catalyst in a washcoat form; wherein the monolithic catalyst is designed to minimize pressure drops, to optimize mass transfer of reactants to catalytic sites, to optimize mass transfer of products away from the catalytic sites, to optimize contact time (e.g., residence time), to optimize heat flow through the monolithic catalyst, to optimize gas mixture flow through the monolith, and the like, or combinations thereof; (d) reacting at least a portion of the catalyst effluent mixture in the uncatalyzed reaction zone to form a reaction zone effluent mixture comprising $C_{2+}$ hydrocarbons, hydrogen, free radicals, and unreacted methane; wherein the uncatalyzed reaction zone is characterized by an uncatalyzed reaction zone temperature; wherein the uncatalyzed reaction zone is heated to the uncatalyzed reaction zone temperature ($Q3_{in}$); wherein the uncatalyzed reaction zone is designed to optimize process conditions in the uncatalyzed reaction zone to obtain desired product yields while minimizing energy input, wherein the process conditions comprise temperature, temperature gradients, residence time, pressure, mixing and/or fluid dynamics, and the like, or combinations thereof; wherein gas phase reactions and/or reactions with reactor walls are optimized to obtain desired product yields; and wherein the uncatalyzed reaction zone is designed to optimize mixing in any staged addition of additives and/or agents that promote a desired production of $C_{2+}$ hydrocarbons and/or aromatic hydrocarbons, and/or limited formation of polycyclic aromatics and coke; (e) cooling at least a portion of the reaction zone effluent mixture ($Q4_{out}$) in the quench zone to a quench temperature to yield a product mixture comprising $C_{2+}$ hydrocarbons, hydrogen, and unreacted methane; wherein the quench temperature is lower than the uncatalyzed reaction zone temperature; wherein the quench zone comprises a mixer; and wherein the reaction zone effluent mixture and/or the product mixture is mixed in the quench zone to optimize heat transfer to the reaction zone effluent mixture, to optimize quenching quickly and uniformly, while recovering high quality energy from the quench zone, and the like, or combinations thereof; and (f) recovering at least a portion of the product mixture from the reactor. In some embodiments of FIG. 5B, the quench zone can comprise an inner reactor wall comprising quench zone structures (e.g., fins) to increase heat removal. In other embodiments of FIG. 5B, the quench zone can comprise stacks and/or strings of particulates (e.g., spheres, ovals, etc.) to increase turbulence, thereby increasing heat transfer within the quench zone. In yet other embodiments of FIG. 5B, a quenching fluid (e.g., quenching agent, water, steam, etc.) can be introduced into the quench zone by using any suitable methodology, such as for example by using spray bars.

Figure 5C:
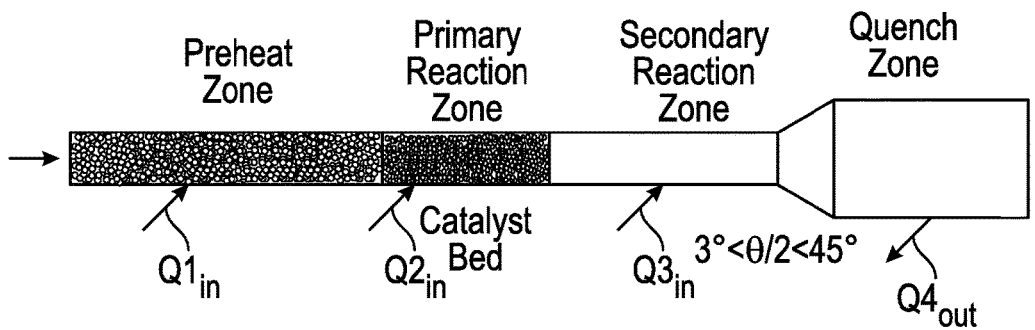

Referring to the embodiment of FIG. 5C, a method for producing $C_{2+}$ hydrocarbons and hydrogen can comprise (a) introducing a reactant mixture to a reactor, wherein the reactant mixture comprises methane ($CH_4$), wherein the reactor comprises a preheat zone, a catalyzed reaction zone (e.g., a primary reaction zone comprising a catalyst bed), an uncatalyzed reaction zone (e.g., a secondary reaction zone), and a quench zone; (b) heating the reactant mixture ($Q1_{in}$) to a preheating temperature in the preheat zone to yield a heated reactant mixture; wherein the preheat zone comprises a shaped support (e.g., quartz pieces, SiC beads, saddle-shaped support, wagon wheel-shaped support, etc.) that causes mixing and heat transfer to the reactant mixture; and wherein the shaped support is characterized by a size effective to (e.g., large enough to) to prevent significant pressure drop across the zone; (c) contacting at least a portion of the heated reactant mixture with the catalyst bed (e.g., catalyst beads or particles) in the catalyzed reaction zone to form a catalyst effluent mixture comprising free radicals, hydrocarbons, hydrogen and unreacted methane; wherein the catalyzed reaction zone is characterized by a catalyzed reaction zone temperature; wherein the catalyzed reaction zone is heated to the catalyzed reaction zone temperature ($Q2_{in}$); wherein the catalyzed reaction zone temperature is greater than the preheating temperature; wherein the catalyzed reaction zone is designed to optimize heat transfer to the catalyst, to minimize energy costs, to maximize mass transfer of reactants to catalytic sites, to maximize mass transfer of products away from the catalytic sites, and the like, or combinations thereof; wherein the catalyst comprises particles, and wherein flow rates are optimized to maximize intra-particle and/or inter-particle mass transfer based on a stream composition; wherein heat transfer is optimized to maintain a desired temperature at a catalyst surface and/or in a gas phase within the catalyzed reaction zone, while minimizing energy input; and wherein the catalyzed reaction zone can be optionally designed to optimize catalyzed reaction zone conditions along a length of the catalyzed reaction zone as a composition of the gas phase changes due to conversion of reactants, wherein the catalyzed reaction zone conditions comprise variable catalyst formulation (e.g., catalyst composition, catalyst particle size, catalyst particle form, etc.), temperature, flow rate, mixing, fluid dynamics, staged addition of desired feeds and/or additives, and the like, or combinations thereof; (d) reacting at least a portion of the catalyst effluent mixture in the uncatalyzed reaction zone to form a reaction zone effluent mixture comprising $C_{2+}$ hydrocarbons, hydrogen, free radicals, and unreacted methane; wherein the uncatalyzed reaction zone is characterized by an uncatalyzed reaction zone temperature; wherein the uncatalyzed reaction zone is heated to the uncatalyzed reaction zone temperature ($Q3_{in}$); wherein the uncatalyzed reaction zone is designed to optimize process conditions in the uncatalyzed reaction zone to obtain desired product yields while minimizing energy input, wherein the process conditions comprise temperature, temperature gradients, residence time, pressure, mixing and/or fluid dynamics, and the like, or combinations thereof; wherein gas phase reactions and/or reactions with reactor walls are optimized to obtain desired product yields; and wherein the uncatalyzed reaction zone is designed to optimize mixing in any staged addition of additives and/or agents that promote a desired production of $C_{2+}$ hydrocarbons and/or aromatic hydrocarbons, and/or limited formation of polycyclic aromatics and coke; (e) cooling at least a portion of the reaction zone effluent mixture ($Q4_{out}$) in the quench zone to a quench temperature to yield a product mixture comprising $C_{2+}$ hydrocarbons, hydrogen, and unreacted methane; wherein the quench temperature is lower than the uncatalyzed reaction zone temperature; wherein cooling is accomplished by kinetic energy quench (e.g., Joule Thompson expander, choke nozzle, turbo expander, etc.); wherein an inner diameter of the quench zone is greater than an inner diameter of the uncatalyzed reaction zone; and wherein a transition from the inner diameter of the uncatalyzed reaction to the zone inner diameter of the quench zone comprises an angle of from about 6° to about 90°, eliminating a need for introducing quench liquids, thereby increasing an overall energy and economic efficiency of the method; and (f) recovering at least a portion of the product mixture from the reactor. In some embodiments of FIG. 5C, a quenching fluid (e.g., quenching agent, water, steam, etc.) can be introduced into the quench zone by using any suitable methodology, such as for example by using spray bars, in addition to cooling by kinetic energy quench.

Figure 5D:
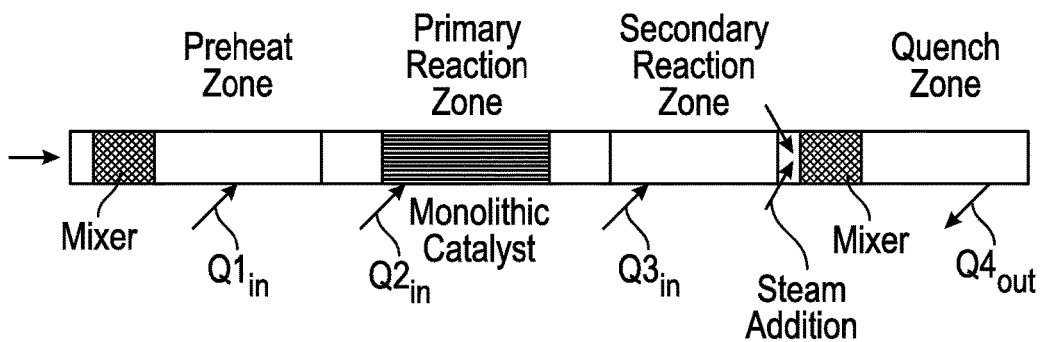

Referring to the embodiment of FIG. 5D, a method for producing $C_{2+}$ hydrocarbons and hydrogen can comprise (a) introducing a reactant mixture to a reactor, wherein the reactant mixture comprises methane ($CH_4$), wherein the reactor comprises a preheat zone, a catalyzed reaction zone (e.g., a primary reaction zone comprising a catalyst bed), an uncatalyzed reaction zone (e.g., a secondary reaction zone), and a quench zone; (b) heating the reactant mixture ($Q1_{in}$) to a preheating temperature in the preheat zone to yield a heated reactant mixture; wherein the preheat zone comprises a mixer; wherein the reactant mixture and/or the heated reactant mixture is mixed in the preheat zone; wherein the mixer is designed to minimize a radial temperature gradient, to minimize compositional and/or flow gradients of the heated reactant mixture reaching the catalyzed reactor zone in the reactor, to minimize energy input, to minimize a pressure drop across the preheat zone, to maximize heat transfer to the reactant mixture, to optimize flow of the heated reactant mixture into the catalyzed reaction zone, and the like, or combinations thereof; and wherein a design of the preheat zone and/or a design of the mixer can depend on a design of the catalyzed reaction zone for required heat, mass transfer, fluid dynamics, and the like, or combinations thereof; (c) contacting at least a portion of the heated reactant mixture with the catalyst bed in the catalyzed reaction zone to form a catalyst effluent mixture comprising free radicals, hydrocarbons, hydrogen and unreacted methane; wherein the catalyzed reaction zone is characterized by a catalyzed reaction zone temperature; wherein the catalyzed reaction zone is heated to the catalyzed reaction zone temperature ($Q2_{in}$); wherein the catalyzed reaction zone temperature is greater than the preheating temperature; wherein the catalyst bed comprises a monolithic catalyst, alternatively a honeycomb catalyst, alternatively a honeycombed wall filter design catalyst, alternatively a monolithic foam of ceramic construction, alternatively a monolithic foam of metal construction, and the like, or combinations thereof, wherein the monolithic foam of ceramic and/or metal construction can comprise an active catalyst in a washcoat form; wherein the monolithic catalyst is designed to minimize pressure drops, to optimize mass transfer of reactants to catalytic sites, to optimize mass transfer of products away from the catalytic sites, to optimize contact time (e.g., residence time), to optimize heat flow through the monolithic catalyst, to optimize gas mixture flow through the monolith, and the like, or combinations thereof; (d) reacting at least a portion of the catalyst effluent mixture in the uncatalyzed reaction zone to form a reaction zone effluent mixture comprising $C_{2+}$ hydrocarbons, hydrogen, free radicals, and unreacted methane; wherein the uncatalyzed reaction zone is characterized by an uncatalyzed reaction zone temperature; wherein the uncatalyzed reaction zone is heated to the uncatalyzed reaction zone temperature ($Q3_{in}$); wherein the uncatalyzed reaction zone is designed to optimize process conditions in the uncatalyzed reaction zone to obtain desired product yields while minimizing energy input, wherein the process conditions comprise temperature, temperature gradients, residence time, pressure, mixing and/or fluid dynamics, and the like, or combinations thereof; wherein gas phase reactions and/or reactions with reactor walls are optimized to obtain desired product yields; and wherein the uncatalyzed reaction zone is designed to optimize mixing in any staged addition of additives and/or agents that promote a desired production of $C_{2+}$ hydrocarbons and/or aromatic hydrocarbons, and/or limited formation of polycyclic aromatics and coke; (e) cooling at least a portion of the reaction zone effluent mixture ($Q4_{out}$) in the quench zone to a quench temperature to yield a product mixture comprising $C_{2+}$ hydrocarbons, hydrogen, and unreacted methane; wherein the quench temperature is lower than the uncatalyzed reaction zone temperature; wherein the quench zone comprises a mixer; wherein the reaction zone effluent mixture and/or the product mixture is mixed in the quench zone to optimize heat transfer to the reaction zone effluent mixture, to optimize quenching quickly and uniformly, while recovering high quality energy from the quench zone, and the like, or combinations thereof; and wherein a quenching fluid (e.g., quenching agent, water, steam, etc.) can be introduced into the quench zone by using any suitable methodology, such as for example by using spray bars; and (f) recovering at least a portion of the product mixture from the reactor. In some embodiments of FIG. 5D, the quench zone can comprise an inner reactor wall comprising quench zone structures (e.g., fins) to increase heat removal. In other embodiments of FIG. 5D, the quench zone can comprise stacks and/or strings of particulates (e.g., spheres, ovals, etc.) to increase turbulence, thereby increasing heat transfer within the quench zone.

Figure 5E:
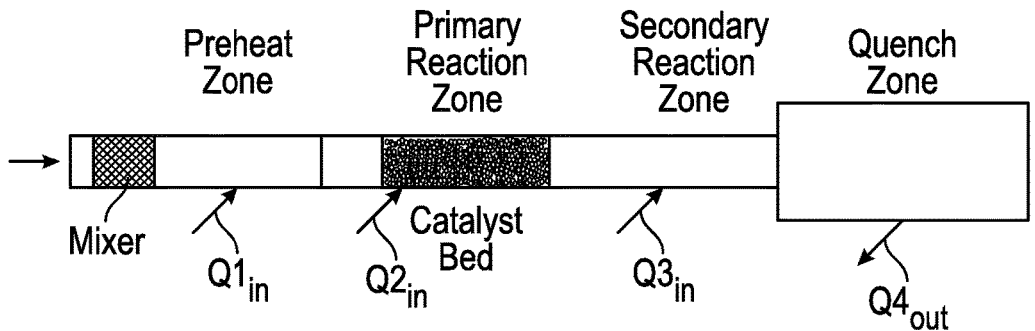

Referring to the embodiment of FIG. 5E, a method for producing $C_{2+}$ hydrocarbons and hydrogen can comprise (a) introducing a reactant mixture to a reactor, wherein the reactant mixture comprises methane ($CH_4$), wherein the reactor comprises a preheat zone, a catalyzed reaction zone (e.g., a primary reaction zone comprising a catalyst bed), an uncatalyzed reaction zone (e.g., a secondary reaction zone), and a quench zone; (b) heating the reactant mixture ($Q1_{in}$) to a preheating temperature in the preheat zone to yield a heated reactant mixture; wherein the preheat zone comprises a mixer; wherein the reactant mixture and/or the heated reactant mixture is mixed in the preheat zone; wherein the mixer is designed to minimize a radial temperature gradient, to minimize compositional and/or flow gradients of the heated reactant mixture reaching the catalyzed reactor zone in the reactor, to minimize energy input, to minimize a pressure drop across the preheat zone, to maximize heat transfer to the reactant mixture, to optimize flow of the heated reactant mixture into the catalyzed reaction zone, and the like, or combinations thereof; and wherein a design of the preheat zone and/or a design of the mixer can depend on a design of the catalyzed reaction zone for required heat, mass transfer, fluid dynamics, and the like, or combinations thereof; (c) contacting at least a portion of the heated reactant mixture with the catalyst bed (e.g., catalyst beads or particles) in the catalyzed reaction zone to form a catalyst effluent mixture comprising free radicals, hydrocarbons, hydrogen and unreacted methane; wherein the catalyzed reaction zone is characterized by a catalyzed reaction zone temperature; wherein the catalyzed reaction zone is heated to the catalyzed reaction zone temperature ($Q2_{in}$); wherein the catalyzed reaction zone temperature is greater than the preheating temperature; wherein the catalyzed reaction zone is designed to optimize heat transfer to the catalyst, to minimize energy costs, to maximize mass transfer of reactants to catalytic sites, to maximize mass transfer of products away from the catalytic sites, and the like, or combinations thereof; wherein the catalyst comprises particles, and wherein flow rates are optimized to maximize intra-particle and/or inter-particle mass transfer based on a stream composition; wherein heat transfer is optimized to maintain a desired temperature at a catalyst surface and/or in a gas phase within the catalyzed reaction zone, while minimizing energy input; and wherein the catalyzed reaction zone can be optionally designed to optimize catalyzed reaction zone conditions along a length of the catalyzed reaction zone as a composition of the gas phase changes due to conversion of reactants, wherein the catalyzed reaction zone conditions comprise variable catalyst formulation (e.g., catalyst composition, catalyst particle size, catalyst particle form, etc.), temperature, flow rate, mixing, fluid dynamics, staged addition of desired feeds and/or additives, and the like, or combinations thereof; (d) reacting at least a portion of the catalyst effluent mixture in the uncatalyzed reaction zone to form a reaction zone effluent mixture comprising $C_{2+}$ hydrocarbons, hydrogen, free radicals, and unreacted methane; wherein the uncatalyzed reaction zone is characterized by an uncatalyzed reaction zone temperature; wherein the uncatalyzed reaction zone is heated to the uncatalyzed reaction zone temperature ($Q3_{in}$); wherein the uncatalyzed reaction zone is designed to optimize process conditions in the uncatalyzed reaction zone to obtain desired product yields while minimizing energy input, wherein the process conditions comprise temperature, temperature gradients, residence time, pressure, mixing and/or fluid dynamics, and the like, or combinations thereof; wherein gas phase reactions and/or reactions with reactor walls are optimized to obtain desired product yields; and wherein the uncatalyzed reaction zone is designed to optimize mixing in any staged addition of additives and/or agents that promote a desired production of $C_{2+}$ hydrocarbons and/or aromatic hydrocarbons, and/or limited formation of polycyclic aromatics and coke; (e) cooling at least a portion of the reaction zone effluent mixture ($Q4_{out}$) in the quench zone to a quench temperature to yield a product mixture comprising $C_{2+}$ hydrocarbons, hydrogen, and unreacted methane; wherein the quench temperature is lower than the uncatalyzed reaction zone temperature; wherein cooling is accomplished by kinetic energy quench (e.g., Joule Thompson expander, choke nozzle, turbo expander, etc.); wherein an inner diameter of the quench zone is greater than an inner diameter of the uncatalyzed reaction zone; and wherein a transition from the inner diameter of the uncatalyzed reaction to the zone inner diameter of the quench zone comprises an angle of about 90°, eliminating a need for introducing quench liquids, thereby increasing an overall energy and economic efficiency of the method; and (f) recovering at least a portion of the product mixture from the reactor. In some embodiments of FIG. 5E, a quenching fluid (e.g., quenching agent, water, steam, etc.) can be introduced into the quench zone by using any suitable methodology, such as for example by using spray bars, in addition to cooling by kinetic energy quench.

Figure 5F:
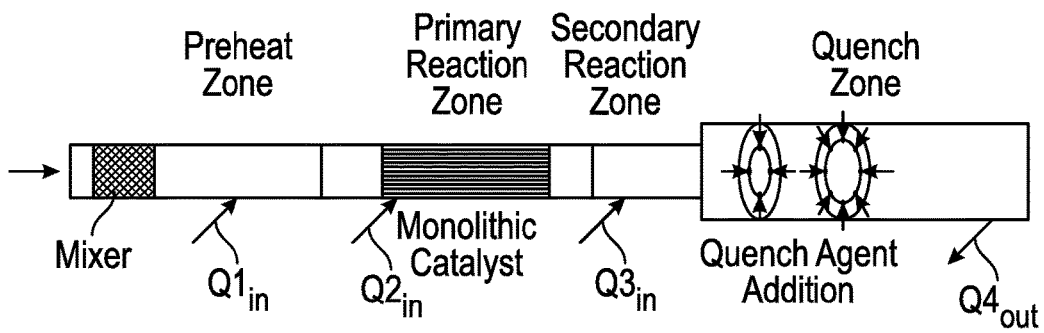

Referring to the embodiment of FIG. 5F, a method for producing $C_{2+}$ hydrocarbons and hydrogen can comprise (a) introducing a reactant mixture to a reactor, wherein the reactant mixture comprises methane ($CH_4$), wherein the reactor comprises a preheat zone, a catalyzed reaction zone (e.g., a primary reaction zone comprising a catalyst bed), an uncatalyzed reaction zone (e.g., a secondary reaction zone), and a quench zone; (b) heating the reactant mixture ($Q1_{in}$) to a preheating temperature in the preheat zone to yield a heated reactant mixture; wherein the preheat zone comprises a mixer; wherein the reactant mixture and/or the heated reactant mixture is mixed in the preheat zone; wherein the mixer is designed to minimize a radial temperature gradient, to minimize compositional and/or flow gradients of the heated reactant mixture reaching the catalyzed reactor zone in the reactor, to minimize energy input, to minimize a pressure drop across the preheat zone, to maximize heat transfer to the reactant mixture, to optimize flow of the heated reactant mixture into the catalyzed reaction zone, and the like, or combinations thereof; and wherein a design of the preheat zone and/or a design of the mixer can depend on a design of the catalyzed reaction zone for required heat, mass transfer, fluid dynamics, and the like, or combinations thereof; (c) contacting at least a portion of the heated reactant mixture with the catalyst bed in the catalyzed reaction zone to form a catalyst effluent mixture comprising free radicals, hydrocarbons, hydrogen and unreacted methane; wherein the catalyzed reaction zone is characterized by a catalyzed reaction zone temperature; wherein the catalyzed reaction zone is heated to the catalyzed reaction zone temperature ($Q2_{in}$); wherein the catalyzed reaction zone temperature is greater than the preheating temperature; wherein the catalyst bed comprises a monolithic catalyst, alternatively a honeycomb catalyst, alternatively a honeycombed wall filter design catalyst, alternatively a monolithic foam of ceramic construction, alternatively a monolithic foam of metal construction, and the like, or combinations thereof, wherein the monolithic foam of ceramic and/or metal construction can comprise an active catalyst in a washcoat form; wherein the monolithic catalyst is designed to minimize pressure drops, to optimize mass transfer of reactants to catalytic sites, to optimize mass transfer of products away from the catalytic sites, to optimize contact time (e.g., residence time), to optimize heat flow through the monolithic catalyst, to optimize gas mixture flow through the monolith, and the like, or combinations thereof; (d) reacting at least a portion of the catalyst effluent mixture in the uncatalyzed reaction zone to form a reaction zone effluent mixture comprising $C_{2+}$ hydrocarbons, hydrogen, free radicals, and unreacted methane; wherein the uncatalyzed reaction zone is characterized by an uncatalyzed reaction zone temperature; wherein the uncatalyzed reaction zone is heated to the uncatalyzed reaction zone temperature ($Q3_{in}$); wherein the uncatalyzed reaction zone is designed to optimize process conditions in the uncatalyzed reaction zone to obtain desired product yields while minimizing energy input, wherein the process conditions comprise temperature, temperature gradients, residence time, pressure, mixing and/or fluid dynamics, and the like, or combinations thereof; wherein gas phase reactions and/or reactions with reactor walls are optimized to obtain desired product yields; and wherein the uncatalyzed reaction zone is designed to optimize mixing in any staged addition of additives and/or agents that promote a desired production of $C_{2+}$ hydrocarbons and/or aromatic hydrocarbons, and/or limited formation of polycyclic aromatics and coke; (e) cooling at least a portion of the reaction zone effluent mixture ($Q4_{out}$) in the quench zone to a quench temperature to yield a product mixture comprising $C_{2+}$ hydrocarbons, hydrogen, and unreacted methane; wherein the quench temperature is lower than the uncatalyzed reaction zone temperature; wherein cooling is accomplished by kinetic energy quench (e.g., Joule Thompson expander, choke nozzle, turbo expander, etc.); wherein an inner diameter of the quench zone is greater than an inner diameter of the uncatalyzed reaction zone; wherein a transition from the inner diameter of the uncatalyzed reaction to the zone inner diameter of the quench zone comprises an angle of about 90°; and wherein a quenching fluid (e.g., quenching agent, water, steam, etc.) can be introduced into the quench zone by using any suitable methodology, such as for example by using an assembly of a plurality of injection nozzles (as depicted in FIG. 2) that can be radially distributed within the reactor (e.g., reactor tube); and (f) recovering at least a portion of the product mixture from the reactor.

Figure 6:
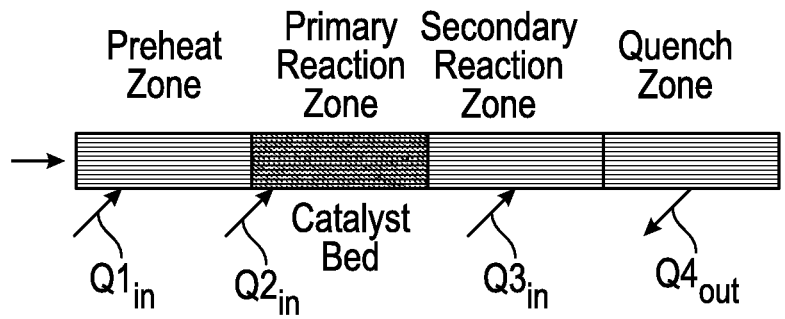
FIG. 6 displays a schematic of a reactor design with microchannel technology wherein the reactor comprises a preheat zone, a primary reaction zone comprising a catalyst bed, a secondary reaction zone, and a quench zone, indicating heat input (Qi)

Referring to the embodiment of FIG. 6, a reactor design schematic is displayed, wherein the reactor is a modular reactor with microchannel technology (e.g., a modular microchannel reactor) comprising a preheat zone, a primary reaction zone comprising a catalyst bed (e.g., catalytic reaction zone), a secondary reaction zone, and a quench zone, indicating heat input (Qi). In such embodiment, temperatures, residence times, pressures, flow dynamics and mixing characteristics, reactor diameter and lengths of the four zones could have different values to optimize each zone and the reactor could be of singular construction (same reactor could comprise all four zones) or could comprise different types of reactors for at least two of the zones. The reactors could be of modular design or of non-modular design. Modular reactors generally refer to reactors that can be assembled from multiple parts (e.g., modules). Reactors with microchannels (e.g., microchannel reactors) can generally comprise a particulate catalyst in small (micro) channels, which can be referred to as "catalytic bed channels." Microchannel reactors are compact reactors that can have channels with diameters in the mm range. Microchannel heat exchangers (e.g., a heat exchanger module) can be installed in modular reactors between catalytic bed channels. In a microchannel reactor, a single reactor module can comprise hundreds of rows of microchannels, wherein each row can contain large numbers of parallel microchannels. Microchannel orientation and size within each row can be determined by the application, as adjacent rows of channels could potentially have different duties; for example, a row could perform a chemical reaction, while an adjacent row could perform heat exchange.

Referring to the embodiment of FIG. 6, a method for producing $C_{2+}$ hydrocarbons and hydrogen can comprise (a) introducing a reactant mixture to a modular microchannel reactor, wherein the reactant mixture comprises methane ($CH_4$), wherein the modular microchannel reactor comprises a preheat zone, a catalyzed reaction zone (e.g., a primary reaction zone comprising a catalyst bed), an uncatalyzed reaction zone (e.g., a secondary reaction zone), and a quench zone; (b) heating the reactant mixture ($Q1_{in}$) to a preheating temperature in the preheat zone to yield a heated reactant mixture, wherein the preheat zone comprises a microchannel heat exchanger for heating the reactant mixture, and wherein a preheat zone design maximizes heat transfer to the reactant mixture; (c) contacting at least a portion of the heated reactant mixture with the catalyst bed in the catalyzed reaction zone to form a catalyst effluent mixture comprising free radicals, hydrocarbons, hydrogen and unreacted methane, wherein the catalyzed reaction zone is characterized by a catalyzed reaction zone temperature, wherein the catalyzed reaction zone is heated to the catalyzed reaction zone temperature ($Q2_{in}$), wherein the catalyzed reaction zone temperature is greater than the preheating temperature, wherein the catalyzed reaction zone comprises a microchannel heat exchanger for heating the catalyzed reaction zone coated with or composed of catalytically active materials, and wherein the catalyst bed comprises catalytic bed channels that can lead to an increase in mass transfer of from about 10 fold to about 100 fold in the catalyzed reaction zone and to optimized control of heat transfer; (d) reacting at least a portion of the catalyst effluent mixture in the uncatalyzed reaction zone to form a reaction zone effluent mixture comprising $C_{2+}$ hydrocarbons, hydrogen, free radicals, and unreacted methane, wherein the uncatalyzed reaction zone is characterized by an uncatalyzed reaction zone temperature, wherein the uncatalyzed reaction zone is heated to the uncatalyzed reaction zone temperature ($Q3_{in}$), wherein the uncatalyzed reaction zone comprises a microchannel heat exchanger to heat the uncatalyzed reaction zone, wherein the uncatalyzed reaction zone comprises microchannels for reacting at least a portion of the catalyst effluent mixture to form a reaction zone effluent mixture, wherein an uncatalyzed reaction zone design provides for increased mass transfer, and wherein a contribution of gas phase-surface reactions is significantly higher than in conventional reactor designs; (e) cooling at least a portion of the reaction zone effluent mixture ($Q4_{out}$) in the quench zone to a quench temperature to yield a product mixture comprising $C_{2+}$ hydrocarbons, hydrogen, and unreacted methane, wherein the quench temperature is lower than the uncatalyzed reaction zone temperature, and wherein the quench zone comprises a microchannel heat exchanger to cool the quench zone, allowing for very fast heat removal and quenching; and (f) recovering at least a portion of the product mixture from the reactor. In such embodiment, design flexibility in microchannel reactor construction allows for s/v ratio control.

Figure 7A:
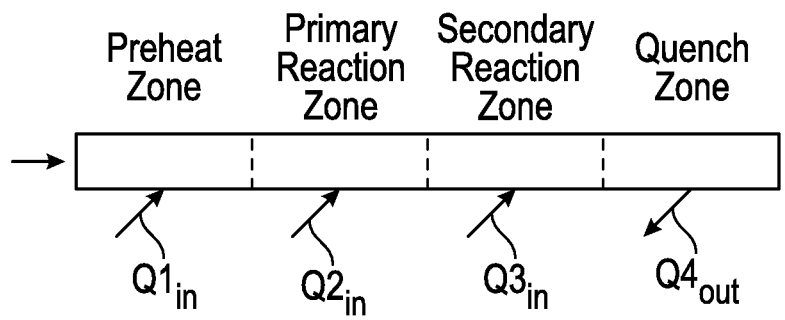
FIG. 7A displays a schematic of a reactor design of a tubular reactor comprising a preheat zone, a primary reaction zone comprising a catalyst, a secondary reaction zone, and a quench zone, indicating heat input (Qi), wherein the reactors are entirely or partially manufactured from and/or surface coated with catalyst materials.

Referring to the embodiment of FIG. 7A, a method for producing $C_{2+}$ hydrocarbons and hydrogen can comprise (a) introducing a reactant mixture to a reactor (e.g., a reactor tube), wherein the reactant mixture comprises methane ($CH_4$), wherein the reactor and/or an inner reactor surface is partially or entirely manufactured from and/or surface coated with a catalyst (e.g., catalyst material), and wherein the reactor comprises a preheat zone, a catalyzed reaction zone (e.g., a primary reaction zone comprising a catalytic tube), an uncatalyzed reaction zone (e.g., a secondary reaction zone), and a quench zone; (b) heating the reactant mixture ($Q1_{in}$) to a preheating temperature in the preheat zone to yield a heated reactant mixture, wherein the preheat zone comprises a heat exchanger for heating the reactant mixture; (c) contacting at least a portion of the heated reactant mixture with the catalytic tube in the catalyzed reaction zone to form a catalyst effluent mixture comprising free radicals, hydrocarbons, hydrogen and unreacted methane, wherein the catalyzed reaction zone is characterized by a catalyzed reaction zone temperature, wherein the catalyzed reaction zone is heated to the catalyzed reaction zone temperature ($Q2_{in}$), wherein the catalyzed reaction zone temperature is greater than the preheating temperature, wherein the catalyzed reaction zone comprises a heat exchanger for heating the catalyzed reaction zone, and wherein the catalytic tube and/or an inner catalytic tube surface in the catalyzed reaction zone is partially or entirely manufactured from and/or surface coated with a catalyst (e.g., catalyst material); (d) reacting at least a portion of the catalyst effluent mixture in the uncatalyzed reaction zone to form a reaction zone effluent mixture comprising $C_{2+}$ hydrocarbons, hydrogen, free radicals, and unreacted methane, wherein the uncatalyzed reaction zone is characterized by an uncatalyzed reaction zone temperature, wherein the uncatalyzed reaction zone is heated to the uncatalyzed reaction zone temperature ($Q3_{in}$), wherein the uncatalyzed reaction zone comprises a heat exchanger to heat the uncatalyzed reaction zone, and wherein at least a portion of an uncatalyzed reaction zone surface reacts with at least a portion of the catalyst effluent mixture to form a reaction zone effluent mixture; (e) cooling at least a portion of the reaction zone effluent mixture ($Q4_{out}$) in the quench zone to a quench temperature to yield a product mixture comprising $C_{2+}$ hydrocarbons, hydrogen, and unreacted methane, wherein the quench temperature is lower than the uncatalyzed reaction zone temperature, and wherein the quench zone comprises a heat exchanger to cool the quench zone; and (f) recovering at least a portion of the product mixture from the reactor.

Figure 7B:
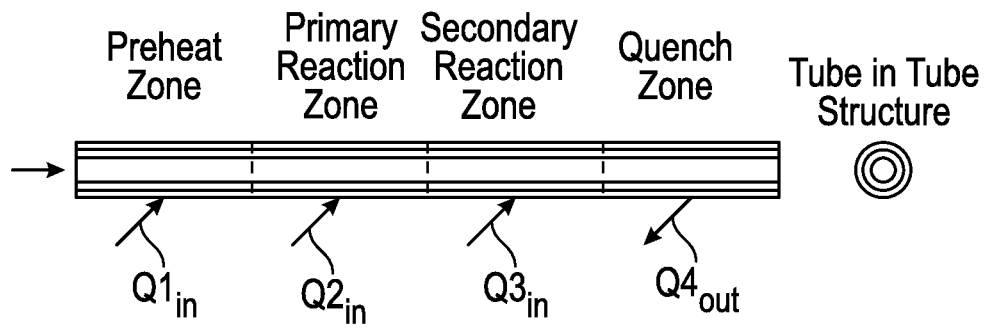
FIG. 7B displays a schematic of reactors of FIG. 7A in a concentric placement.

Referring to the embodiment of FIG. 7B, a method for producing $C_{2+}$ hydrocarbons and hydrogen can comprise (a) introducing a reactant mixture to a reactor, wherein the reactant mixture comprises methane ($CH_4$), wherein the reactor comprises a plurality of reactor tubes of varying diameters in a concentric placement (e.g., "tube in tube"

structure/design), wherein each reactor tube can be a reactor tube as described for FIG. 7A, wherein the reactor comprises a preheat zone, a catalyzed reaction zone (e.g., a primary reaction zone comprising at least one catalytic tube), an uncatalyzed reaction zone (e.g., a secondary reaction zone), and a quench zone; (b) heating the reactant mixture ($Q1_{in}$) to a preheating temperature in the preheat zone to yield a heated reactant mixture, wherein the preheat zone comprises a heat exchanger for heating the reactant mixture; (c) contacting at least a portion of the heated reactant mixture with the at least one catalytic tube in the catalyzed reaction zone to form a catalyst effluent mixture comprising free radicals, hydrocarbons, hydrogen and unreacted methane, wherein the catalyzed reaction zone is characterized by a catalyzed reaction zone temperature, wherein the catalyzed reaction zone is heated to the catalyzed reaction zone temperature ($Q2_{in}$), wherein the catalyzed reaction zone temperature is greater than the preheating temperature, wherein the catalyzed reaction zone comprises a heat exchanger for heating the catalyzed reaction zone, and wherein the catalytic tube and/or an inner catalytic tube surface in the catalyzed reaction zone is partially or entirely manufactured from and/or surface coated with a catalyst (e.g., catalyst material); (d) reacting at least a portion of the catalyst effluent mixture in the uncatalyzed reaction zone to form a reaction zone effluent mixture comprising $C_{2+}$ hydrocarbons, hydrogen, free radicals, and unreacted methane, wherein the uncatalyzed reaction zone is characterized by an uncatalyzed reaction zone temperature, wherein the uncatalyzed reaction zone is heated to the uncatalyzed reaction zone temperature ($Q3_{in}$), wherein the uncatalyzed reaction zone comprises a heat exchanger to heat the uncatalyzed reaction zone, and wherein at least a portion of an uncatalyzed reaction zone surface reacts with at least a portion of the catalyst effluent mixture to form a reaction zone effluent mixture; (e) cooling at least a portion of the reaction zone effluent mixture ($Q4_{out}$) in the quench zone to a quench temperature to yield a product mixture comprising $C_{2+}$ hydrocarbons, hydrogen, and unreacted methane, wherein the quench temperature is lower than the uncatalyzed reaction zone temperature, and wherein the quench zone comprises a heat exchanger to cool the quench zone; and (f) recovering at least a portion of the product mixture from the reactor. While the embodiment of FIG. 7B describes concentric placement of three reactor tubes, it should be understood that any suitable number of concentrically placed tubes can be used for producing $C_{2+}$ hydrocarbons and hydrogen, such as for example 2, 3, 4, 5, 6, 7, 8, 9, 10, or more concentrically placed tubes can be used for producing $C_{2+}$ hydrocarbons and hydrogen.

Figure 8A:
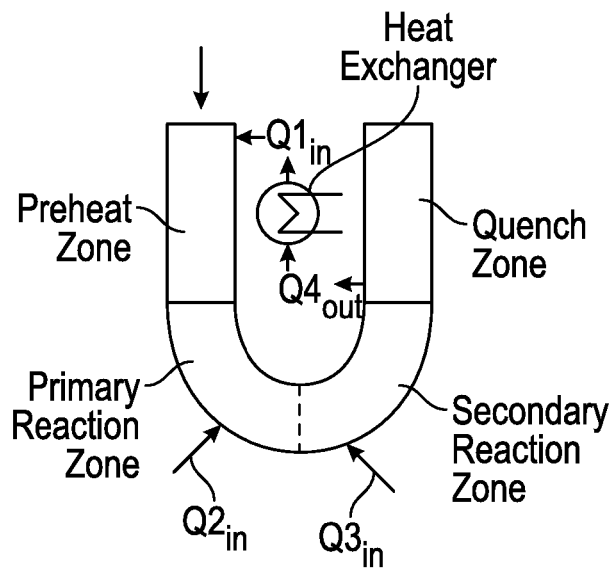
FIG. 8A displays a schematic of a reactor design of an "U" shaped reactor comprising a preheat zone, a primary reaction zone comprising a catalyst, a secondary reaction zone, and a quench zone, indicating heat input (Qi) and heat transfer management.

Referring to the embodiment of FIG. 8A, a method for producing $C_{2+}$ hydrocarbons and hydrogen can comprise (a) introducing a reactant mixture to a "U" shaped reactor, wherein the reactant mixture comprises methane ($CH_4$), wherein the reactor comprises a preheat zone, a catalyzed reaction zone (e.g., a primary reaction zone comprising a catalytic tube), an uncatalyzed reaction zone (e.g., a secondary reaction zone), and a quench zone; (b) heating the reactant mixture ($Q1_{in}$) to a preheating temperature in the preheat zone to yield a heated reactant mixture, wherein the preheat zone comprises a heat exchanger for heating the reactant mixture by recycling at least a portion of heat produced from the quench zone; (c) contacting at least a portion of the heated reactant mixture with the catalytic tube in the catalyzed reaction zone to form a catalyst effluent mixture comprising free radicals, hydrocarbons, hydrogen and unreacted methane, wherein the catalyzed reaction zone is characterized by a catalyzed reaction zone temperature, wherein the catalyzed reaction zone is heated to the catalyzed reaction zone temperature ($Q2_{in}$), wherein the catalyzed reaction zone temperature is greater than the preheating temperature, wherein the catalyzed reaction zone comprises a heat exchanger for heating the catalyzed reaction zone, and wherein the catalytic tube and/or an inner catalytic tube surface in the catalyzed reaction zone is partially or entirely manufactured from and/or surface coated with a catalyst (e.g., catalyst material); (d) reacting at least a portion of the catalyst effluent mixture in the uncatalyzed reaction zone to form a reaction zone effluent mixture comprising $C_{2+}$ hydrocarbons, hydrogen, free radicals, and unreacted methane, wherein the uncatalyzed reaction zone is characterized by an uncatalyzed reaction zone temperature, wherein the uncatalyzed reaction zone is heated to the uncatalyzed reaction zone temperature ($Q3_{in}$), wherein the uncatalyzed reaction zone comprises a heat exchanger to heat the uncatalyzed reaction zone, and wherein at least a portion of an uncatalyzed reaction zone surface reacts with at least a portion of the catalyst effluent mixture to form a reaction zone effluent mixture; (e) cooling at least a portion of the reaction zone effluent mixture ($Q4_{out}$) in the quench zone to a quench temperature to yield a product mixture comprising $C_{2+}$ hydrocarbons, hydrogen, and unreacted methane, wherein the quench temperature is lower than the uncatalyzed reaction zone temperature, and wherein the quench zone inputs heat into the heat exchanger of preheat zone to cool the quench zone; and (f) recovering at least a portion of the product mixture from the reactor. As will be appreciated by one of skill in the art, and with the help of this disclosure, the "U" shape of the reactor allows for the preheat zone and the quench zone to be closer spatially to each other, thereby allowing for a more efficient heat transfer from the quench zone to the preheat zone. The heat recovered from the quench zone could be further used for heating the primary reaction zone and/or the secondary reaction zone.

Figure 8B:
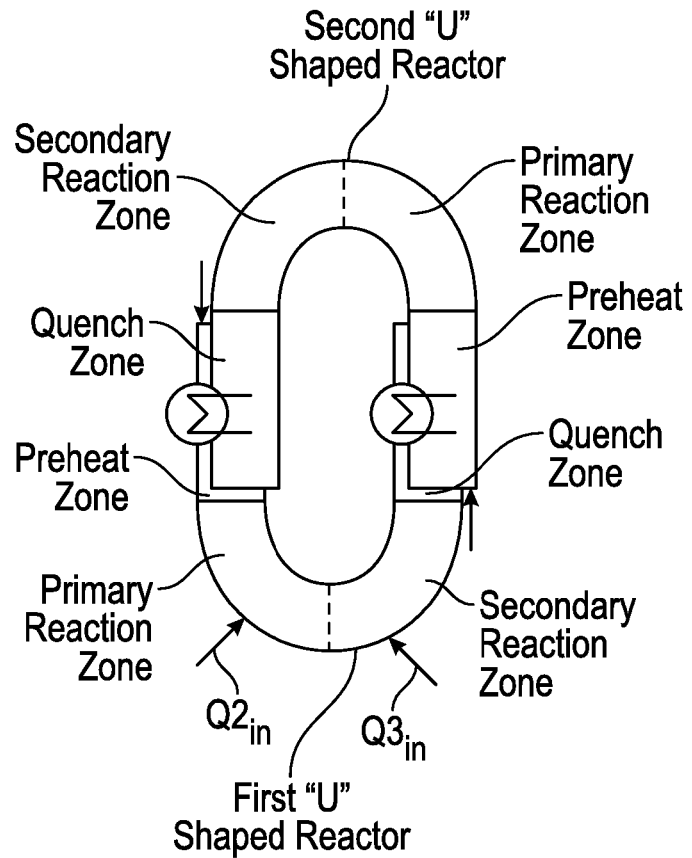
FIG. 8B displays a schematic of a reactor design for a reactor system comprising two "U" shaped reactors of FIG. 8A.

Referring to the embodiment of FIG. 8B, a method for producing $C_{2+}$ hydrocarbons and hydrogen can comprise (a) introducing a reactant mixture to a double "U" shaped reactor system; wherein the reactant mixture comprises methane ($CH_4$); wherein the double "U" shaped reactor system comprises a first "U" shaped reactor and a second "U" shaped reactor; wherein each of the first and the second "U" shaped reactors comprises a preheat zone, a catalyzed reaction zone (e.g., a primary reaction zone comprising a catalytic tube), an uncatalyzed reaction zone (e.g., a secondary reaction zone), and a quench zone; (b) heating the reactant mixture ($Q1_{in}$) to a preheating temperature in the preheat zone to yield a heated reactant mixture, wherein the preheat zone comprises a heat exchanger, wherein the preheat zone of the first "U" shaped reactor is heated with a heat exchanger receiving heat recycled from the quench zone of the second "U" shaped reactor, and wherein the preheat zone of the second "U" shaped reactor is heated with a heat exchanger receiving heat recycled from the quench zone of the first "U" shaped reactor; (c) contacting at least a portion of the heated reactant mixture with the catalytic tube in the catalyzed reaction zone to form a catalyst effluent mixture comprising free radicals, hydrocarbons, hydrogen and unreacted methane, wherein the catalyzed reaction zone is characterized by a catalyzed reaction zone temperature, wherein the catalyzed reaction zone is heated to the catalyzed reaction zone temperature ($Q2_{in}$), wherein the catalyzed reaction zone temperature is greater than the preheating temperature, wherein the catalyzed reaction zone comprises a heat exchanger for heating the catalyzed reaction zone, and wherein the catalytic tube and/or an inner catalytic tube surface in the catalyzed reaction zone is partially or entirely manufactured from and/or surface coated with a catalyst (e.g., catalyst material); (d) reacting at least a portion of the catalyst effluent mixture in the uncatalyzed reaction zone to form a reaction zone effluent mixture comprising $C_{2+}$ hydrocarbons, hydrogen, free radicals, and unreacted methane, wherein the uncatalyzed reaction zone is characterized by an uncatalyzed reaction zone temperature, wherein the uncatalyzed reaction zone is heated to the uncatalyzed reaction zone temperature ($Q3_{in}$), wherein the uncatalyzed reaction zone comprises a heat exchanger to heat the uncatalyzed reaction zone, and wherein at least a portion of an uncatalyzed reaction zone surface reacts with at least a portion of the catalyst effluent mixture to form a reaction zone effluent mixture; (e) cooling at least a portion of the reaction zone effluent mixture ($Q4_{out}$) in the quench zone to a quench temperature to yield a product mixture comprising $C_{2+}$ hydrocarbons, hydrogen, and unreacted methane, wherein the quench temperature is lower than the uncatalyzed reaction zone temperature, and wherein the quench zone comprise a heat exchanger for cooling the quench zone, wherein the quench zone of the first "U" shaped reactor recycles heat to a heat exchanger for heating the preheat zone of the second "U" shaped reactor, and wherein the quench zone of the second "U" shaped reactor recycles heat to a heat exchanger for heating the preheat zone of the first "U" shaped reactor; and (f) recovering at least a portion of the product mixture from the reactor.

Figure 8C:
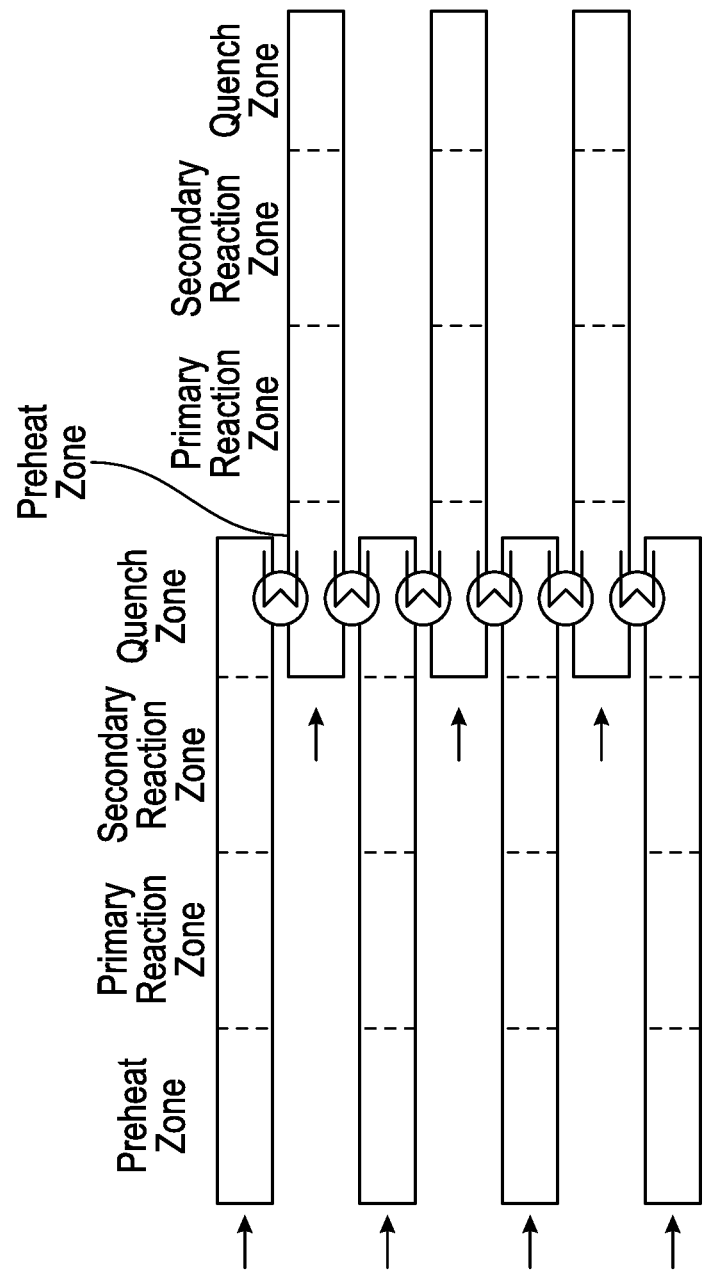
FIG. 8C displays a schematic of a reactor design of tubular reactors in a linear placement, wherein the reactors comprise a preheat zone, a primary reaction zone comprising a catalyst, a secondary reaction zone, and a quench zone, indicating heat input (Qi) and heat transfer management.

Referring to the embodiment of FIG. 8C, a method for producing $C_{2+}$ hydrocarbons and hydrogen can comprise (a) introducing a reactant mixture to a reactor system, wherein the reactor system comprises a plurality of reactors (e.g., reactor tubes), wherein the reactant mixture comprises methane ($CH_4$), wherein each reactor tube comprises a preheat zone, a catalyzed reaction zone (e.g., a primary reaction zone comprising a catalytic tube), an uncatalyzed reaction zone (e.g., a secondary reaction zone), and a quench zone, wherein the reactor tubes are positioned in a parallel manner (e.g., linear placement) with respect to each other, wherein the preheat zone of each reactor is adjacent to at least one quench zone from another reactor, and wherein the preheat zone of each reactor exchanges heat with at least one quench zone from another reactor; (b) heating the reactant mixture ($Q1_{in}$) to a preheating temperature in the preheat zone to yield a heated reactant mixture, wherein the preheat zone comprises a heat exchanger for heating the reactant mixture by recycling the heat from at least one quench zone from another reactor; (c) contacting at least a portion of the heated reactant mixture with the catalytic tube in the catalyzed reaction zone to form a catalyst effluent mixture comprising free radicals, hydrocarbons, hydrogen and unreacted methane, wherein the catalyzed reaction zone is characterized by a catalyzed reaction zone temperature, wherein the catalyzed reaction zone is heated to the catalyzed reaction zone temperature ($Q2_{in}$), wherein the catalyzed reaction zone temperature is greater than the preheating temperature, wherein the catalyzed reaction zone comprises a heat exchanger for heating the catalyzed reaction zone, and wherein the catalytic tube and/or an inner catalytic tube surface in the catalyzed reaction zone is partially or entirely manufactured from and/or surface coated with a catalyst (e.g., catalyst material); (d) reacting at least a portion of the catalyst effluent mixture in the uncatalyzed reaction zone to form a reaction zone effluent mixture comprising $C_{2+}$ hydrocarbons, hydrogen, free radicals, and unreacted methane, wherein the uncatalyzed reaction zone is characterized by an uncatalyzed reaction zone temperature, wherein the uncatalyzed reaction zone is heated to the uncatalyzed reaction zone temperature ($Q3_{in}$), wherein the uncatalyzed reaction zone comprises a heat exchanger to heat the uncatalyzed reaction zone, and wherein at least a portion of an uncatalyzed reaction zone surface reacts with at least a portion of the catalyst effluent mixture to form a reaction zone effluent mixture; (e) cooling at least a portion of the reaction zone effluent mixture ($Q4_{out}$) in the quench zone to a quench temperature to yield a product mixture comprising $C_{2+}$ hydrocarbons, hydrogen, and unreacted methane, wherein the quench temperature is lower than the uncatalyzed reaction zone temperature, wherein the quench zone comprise a heat exchanger for cooling the quench zone, and wherein the quench zone of each reactor exchanges heat with at least one preheat zone from another reactor; and (f) recovering at least a portion of the product mixture from the reactor. As will be appreciated by one of skill in the art, and with the help of this disclosure, the parallel arrangement of reactor tubes allows for preheat zones and quench zones to be closer spatially to each other, thereby allowing for a more efficient heat transfer.

Figure 9A:
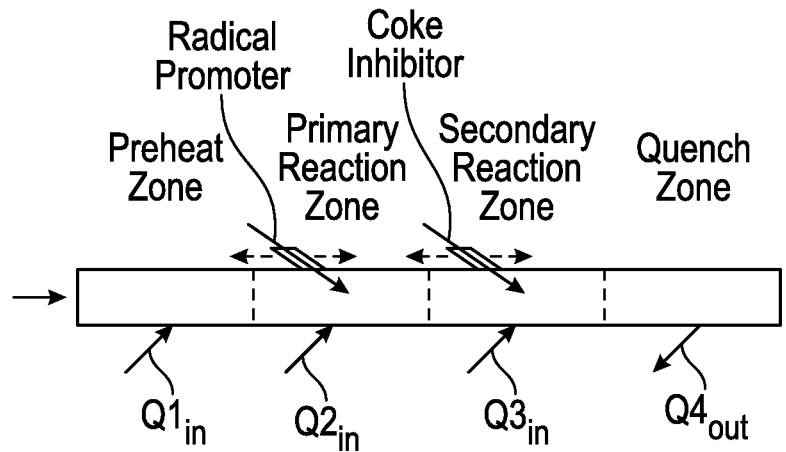
FIG. 9A displays a schematic of a reactor design comprising a preheat zone, a primary reaction zone comprising a catalyst, a secondary reaction zone, and a quench zone, indicating heat input (Qi), wherein additives can be introduced in various reactor zones.

Referring to the embodiment of FIG. 9A, a method for producing $C_{2+}$ hydrocarbons and hydrogen can comprise (a) introducing a reactant mixture to a reactor, wherein the reactant mixture comprises methane ($CH_4$), wherein the reactor comprises a preheat zone, a catalyzed reaction zone (e.g., a primary reaction zone comprising a catalytic tube), an uncatalyzed reaction zone (e.g., a secondary reaction zone), and a quench zone; (b) heating the reactant mixture ($Q1_{in}$) to a preheating temperature in the preheat zone to yield a heated reactant mixture, wherein the preheat zone comprises a heat exchanger for heating the reactant; (c) contacting at least a portion of the heated reactant mixture with the catalytic tube in the catalyzed reaction zone to form a catalyst effluent mixture comprising free radicals, hydrocarbons, hydrogen and unreacted methane, wherein the catalyzed reaction zone is characterized by a catalyzed reaction zone temperature, wherein the catalyzed reaction zone is heated to the catalyzed reaction zone temperature ($Q2_{in}$), wherein the catalyzed reaction zone temperature is greater than the preheating temperature, wherein the catalyzed reaction zone comprises a heat exchanger for heating the catalyzed reaction zone, wherein radical promoters are injected into the catalyzed reaction zone at a desired rate and at a desired position effective to promote radical formation, and wherein the catalytic tube and/or an inner catalytic tube surface in the catalyzed reaction zone is partially or entirely manufactured from and/or surface coated with a catalyst (e.g., catalyst material); (d) reacting at least a portion of the catalyst effluent mixture in the uncatalyzed reaction zone to form a reaction zone effluent mixture comprising $C_{2+}$ hydrocarbons, hydrogen, free radicals, and unreacted methane, wherein the uncatalyzed reaction zone is characterized by an uncatalyzed reaction zone temperature, wherein the uncatalyzed reaction zone is heated to the uncatalyzed reaction zone temperature ($Q3_{in}$), wherein the uncatalyzed reaction zone comprises a heat exchanger to heat the uncatalyzed reaction zone, wherein coke inhibitors are injected into the catalyzed reaction zone at a desired rate and at a desired position effective to inhibit coke formation, and wherein at least a portion of an uncatalyzed reaction zone surface reacts with at least a portion of the catalyst effluent mixture to form a reaction zone effluent mixture; (e) cooling at least a portion of the reaction zone effluent mixture ($Q4_{out}$) in the quench zone to a quench temperature to yield a product mixture comprising $C_{2+}$ hydrocarbons, hydrogen, and unreacted methane, wherein the quench temperature is lower than the uncatalyzed reaction zone temperature; and (f) recovering at least a portion of the product mixture from the reactor.

Figure 9B:
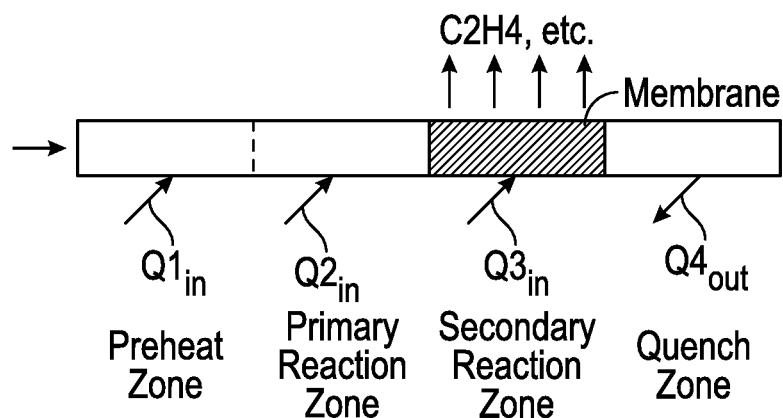
FIG. 9B displays a schematic of a reactor design comprising a preheat zone, a primary reaction zone comprising a catalyst, a secondary reaction zone, and a quench zone, indicating heat input (Qi), wherein products can be separated from the secondary reaction zone via a membrane.
Figure 10A:
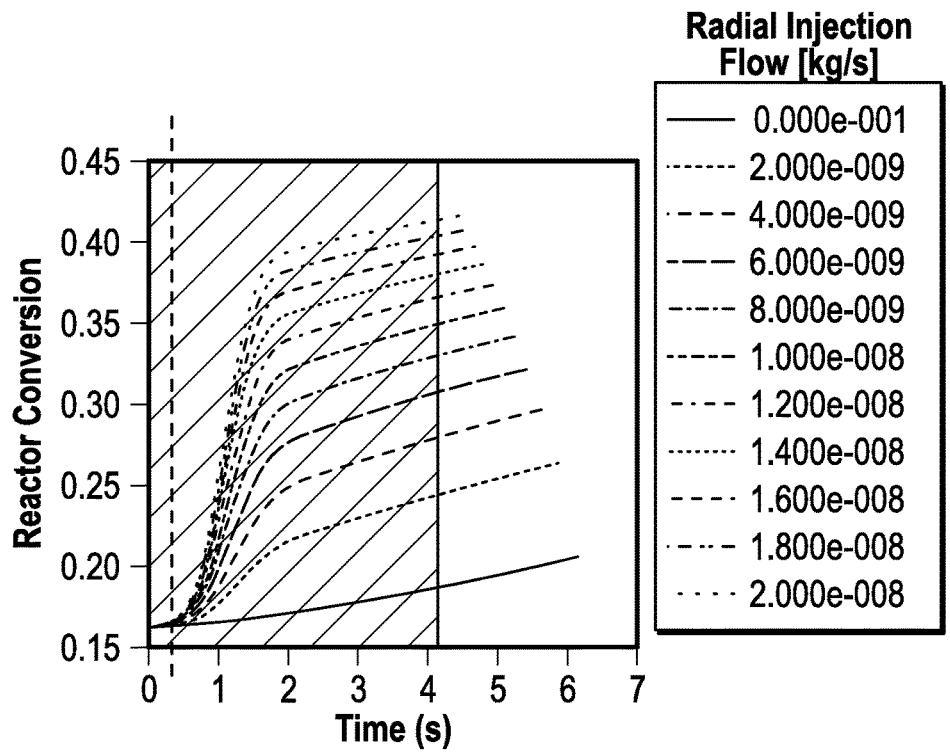
FIG. 10A displays a graph of conversion of methane to methyl radicals as a function of residence time in a reactor.
Figure 10B:
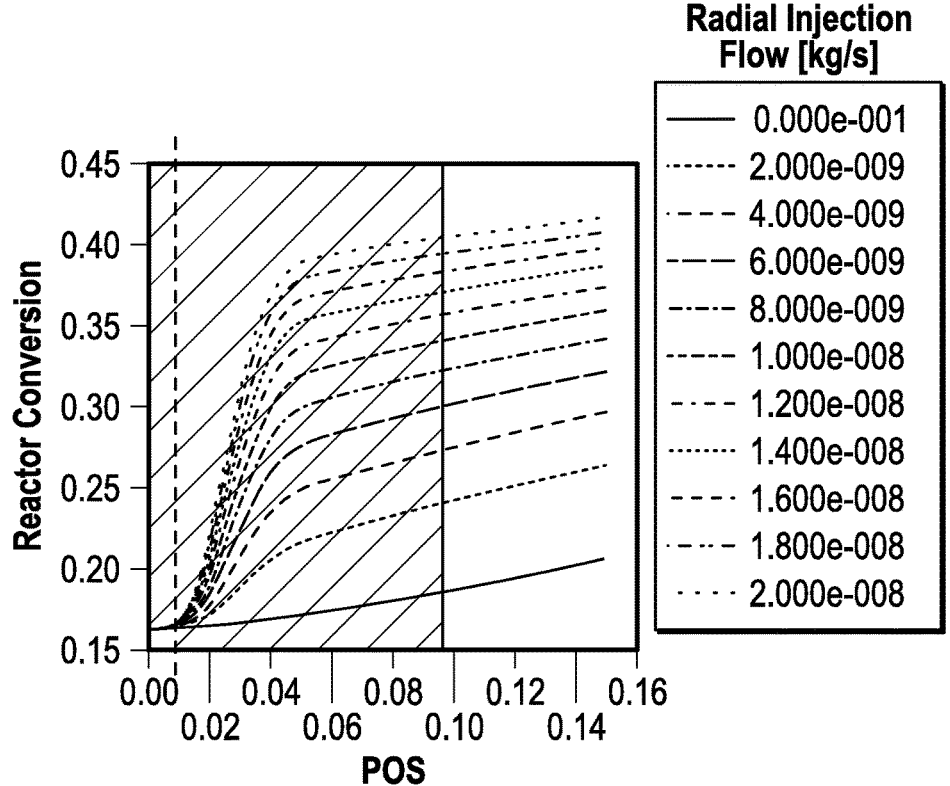
FIG. 10B displays a graph of conversion of methane to methyl radicals as a function of distance in a reactor.
Figure 10C:
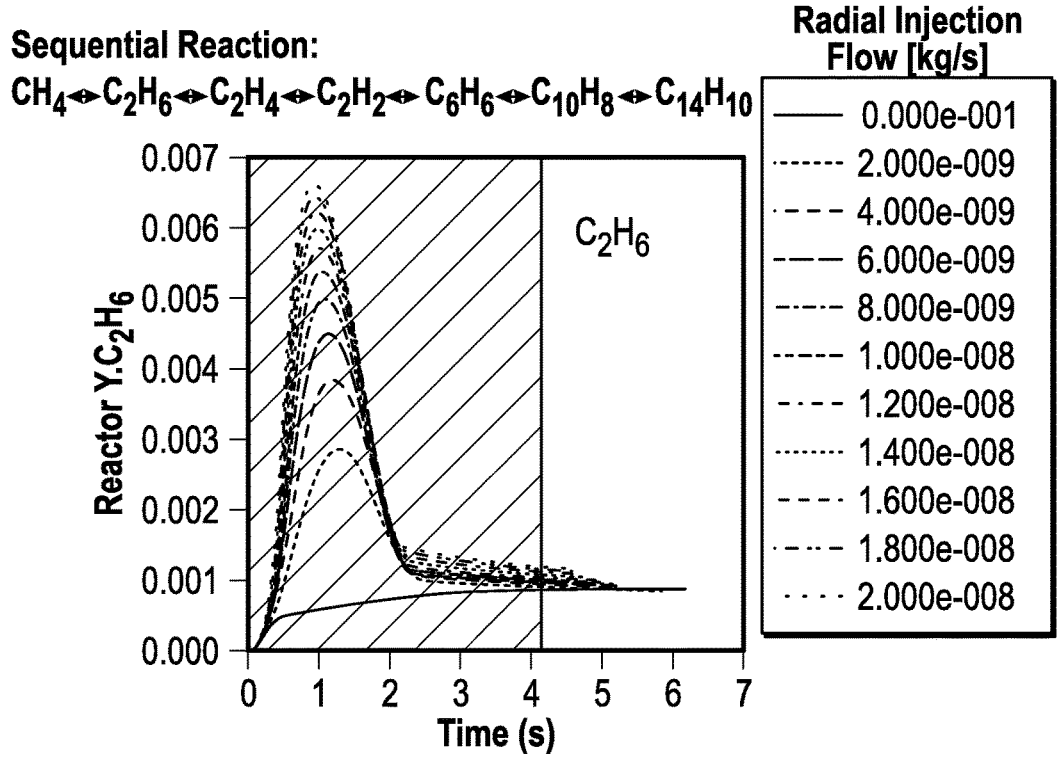
FIGS. 10C-G display graphs of yields of various products as a function of residence time in a reactor.
Figure 10D:
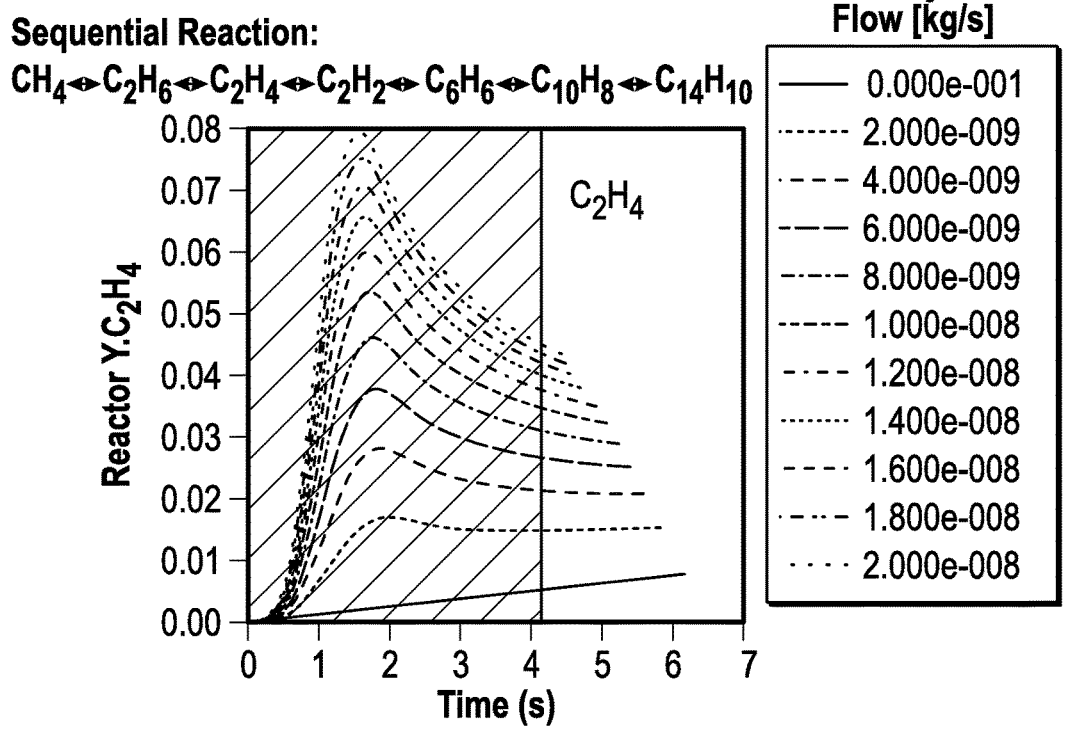
Figure 10E:
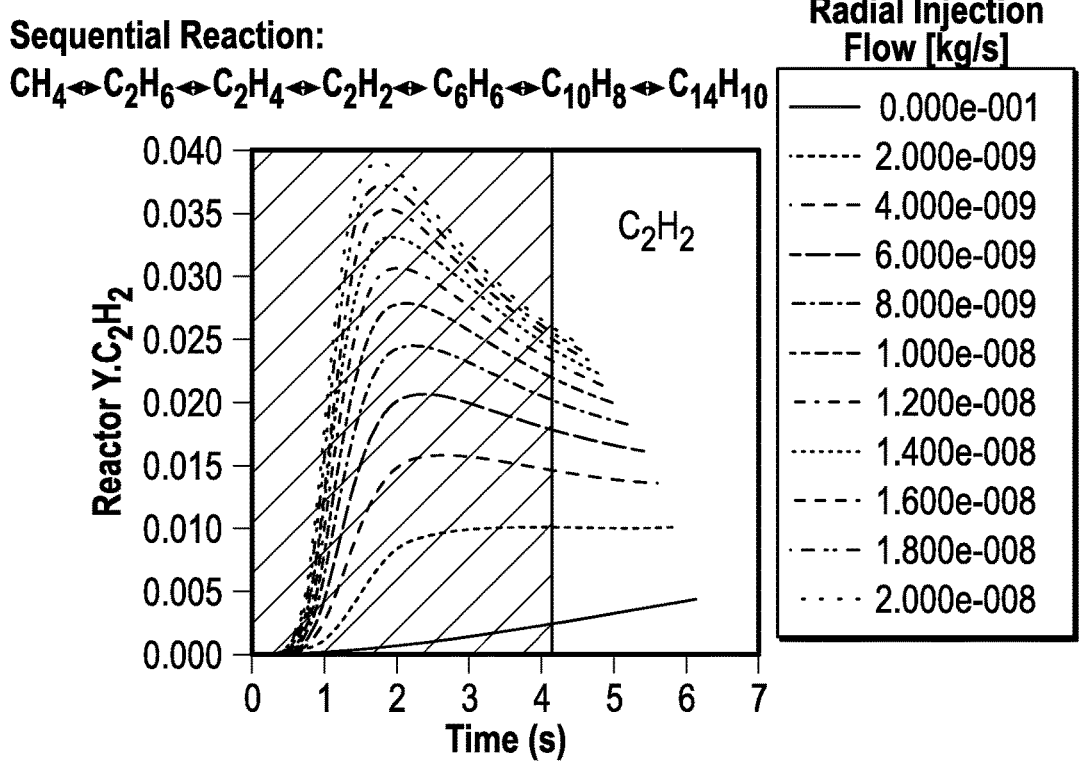
Figure 10F:
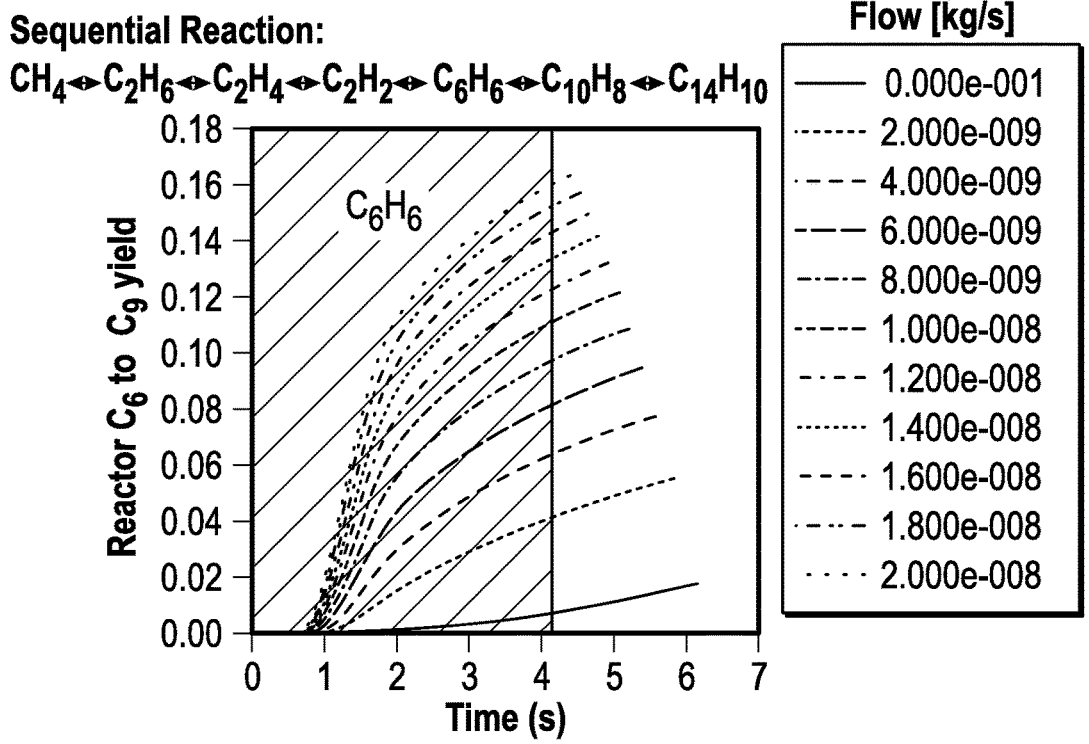
Figure 10G:
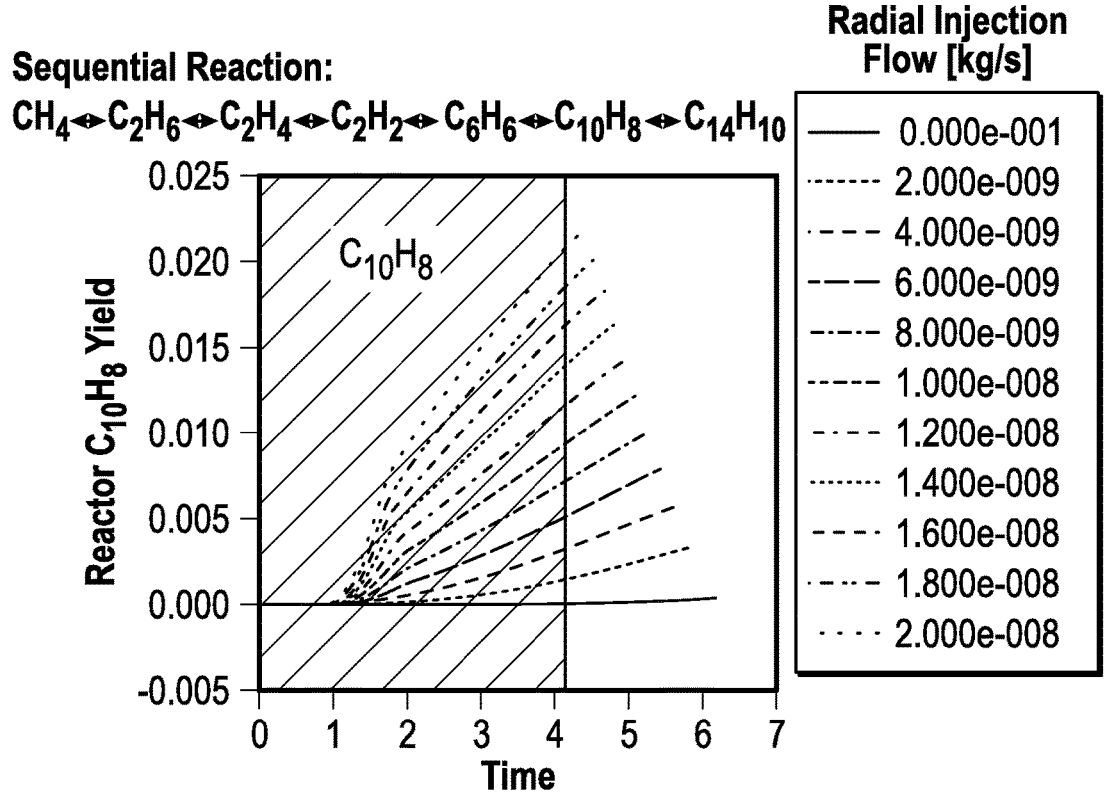
Figure 11:
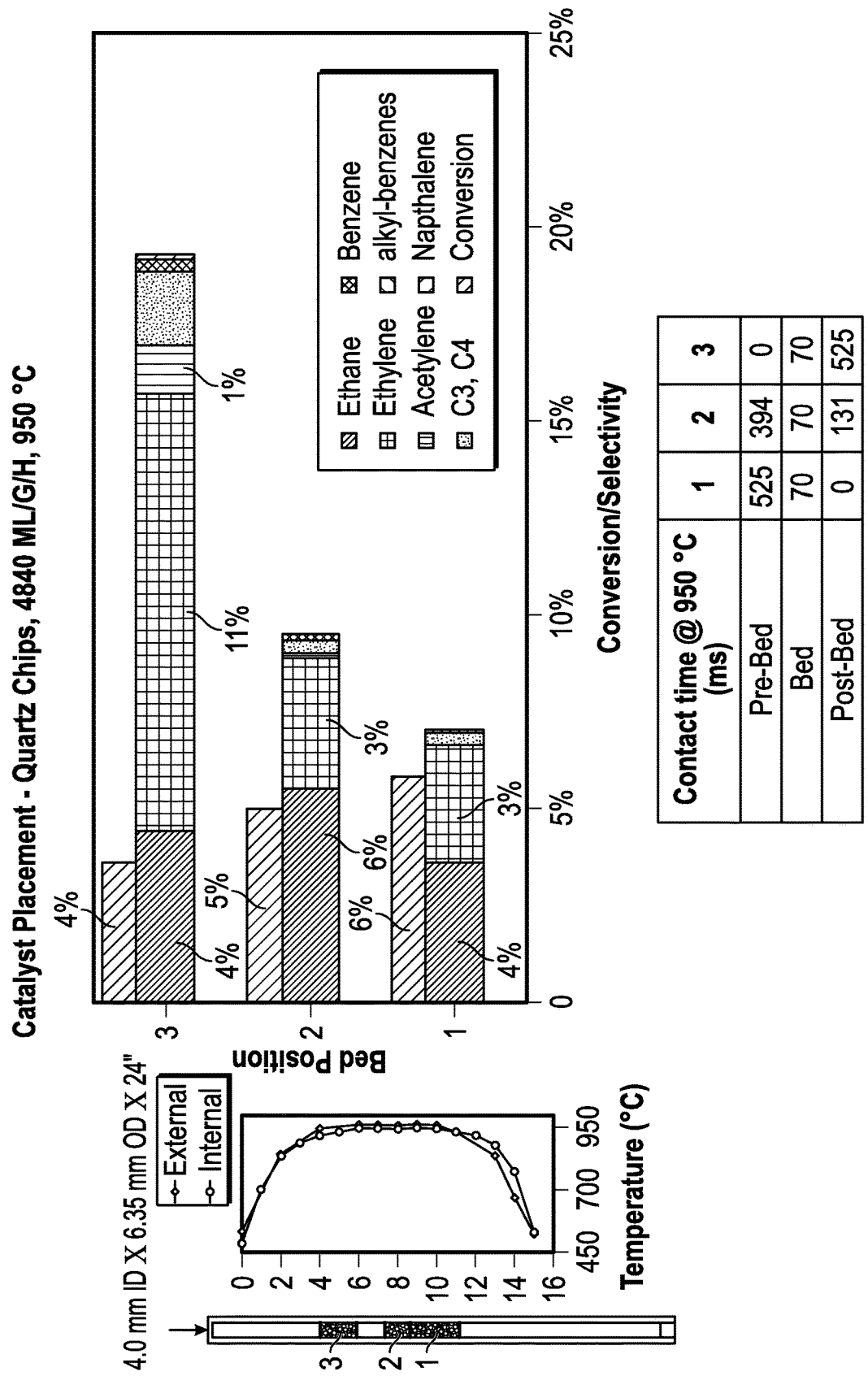
FIG. 11 displays conversion and selectivity results for various quartz chips catalyst placement positions in a reactor at 4,840 ml/g/h and 950° C.
Figure 12:
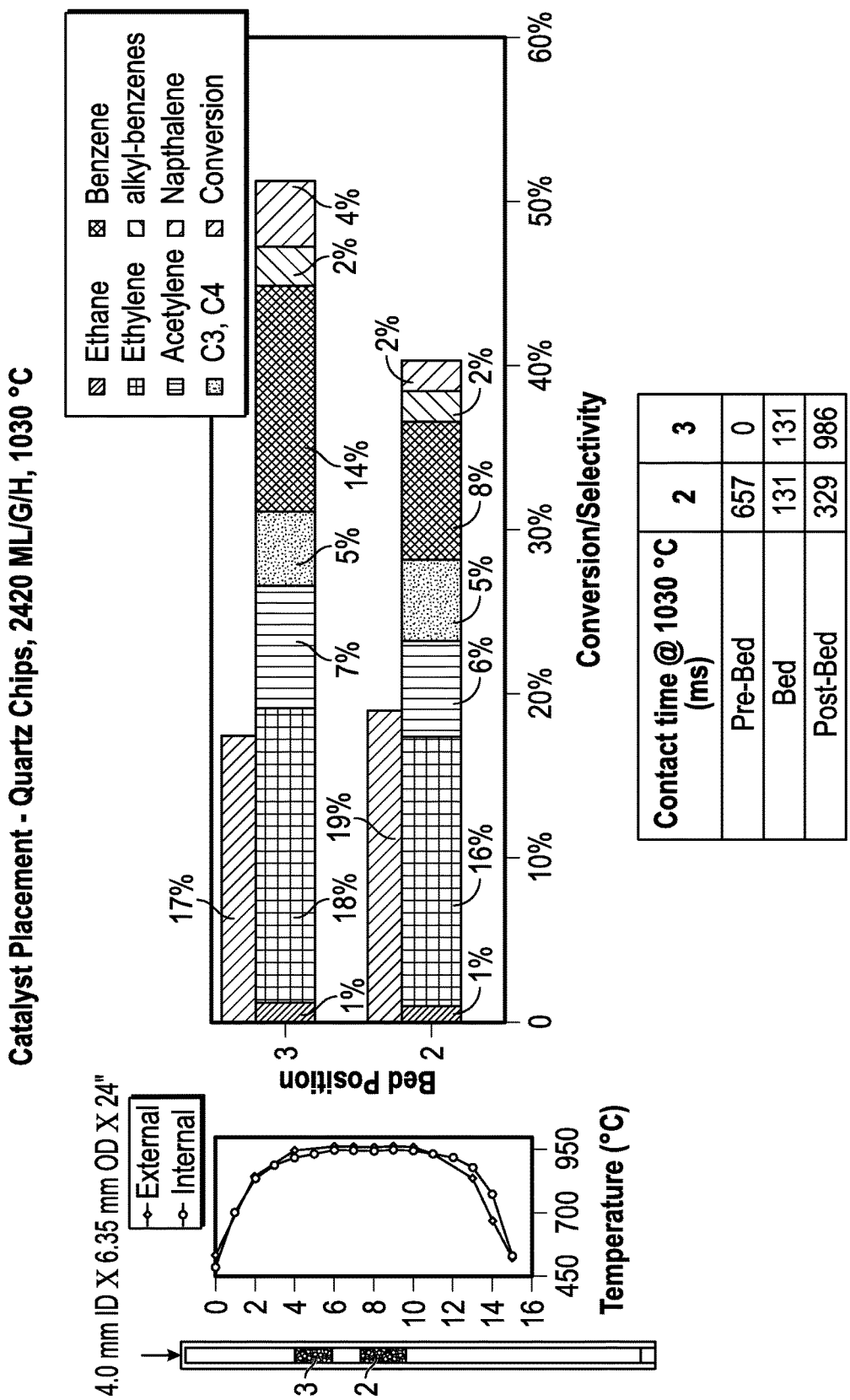
FIG. 12 displays conversion and selectivity results for various quartz chips catalyst placement positions in a reactor at 2,420 ml/g/h and 1,030° C.
Figure 13:
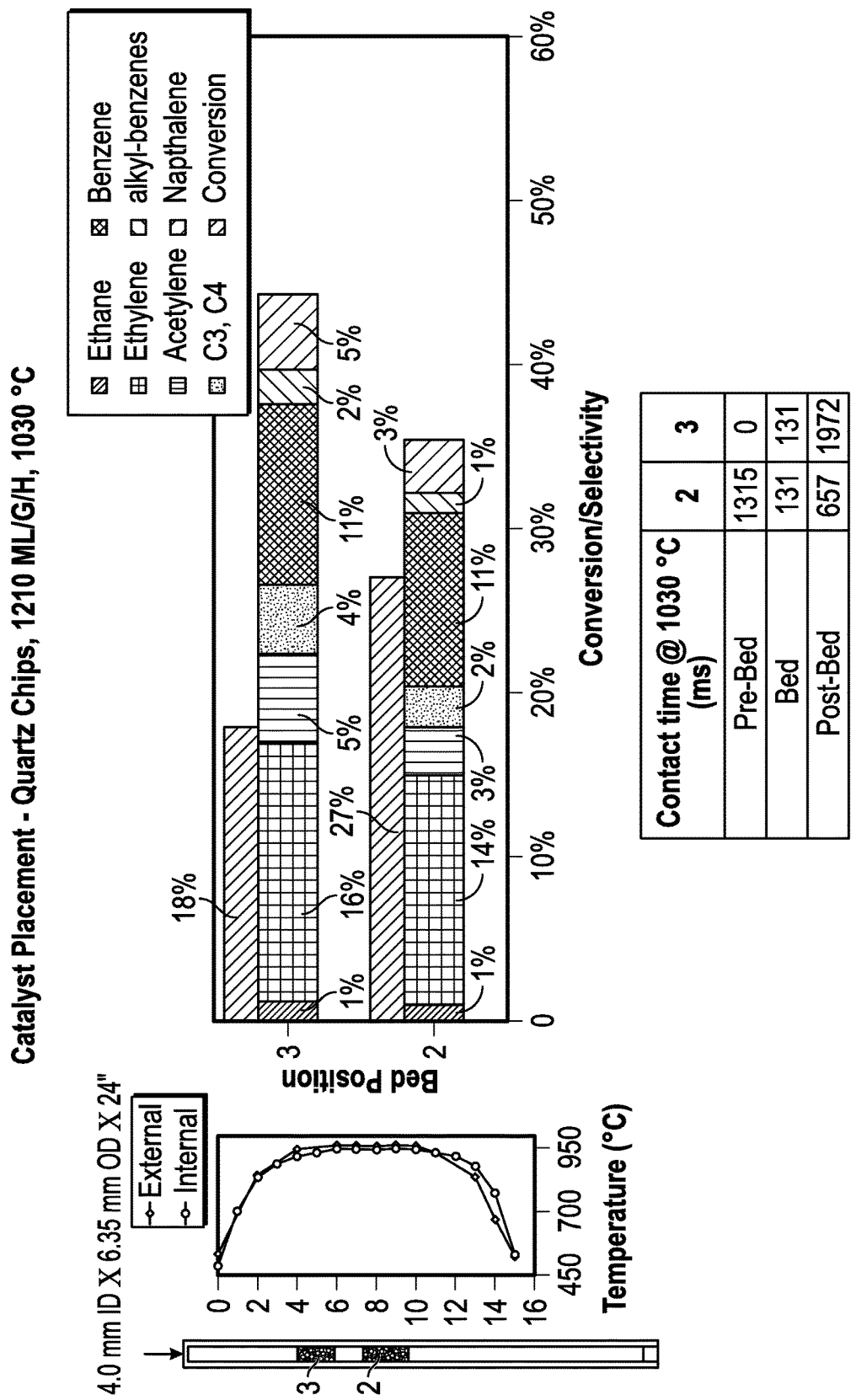
FIG. 13 displays conversion and selectivity results for various quartz chips catalyst placement positions in a reactor at 1,210 ml/g/h and 1,030° C.
Figure 14:
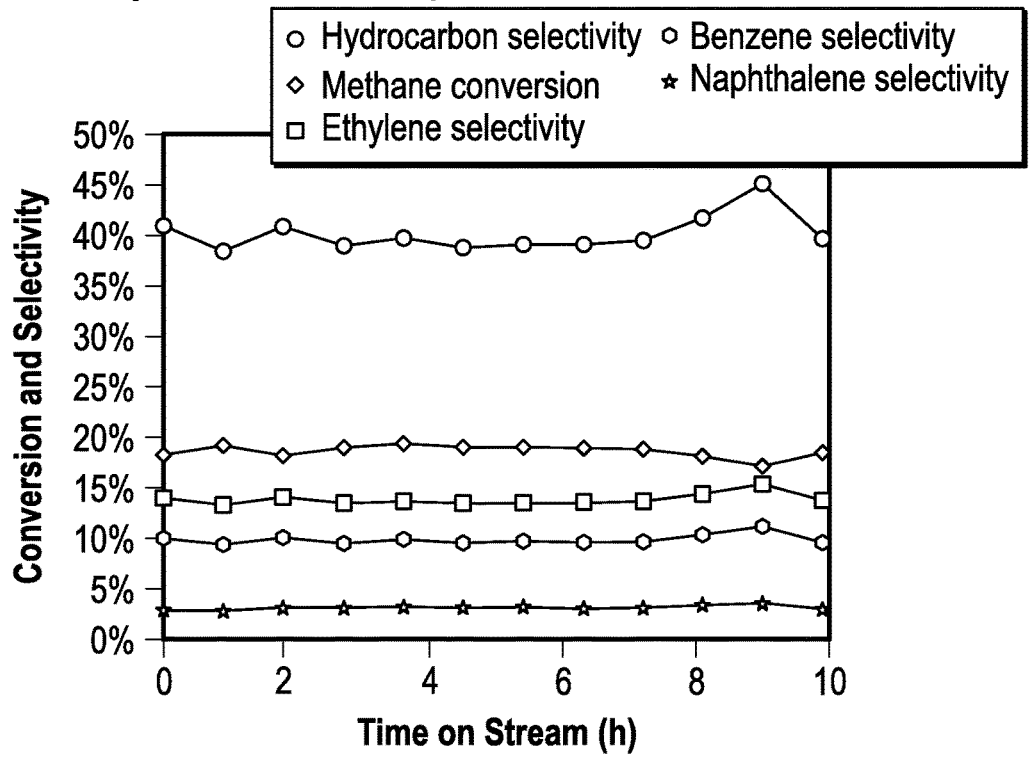
FIG. 14 displays data stability results for conversion and selectivity over time in a reactor at 1,210 ml/g/h and 1,030° C.

Referring to the embodiment of FIG. 9B, a method for producing $C_{2+}$ hydrocarbons and hydrogen can comprise (a) introducing a reactant mixture to a reactor, wherein the reactant mixture comprises methane ($CH_4$), wherein the reactor comprises a preheat zone, a catalyzed reaction zone (e.g., a primary reaction zone comprising a catalytic tube), an uncatalyzed reaction zone (e.g., a secondary reaction zone), and a quench zone; (b) heating the reactant mixture ($Q1_{in}$) to a preheating temperature in the preheat zone to yield a heated reactant mixture, wherein the preheat zone comprises a heat exchanger for heating the reactant mixture; (c) contacting at least a portion of the heated reactant mixture with the catalytic tube in the catalyzed reaction zone to form a catalyst effluent mixture comprising free radicals, hydrocarbons, hydrogen and unreacted methane, wherein the catalyzed reaction zone is characterized by a catalyzed reaction zone temperature, wherein the catalyzed reaction zone is heated to the catalyzed reaction zone temperature ($Q2_{in}$), wherein the catalyzed reaction zone temperature is greater than the preheating temperature, wherein the catalyzed reaction zone comprises a heat exchanger for heating the catalyzed reaction zone, and wherein the catalytic tube and/or an inner catalytic tube surface in the catalyzed reaction zone is partially or entirely manufactured from and/or surface coated with a catalyst (e.g., catalyst material); (d) reacting at least a portion of the catalyst effluent mixture in the uncatalyzed reaction zone to form a reaction zone effluent mixture comprising $C_{2+}$ hydrocarbons, hydrogen, free radicals, and unreacted methane, wherein the uncatalyzed reaction zone is characterized by an uncatalyzed reaction zone temperature, wherein the uncatalyzed reaction zone is heated to the uncatalyzed reaction zone temperature ($Q3_{in}$), wherein the uncatalyzed reaction zone comprises a heat exchanger to heat the uncatalyzed reaction zone, and wherein at least a portion of the uncatalyzed reaction zone and/or the quench zone comprises a high temperature resistance membrane to separate and recover at least a portion of olefins (e.g., $C_2H_4$) or at least a portion of the hydrogen, thereby enhancing conversion and/or selectivity; (e) cooling at least a portion of the reaction zone effluent mixture ($Q4_{out}$) in the quench zone to a quench temperature to yield a product mixture comprising $C_{2+}$ hydrocarbons, hydrogen, and unreacted methane, wherein the quench temperature is lower than the uncatalyzed reaction zone temperature; and (f) recovering at least a portion of the product mixture from the reactor.

In an embodiment, a method for producing $C_{2+}$ hydrocarbons (e.g., ethylene, benzene, etc.) and hydrogen as disclosed herein can advantageously display improvements in one or more method characteristics when compared to an otherwise similar method lacking using a reactor as disclosed herein. In an embodiment, a reactor design as disclosed herein can advantageously allow for selective conversion of methane to hydrocarbons such as olefins, high alkanes, and aromatic hydrocarbons, wherein formation of alkynes and "coke" can be minimized. Generally, coke refers to an agglomeration of material such as carbon deposits on a surface (e.g., catalyst surface, inner reactor surface, etc.).

In an embodiment, a method for producing $C_{2+}$ hydrocarbons (e.g., ethylene, benzene, etc.) and hydrogen as disclosed herein can advantageously achieve higher selectivities and yields to desired hydrocarbons by using a reactor that addresses the important interplay between reactor design, catalytic reactions and gas phase reactions.

In an embodiment, a method for producing $C_{2+}$ hydrocarbons (e.g., ethylene, benzene, etc.) and hydrogen as disclosed herein can advantageously minimize or eliminate homogeneous uncatalyzed pyrolysis of $CH_4$ to produce acetylene and carbon-based products such as soot, and coke, by maintaining a secondary reaction zone temperature in the secondary reaction zone (e.g., uncatalyzed secondary reaction zone) as disclosed herein.

In an embodiment, reactor designs as disclosed herein can advantageously allow flexibility in a product mixture composition (e.g., controlling relative amounts of $C_{2+}$ hydrocarbons and aromatic hydrocarbons such as benzene) by adjusting reactor process conditions (e.g., temperature, residence time, quenching rates, etc.). In such embodiment, the flexibility of product mixture composition can advantageously meet the changing needs for feedstocks for different industries. Yields of olefins and aromatics from the alkane feedstock can be adjusted to the desired, most efficient, numbers depending on market needs and process economics.

In an embodiment, a method for producing $C_{2+}$ hydrocarbons (e.g., ethylene, benzene, etc.) and hydrogen as disclosed herein can be advantageously conducted in parallel with a steam cracker so as to "feed" into the downstream separation units of the steam cracker. In such embodiment, depending on pricing of natural gas to ethane, a feedstock of choice for the desired ethylene and/or propylene could be balanced.

In an embodiment, a method for producing $C_{2+}$ hydrocarbons (e.g., ethylene, benzene, etc.) and hydrogen as disclosed herein can advantageously allow for efficiently utilizing the availability of a wide variety of feedstocks for the reactant mixture, by adjusting and optimizing reactor conditions.

In an embodiment, a method for producing $C_{2+}$ hydrocarbons (e.g., ethylene, benzene, etc.) and hydrogen as disclosed herein can advantageously lead to a high selectivity to ethylene and hydrocarbons (e.g., enabled by reactor and process design). In such embodiment, heat input can be advantageously reduced substantially, thereby lowering overall energy costs and improving process economics of the method. With the reduction of the heat input due to higher selectivity to ethylene and low or no production of "coke," lower amounts of $CO_2$ can be produced, making this a greener process, and the process economics could be less susceptible to a $CO_2$ tax.

In an embodiment, reactor designs as disclosed herein can advantageously enable the development of non-syngas-based routes to transform light hydrocarbons into higher value-added chemicals and fuels, by using efficient reactor technology. If the process is operated at moderate single pass conversions, the unreacted methane and other alkanes can be used as fuel and burned with or without the hydrogen once the olefins and aromatics are removed, thereby helping the energy balance of the process.

In an embodiment, a method for producing $C_{2+}$ hydrocarbons (e.g., ethylene, benzene, etc.) and hydrogen as disclosed herein can advantageously allow for this method to be "mobile," due to a process simplicity, and as such the method could make use of stranded natural gas. Additional advantages of the methods for the production of $C_{2+}$ hydrocarbons (e.g., ethylene, benzene, etc.) and hydrogen as disclosed herein can be apparent to one of skill in the art viewing this disclosure.

EXAMPLES

The subject matter having been generally described, the following examples are given as particular embodiments of the disclosure and to demonstrate the practice and advantages thereof. It is understood that the examples are given by way of illustration and are not intended to limit the specification of the claims to follow in any manner.

Example 1

The formation of methyl radicals in a non-oxidative coupling of methane reaction a reactor was mathematically modeled by using a Roscoe-Thompson mechanism for calculating concentration-time profiles, as described in more detail in J. Phys. Chem. 1990, 94, 1432-1439, which is incorporated by reference herein in its entirety. The kinetics of $.CH_3$ accumulation were considered for the model. The experimental data were also compared with the results from the model, indicating that at conditions which were used experimentally (4.1 seconds reactor residence time, 0.03 seconds catalyst zone contact time (e.g., residence time of the chemical species in the catalyst bed)), product distribution fits the model used for prediction of experimental data.

The results of the modeling are displayed in FIGS. 10A-G. These modeling results show that the release of methyl radicals into the gas phase can lead to high methane conversions at 1030° C. The various curves are representative of methane conversion relative to the different rates of methyl radicals being released into a hydrocarbon stream. The concentration of the methyl radicals generated in the primary reaction zone and released into the gas phase into the secondary reaction zone is controlled by many factors, including the temperature, the flow rate through the reactor, pressure, the catalyst composition and design, and the reactor design.

Further, as it can be seen from FIGS. 10C-G, the product selectivity was controlled by residence time in the gas phase in the secondary reaction zone. Approximately a 1 second residence time in the secondary reaction zone at 1030° C. can give a product mixture containing ethane, ethylene, acetylene, and benzene as the major products, and naphthalene can be minimized. If the residence time at 1030° C. was doubled to 2 seconds, the conversion of methane could increase and the observed selectivity to ethane would drop to nearly zero, while the selectivities to ethylene, acetylene, benzene and naphthalene would increase. The data show that the residence time effect on the product distribution is dependent on the amount of alkyl radicals in the gas phase. The higher the level of methyl radicals, the shorter the residence times necessary for producing the maximum yield of ethane, ethylene and acetylene. Therefore, controlling the residence time can control product distribution.

Example 2

Non-oxidative coupling of methane reactions were investigated for fine catalyst particles in a continuous flow, fixed bed reactor with an internal volume of 0.117 mL, wherein the fixed catalyst bed was a thin bed with a 3-4 mm bed length. 0.1 g of fine catalyst particles (e.g., fused $Fe_2SiO_4$/$SiO_2$ fine powder) with an average size of 400-635 mesh was packed in the primary reaction zone of the reactor on a bed of quartz wool/felt, unless otherwise stated. The reactor was heated to 950° C. under Ar and then the feed gas was turned on at the appropriate flowrate. The catalyst was activated under these conditions for two hours before introducing a reactant mixture to the reactor. A feed gas (reactant mixture) contained 90 vol. % $CH_4$ and 10 vol. % $N_2$, wherein the $N_2$ in the feed gas was used as internal standard. The effluent composition (product mixture) was monitored by an online Gas Chromatography (GC) (Agilent 7890B), equipped with a flame ionization detector (FID) with CP-SilicaPlot capillary column; a thermal conductivity detector (TCD) with ShinCarbon ST packed column. Conversion, selectivities and yields are displayed in Tables 1, 2, and 3. SV=space velocity, which represents a gas flow rate per unit catalyst amount, and can be expressed as mL of inlet gas per g of catalyst per hour (mL/g/h). The space time yield (STY) refers to a quantity of product [g] produced per quantity of catalyst [kg] per unit time [h] and can be expressed in g/kg/h.

TABLE 1

|  | Temperature (° C.) | 950 | 980 | 1000 | 1020 | 1030 |
|---|---|---|---|---|---|---|
|  | SV (mL/g/h) | 4840 | 6600 | 10000 | 12500 | 14000 |
|  | Conversion | 11.1% | 11.0% | 10.6% | 12.6% | 10.9% |
| Selectivity | ethane | 0.7% | 2.0% | 2.1% | 1.9% | 2.0% |
|  | ethylene | 7.5% | 24.0% | 25.7% | 25.0% | 26.3% |
|  | acetylene | 1.0% | 5.3% | 6.9% | 6.9% | 7.4% |
|  | propane | 0.0% | 0.0% | 0.0% | 0.0% | 0.0% |
|  | propylene | 0.8% | 2.0% | 2.4% | 1.9% | 2.3% |
|  | i-butane | 0.1% | 0.1% | 0.4% | 0.1% | 0.3% |
|  | n-butane | 0.0% | 0.0% | 0.0% | 0.0% | 0.0% |
|  | 1-butene | 0.0% | 0.0% | 1.2% | 0.9% | 1.2% |
|  | (trans-2, i)-Butene | 0.2% | 0.5% | 0.6% | 0.5% | 0.6% |
|  | cis-Butene | 0.0% | 0.0% | 0.0% | 0.0% | 0.0% |
|  | pentane | 0.0% | 0.0% | 0.0% | 0.0% | 0.0% |
|  | benzene | 10.6% | 34.2% | 35.9% | 38.1% | 38.5% |
|  | toluene | 1.4% | 3.6% | 4.3% | 3.8% | 4.4% |
|  | ethyl-benzene | 0.0% | 0.0% | 0.0% | 0.0% | 0.0% |
|  | xylene | 0.3% | 0.9% | 1.2% | 1.1% | 1.2% |
|  | trimethyl-benzene | 0.2% | 0.0% | 0.0% | 0.0% | 0.0% |
|  | naphthalene | 3.3% | 11.6% | 12.2% | 13.1% | 13.1% |
|  | Total | 25.3% | 82.3% | 90.7% | 91.5% | 95.3% |

TABLE 2

|  | Temperature (° C.) | 950 | 980 | 1000 | 1020 | 1030 |
|---|---|---|---|---|---|---|
|  | SV (mL/g/h) | 4840 | 6600 | 10000 | 12500 | 14000 |
|  | Conversion | 11.1% | 11.0% | 10.6% | 12.6% | 10.9% |
| Yield | ethane | 0.1% | 0.2% | 0.2% | 0.2% | 0.2% |

TABLE 2-continued

|  |  |  |  |  |  |
|---|---|---|---|---|---|
| ethylene | 0.8% | 2.7% | 2.7% | 3.1% | 2.9% |
| acetylene | 0.1% | 0.6% | 0.7% | 0.9% | 0.8% |
| propane | 0.0% | 0.0% | 0.0% | 0.0% | 0.0% |
| propylene | 0.1% | 0.2% | 0.2% | 0.2% | 0.3% |
| i-butane | 0.0% | 0.0% | 0.0% | 0.0% | 0.0% |
| n-butane | 0.0% | 0.0% | 0.0% | 0.0% | 0.0% |
| 1-butene | 0.0% | 0.0% | 0.1% | 0.1% | 0.1% |
| (trans-2, i)-Butene | 0.0% | 0.1% | 0.1% | 0.1% | 0.1% |
| cis-Butene | 0.0% | 0.0% | 0.0% | 0.0% | 0.0% |
| pentane | 0.0% | 0.0% | 0.0% | 0.0% | 0.0% |
| benzene | 1.2% | 3.8% | 3.8% | 4.8% | 4.2% |
| toluene | 0.2% | 0.4% | 0.5% | 0.5% | 0.5% |
| ethyl-benzene | 0.0% | 0.0% | 0.0% | 0.0% | 0.0% |
| xylene | 0.0% | 0.1% | 0.1% | 0.1% | 0.1% |
| trimethyl-benzene | 0.0% | 0.0% | 0.0% | 0.0% | 0.0% |
| naphthalene | 0.4% | 1.3% | 1.3% | 1.6% | 1.4% |
| Total | 2.8% | 9.1% | 9.6% | 11.5% | 10.4% |

TABLE 3

|  |  |  |  |  |  |  |
|---|---|---|---|---|---|---|
|  | Temperature (° C.) | 950 | 980 | 1000 | 1020 | 1030 |
|  | SV (mL/g/h) | 4840 | 6600 | 10000 | 12500 | 14000 |
|  | Conversion | 11.1% | 11.0% | 10.6% | 12.6% | 10.9% |
| STY (g/kg/h) | ethane | 2.3 | 8.8 | 13.1 | 17.8 | 18.5 |
|  | ethylene | 22.6 | 98.4 | 152.7 | 220.4 | 226.9 |
|  | acetylene | 2.8 | 20.3 | 38.3 | 56.4 | 59.1 |
|  | propane | 0.0 | 0.0 | 0.0 | 0.0 | 0.0 |
|  | propylene | 2.4 | 8.1 | 14.0 | 17.2 | 20.0 |
|  | i-butane | 0.2 | 0.3 | 2.2 | 0.9 | 2.4 |
|  | n-butane | 0.0 | 0.0 | 0.0 | 0.0 | 0.0 |
|  | 1-butene | 0.1 | 0.1 | 6.9 | 8.3 | 10.0 |
|  | (trans-2, i)-Butene | 0.6 | 1.9 | 3.3 | 4.3 | 4.9 |
|  | cis-Butene | 0.0 | 0.1 | 0.1 | 0.1 | 0.2 |
|  | pentane | 0.0 | 0.0 | 0.0 | 0.0 | 0.0 |
|  | benzene | 29.5 | 130.4 | 197.9 | 312.4 | 308.2 |
|  | toluene | 3.9 | 13.9 | 24.2 | 31.7 | 35.7 |
|  | ethyl-benzene | 0.0 | 0.0 | 0.0 | 0.0 | 0.0 |
|  | xylene | 0.9 | 3.6 | 6.5 | 9.3 | 9.9 |
|  | trimethyl-benzene | 0.6 | 0.1 | 0.1 | 0.1 | 0.1 |
|  | naphthalene | 9.1 | 43.5 | 66.1 | 106.1 | 103.6 |
|  | Total | 74.8 | 329.4 | 525.5 | 784.9 | 799.5 |

A large increase in the selectivity to total hydrocarbons resulted after catalyst activation and an increase in reactor temperature and increase in space velocity as shown in Tables 1-3. The temperature was 900-1030° C. for the primary reaction zone. The temperature of the secondary reaction zone was held at 950° C. Ethylene, acetylene, benzene, and naphthalene were the major products, and the highest yields were obtained at higher temperatures and higher space velocities.

Example 3

Non-oxidative coupling of methane reactions were investigated for fine catalyst particles as described in Example 2, but with thicker catalyst beds of about 1.5-2 cm. Eight different catalyst samples in their fine powder forms (>400 mesh) were tested with thicker catalyst bed length (1.5-2 cm), and the data are displayed in Table 4.

TABLE 4

| Catalyst Sample # | Bed length (cm) | Max conversion | Total HC Selectivity | ethylene | acetylene | benzene | naphthalene |
|---|---|---|---|---|---|---|---|
| 1 | 2 | 11.0 | 32.2 | 15.7 | 6.2 | 4.3 | 0.5 |
| 2 | 1.5 | 7.7 | 33.4 | 19.1 | 5.5 | 2.2 | 0.0 |
| 3 | 1.5 | 10.7 | 24.8 | 14.4 | 4.0 | 2.1 | 0.0 |
| 4 | 1.5 | 7.6 | 26.4 | 17.1 | 3.2 | 1.4 | 0.0 |
| 5 | 1.5 | 6.2 | 33.1 | 18.1 | 5.4 | 2.0 | 0.0 |
| 6 | 1.5 | 7.0 | 26.2 | 16.4 | 3.8 | 1.0 | 0.0 |
| 7 | 1.5 | 12.4 | 12.4 | 7.8 | 2.3 | 0.4 | 0.0 |
| 8 | 1.5 | 4.0 | 29.8 | 19.2 | 0.5 | 1.4 | 0.0 |

All samples in Table 4 displayed substantially lower hydrocarbon selectivity and more losses to heavier hydrocarbons and coke as compared to Example 2, which investigated a thinner catalyst bed length. This clearly demonstrates that catalyst bed length is an important factor in the process design. Catalyst bed length affects the radical propagation process. In the case of a thinner catalyst bed, methyl radicals released into the gas phase recombined to ethane, and the ethane was converted into ethylene and other higher hydrocarbons, such as benzene and other aromatics. In the case of a thicker catalyst bed, the secondary products generated had a higher chance to re-adsorb to a catalyst surface, undergo additional surface reactions, leading to formation of undesired surface coke. The fine catalyst particles in a thicker catalyst bed configuration showed lower yields and more losses to heavies and coke. Therefore, a thin pancake-like catalyst bed could be a preferred design in one aspect.

gas was varied from 4840 mL/g/h to 42800 mL/g/h. The effluent composition (product mixture) was monitored by an online Gas Chromatography (GC) (Agilent 7890B), equipped with an FID with CP-SilicaPlot capillary column; and a TCD with ShinCarbon ST packed column. The primary and secondary reaction zones were held constant at different temperatures (i.e., 1030° C. and 960° C., respectively), as outlined in Table 5.

TABLE 5

| | | | | | | | | | |
|---|---|---|---|---|---|---|---|---|---|
| Primary Temperature T1 setting (° C.) | | 1030 | 1030 | 1030 | 1030 | 1030 | 1030 | 1030 | 1030 |
| Secondary Temperature T2 setting (° C.) | | 960 | 960 | 960 | 960 | 960 | 960 | 960 | 960 |
| SV (mL/g/h) | | 4840 | 10000 | 11250 | 12500 | 14000 | 16377 | 21400 | 42800 |
| Conversion | | 28.4% | 17.4% | 17.0% | 17.2% | 15.3% | 12.6% | 7.5% | 2.4% |
| TOF (mol/h/m$^2$) | | 0.6 | 0.7 | 0.8 | 0.9 | 0.9 | 0.8 | 0.7 | 0.4 |
| Selectivity (carbon basis) | ethane | 1.4% | 1.7% | 1.6% | 1.6% | 1.6% | 1.7% | 2.4% | 6.5% |
| | ethylene | 10.5% | 21.0% | 21.0% | 20.7% | 22.1% | 24.3% | 25.8% | 29.4% |
| | acetylene | 0.8% | 2.1% | 2.3% | 2.7% | 3.3% | 4.5% | 7.3% | 9.4% |
| | propane | 0.0% | 0.0% | 0.0% | 0.0% | 0.0% | 0.0% | 0.0% | 0.0% |
| | propylene | 0.4% | 1.5% | 1.5% | 1.5% | 1.7% | 2.3% | 3.8% | 6.4% |
| | i-butane | 0.0% | 0.1% | 0.1% | 0.2% | 0.2% | 0.3% | 0.8% | 3.2% |
| | n-butane | 0.0% | 0.0% | 0.0% | 0.0% | 0.0% | 0.0% | 0.0% | 0.0% |
| | 1-butene | 0.0% | 0.2% | 0.2% | 0.3% | 0.4% | 0.7% | 2.1% | 8.2% |
| | (trans-2, i)-Butene | 0.1% | 0.4% | 0.4% | 0.4% | 0.5% | 0.6% | 1.1% | 2.9% |
| | cis-Butene | 0.0% | 0.0% | 0.0% | 0.0% | 0.0% | 0.0% | 0.0% | 0.0% |
| | pentane | 0.0% | 0.1% | 0.1% | 0.1% | 0.1% | 0.1% | 0.3% | 1.0% |
| | benzene | 18.1% | 28.8% | 28.2% | 27.3% | 28.5% | 29.7% | 26.9% | 12.8% |
| | toluene | 0.7% | 2.3% | 2.3% | 2.2% | 2.6% | 3.4% | 5.3% | 3.7% |
| | ethyl-benzene | 0.3% | 0.0% | 0.0% | 0.0% | 0.0% | 0.0% | 0.0% | 1.2% |
| | xylene | 0.0% | 0.8% | 0.8% | 0.8% | 0.9% | 1.1% | 1.6% | 0.2% |
| | trimethyl-benzene | 0.2% | 1.0% | 1.1% | 1.8% | 1.5% | 1.9% | 1.7% | 1.0% |
| | naphthalene | 1.3% | 19.0% | 16.3% | 14.9% | 15.7% | 16.8% | 14.5% | 1.0% |
| | Total | 33.9% | 78.9% | 76.2% | 74.3% | 79.2% | 87.5% | 93.7% | 86.6% |
| STY (mol-product/kg-cat/h) | ethylene | 2.7 | 6.7 | 7.4 | 8.2 | 8.7 | 9.2 | 7.6 | 5.6 |
| | benzene | 1.5 | 3.1 | 3.3 | 3.6 | 3.7 | 3.8 | 2.6 | 0.8 |
| | naphthalene | 0.1 | 1.2 | 1.1 | 1.2 | 1.2 | 1.3 | 0.9 | 0.0 |
| | Total | 5.0 | 13.0 | 14.1 | 15.7 | 16.8 | 18.2 | 16.0 | 12.0 |

Example 4

The methane conversion, as well as selectivity, yield, and STY to the major products were investigated as a function of the space velocity for non-oxidative coupling of methane reactions. Non-oxidative coupling of methane reactions were investigated in a continuous flow, fixed bed reactor (7.0 mm ID×9.6 mm OD×24" tube) with 0.117 mL (0.1 g) of fine catalyst particles (e.g., fused $Fe_2SiO_4/SiO_2$ fine powder) with an average size of 400-635 mesh, which catalyst particles were packed in the primary reaction zone of the reactor on a bed of quartz wool/felt, unless otherwise stated. The reactor was heated to 950° C. under Ar and then the feed gas was turned on at an appropriate flowrate. The catalyst was activated under these conditions for two hours before introducing the reactant mixture to the reactor. A feed gas (reactant mixture) contained 90 vol. % $CH_4$ and 10 vol. % $N_2$, wherein the $N_2$ in the feed gas was used as internal standard. As shown in Table 5, the space velocity of the feed As it can be seen from Table 5, the conversion, selectivity, yield, and STY to the major products were controlled by the space velocity in the reactor. With increasing space velocity from 4840 mL/g/h to 42800 mL/g/h, methane conversion dropped from 28.4% to 2.4%, while total hydrocarbon selectivity increased from 34% to ~90%. Selectivities to $C_2$-$C_5$ hydrocarbons increased with increasing the space velocity. Selectivities to aromatics increased with increasing the space velocity to 16377-21400 mL/g/h, and then selectivities to aromatics decreased with increasing the space velocity. The data in Table 5 support a sequential pathway where $CH_4 \rightarrow \{C_2\text{-}C_5\} \rightarrow \{aromatics\} \rightarrow$ polyaromatic hydrocarbons (PAHs)+$H_2$ for the formation of hydrogen, $C_2$-$C_5$ hydrocarbons, and aromatics, and agree with the modeling results. The data in Table 5 show that the highest selectivity to total hydrocarbons and the highest STY for total hydrocarbons were at different SV.

Example 5

The methane conversion, as well as selectivity, yield, and STY to the major products were investigated as a function of the temperature of the primary reaction zone for non-oxidative coupling of methane reactions. Non-oxidative coupling of methane reactions were investigated in a continuous flow, fixed bed reactor (7.0 mm ID×9.6 mm OD×24" tube) with 0.117 mL (0.1 g) of fine catalyst particles (e.g., fused $Fe_2SiO_4/SiO_2$ fine powder) with an average size of 400-635 mesh, which catalyst particles were packed in the primary reaction zone of the reactor on a bed of quartz wool/felt, unless otherwise stated. The reactor was heated to 950° C. under Ar and then the feed gas was turned on at the appropriate flowrate. The catalyst was activated under these conditions for two hours before introducing the reactant mixture to the reactor. A feed gas (reactant mixture) contained 90 vol. % $CH_4$ and 10 vol. % $N_2$, wherein the $N_2$ in the feed gas was used as internal standard. The secondary reaction zone temperature was held constant at 960° C., while the primary reaction zone temperature was increased, as outlined in Table 6.

primary reaction zone of the reactor on a bed of quartz wool/felt, unless otherwise stated. The reactor was heated to 950° C. under Ar and then the feed gas was turned on at the appropriate flowrate. The catalyst was activated under these conditions for two hours before introducing the reactant mixture to the reactor. A feed gas (reactant mixture) contained 90 vol. % $CH_4$ and 10 vol. % $N_2$, wherein the $N_2$ in the feed gas was used as internal standard. The primary reaction zone temperature and SV were held constant, while the secondary reaction zone temperature was varied, as outlined in Table 7.

TABLE 6

| | Primary Temperature T1 setting (° C.) | 960 | 1000 | 1010 | 1020 | 1030 | 1040 | 1050 |
|---|---|---|---|---|---|---|---|---|
| | Secondary Temperature T2 setting (° C.) | 960 | 960 | 960 | 960 | 960 | 960 | 960 |
| | SV (mL/g/h) | 12500 | 12500 | 12500 | 12500 | 12500 | 12500 | 12500 |
| | Conversion | 3.0% | 8.6% | 11.4% | 15.3% | 19.4% | 22.6% | 25.9% |
| | TOF (mol/h/m$^2$) | 0.2 | 0.4 | 0.6 | 0.8 | 1.0 | 1.2 | 1.3 |
| Selectivity (carbon basis) | ethane | 5.0% | 2.1% | 1.8% | 1.5% | 1.4% | 1.4% | 1.3% |
| | ethylene | 31.6% | 24.2% | 23.0% | 20.8% | 18.2% | 16.6% | 14.9% |
| | acetylene | 8.1% | 7.0% | 6.3% | 5.0% | 4.1% | 3.5% | 2.9% |
| | propane | 0.0% | 0.0% | 0.0% | 0.0% | 0.0% | 0.0% | 0.0% |
| | propylene | 7.0% | 3.1% | 2.3% | 1.6% | 1.1% | 0.8% | 0.6% |
| | i-butane | 2.2% | 0.6% | 0.4% | 0.2% | 0.1% | 0.1% | 0.1% |
| | n-butane | 0.0% | 0.0% | 0.0% | 0.0% | 0.0% | 0.0% | 0.0% |
| | 1-butene | 5.7% | 1.7% | 1.1% | 0.6% | 0.4% | 0.2% | 0.2% |
| | (trans-2, i)-Butene | 2.5% | 0.8% | 0.6% | 0.4% | 0.3% | 0.2% | 0.2% |
| | cis-Butene | 0.0% | 0.0% | 0.0% | 0.0% | 0.0% | 0.0% | 0.0% |
| | pentane | 0.6% | 0.2% | 0.2% | 0.1% | 0.1% | 0.1% | 0.0% |
| | benzene | 19.8% | 26.5% | 28.0% | 27.4% | 26.0% | 25.6% | 24.4% |
| | toluene | 5.5% | 4.6% | 3.7% | 2.6% | 1.9% | 1.5% | 1.2% |
| | ethyl-benzene | 0.0% | 0.0% | 0.0% | 0.0% | 0.0% | 0.0% | 0.0% |
| | xylene | 1.9% | 1.2% | 1.1% | 0.8% | 0.7% | 0.5% | 0.5% |
| | trimethyl-benzene | 0.0% | 1.4% | 1.3% | 1.6% | 1.5% | 1.1% | 1.1% |
| | naphthalene | 3.8% | 15.4% | 17.5% | 15.3% | 14.1% | 13.9% | 12.6% |
| | Total | 93.8% | 88.9% | 87.4% | 78.0% | 69.8% | 65.5% | 59.9% |
| STY (mol-product/kg-cat/h) | ethylene | 2.2 | 4.8 | 6.0 | 7.3 | 8.1 | 8.6 | 8.9 |
| | benzene | 0.5 | 1.7 | 2.4 | 3.2 | 3.9 | 4.4 | 4.8 |
| | naphthalene | 0.1 | 0.6 | 0.9 | 1.1 | 1.3 | 1.4 | 1.5 |
| | Total | 4.4 | 10.1 | 12.6 | 15.0 | 16.7 | 17.9 | 18.5 |

As it can be seen from Table 6, selectivity, yield, and STY to the major products were controlled by the primary reaction zone temperature in the reactor. Increasing the primary reaction zone temperature from 960° C. to 1050° C. resulted in increasing methane conversion from 3.0% to 25.9%, while decreasing hydrocarbon selectivity from 94% to 60%. Selectivities to $C_2$-$C_5$ hydrocarbons decreased with increasing the primary reaction zone temperature. Selectivities to benzene and naphthalene increased with increasing the temperature from 960° C. to 1010° C., and then decreased with further increasing the temperature. The data in Table 6 support a sequential pathway $CH_4 \rightarrow \{C_2$-$C_5\} \rightarrow \{aromatics\} \rightarrow PAHs+H_2$ for the formation of hydrogen, $C_2$-$C_5$ hydrocarbons, and aromatics. The data in Table 6 suggest that the temperature of the primary reaction zone impacts the sequential reaction pathway.

Example 6

The methane conversion, as well as selectivity, yield, and STY to the major products were investigated as a function of the temperature of the secondary reaction zone for non-oxidative coupling of methane reactions. The reactor was a continuous flow, fixed bed reactor (7.0 mm ID×9.6 mm OD×24" tube) with 0.117 mL (0.1 g) of fine catalyst particles (e.g., fused $Fe_2SiO_4$/$SiO_2$ fine powder) with an average size of 400-635 mesh, which catalyst particles were packed in the

TABLE 7

| | | | | |
|---|---|---|---|---|
| Primary Temperature T1 setting (° C.) | | 1030 | 1030 | 1030 |
| Secondary Temperature T2 setting (° C.) | | 1030 | 960 | 0 |
| SV (mL/g/h) | | 12500 | 12500 | 12500 |
| Conversion | | 21.7% | 12.4% | 6.8% |
| TOF (mol/h/m$^2$) | | 1.1 | 0.6 | 0.3 |
| Selectivity (carbon basis) | ethane | 1.5% | 1.9% | 3.0% |
| | ethylene | 18.9% | 24.8% | 32.6% |
| | acetylene | 0.1% | 0.6% | 4.3% |
| | propane | 0.0% | 0.0% | 0.0% |
| | propylene | 1.4% | 2.8% | 5.6% |
| | i-butane | 0.1% | 0.2% | 0.8% |
| | n-butane | 0.0% | 0.0% | 0.0% |
| | 1-butene | 0.4% | 0.2% | 0.4% |
| | (trans-2, i)-Butene | 0.5% | 0.8% | 1.6% |
| | cis-Butene | 0.1% | 0.1% | 0.2% |
| | pentane | 0.0% | 0.0% | 0.1% |
| | benzene | 23.3% | 26.8% | 28.0% |
| | toluene | 1.4% | 2.8% | 4.9% |
| | ethyl-benzene | 0.0% | 0.0% | 0.0% |
| | xylene | 0.6% | 1.0% | 1.7% |
| | trimethyl-benzene | 0.0% | 0.0% | 0.0% |
| | naphthalene | 8.1% | 9.6% | 8.3% |
| | Total | 56.2% | 71.6% | 91.6% |
| STY (mol-product/kg-cat/h) | ethylene | 9.4 | 7.1 | 5.1 |
| | benzene | 3.9 | 2.5 | 1.5 |
| | naphthalene | 0.8 | 0.5 | 0.3 |
| | Total | 15.9 | 11.9 | 9.1 |

As it can be seen from Table 7, selectivity, yield, and STY to the major products were controlled by the secondary reaction zone temperature in the reactor. Decreasing the secondary reaction zone temperature resulted in decreasing the methane conversion, and in increasing the total hydrocarbon selectivity, as well as increasing ethylene selectivity, owing to reducing the residence time in secondary reaction zone and quenching occurring sooner in the post-bed zone, i.e., secondary reaction/quench zone. The contribution of the wall effects within the secondary reaction zone was demonstrated by the data in Table 7, along with the importance of managing the temperature and residence time of the secondary zone.

Example 7

The methane conversion, as well as selectivity, yield, and STY to the major products were investigated as a function of the reactor type for non-oxidative coupling of methane reactions. In one experiment, the reactor was an empty 3/8" quartz tube (no catalyst), while in another experiment, the reactor was an empty acid washed 3/8" quartz tube (no catalyst). Nitric acid was used for washing the quartz tube. The reactor was heated to 950° C. under Ar and then the feed gas was turned on at the appropriate flowrate. The catalyst was activated under these conditions for two hours before introducing the reactant mixture to the reactor. A feed gas (reactant mixture) contained 90 vol. % $CH_4$ and 10 vol. % $N_2$, wherein the $N_2$ in the feed gas was used as internal standard. The primary reaction zone temperature was held constant at 1030° C., while the secondary reaction zone temperature was held constant at 960° C., as outlined in Table 8.

TABLE 8

| Primary Temperature T1 setting (° C.) | | 1030 | 1030 |
|---|---|---|---|
| Secondary Temperature T2 setting (° C.) | | 960 | 960 |
| Flow rate (mL/min) | | 85.3 | 85.3 |
| Run | | Empty 3/8" quartz tube | Empty acid washed 3/8" quartz tube |
| Conversion | | 14.1% | 16.1% |
| TOF (mol/h/m²) | | 2.9 | 3.4 |
| Selectivity (carbon basis) | ethane | 1.8% | 1.7% |
| | ethlene | 22.5% | 22.3% |
| | acetylene | 2.3% | 2.2% |
| | propane | 0.0% | 0.0% |
| | propylene | 2.0% | 2.1% |
| | i-butane | 0.2% | 0.2% |
| | n-butane | 0.0% | 0.0% |
| | 1-butene | 0.0% | 0.0% |
| | (trans-2, i)-Butene | 0.6% | 0.6% |
| | cis-Butene | 0.0% | 0.0% |
| | pentane | 0.6% | 0.5% |
| | benzene | 25.9% | 28.2% |
| | toluene | 2.3% | 2.1% |
| | ethyl-benzene | 0.1% | 0.3% |
| | xylene | 0.8% | 0.8% |
| | trimethyl-benzene | 1.3% | 1.2% |
| | naphthalene | 9.6% | 11.5% |
| | Total | 70.0% | 73.8% |
| STY (mol-product/kg-cat/h) | ethylene | 7.3 | 8.3 |
| | benzene | 2.8 | 3.5 |
| | naphthalene | 0.6 | 0.9 |
| | Total | 13.1 | 15.2 |

As it can be seen from Table 8, overall selectivity, yield, and STY to the major products were achieved when the quartz tube reactor wall was washed with nitric acid. The data in Table 8 indicate that quartz tube surface itself contributed significantly to the reaction. Acid washing the tube slightly increased conversions without loss of selectivity. Without wishing to be limited by theory, the acid washing removed surface impurities and/or particles from a surface of the tubes. Further, without wishing to be limited by theory, the acid washing could create vacancy sites or defect sites on the quartz tube surface after metal removal by high concentration nitric acid, which sites can act as new catalytically active sites.

Example 8

The methane conversion, as well as selectivity, yield, and STY to the major products were investigated as a function of hydrogen to methane volumetric feed ratio for non-oxidative coupling of methane reactions.

Selectivity and conversion results were acquired in the presence of a catalyst for four different $H_2$/feed volumetric ratios (0, 1:10, 1:1, and 2:1). Selectivity and conversion results were also acquired in the presence of a catalyst for three different $N_2$/feed volumetric ratios (0, 1:1, and 2:1). The catalyst was 0.1 g of $Fe_2SiO_4/SiO_2$ powder (>400 mesh size). The reactor was 7.0 mm ID×9.6 mm OD×24" quartz tube. A feed gas (reactant mixture) contained 90 vol. % $CH_4$ and 10 vol. % $N_2$, wherein the $N_2$ in the feed gas was used as internal standard. The effluent composition (product mixture) was monitored by an online Gas Chromatography (GC) (Agilent 7890B), equipped with an FID with CP-SilicaPlot capillary column; and a TCD with ShinCarbon ST packed column.

The primary and secondary reaction zones were held constant at different temperatures (i.e., 1030° C. and 960° C., respectively), as outlined in Tables 9 and 10. Table 9 displays data for hydrogen introduced to the reactor along with the methane, while Table 10 displays data for control experiments where nitrogen was introduced to the reactor along with the methane.

TABLE 9

| Primary Temperature T1 setting (° C.) | | 1030 | 1030 | 1030 | 1030 |
|---|---|---|---|---|---|
| Secondary Temperature T2 setting (° C.) | | 960 | 960 | 960 | 960 |
| SV (mL/g/h) | | 12500 | 12500 | 12500 | 12500 |
| H2/Feed ratio | | 0 | 1:10 | 1:1 | 2:1 |
| Conversion | | 19.5% | 16.4% | 5.3% | 3.1% |
| TOF (mol/h/m²) | | 1.0 | 0.8 | 0.3 | 0.2 |
| Selectivity (carbon basis) | ethane | 1.6% | 1.8% | 5.9% | 10.3% |
| | ethylene | 19.2% | 22.3% | 36.9% | 48.4% |
| | acetylene | 0.4% | 0.7% | 0.2% | 0.2% |
| | propane | 0.0% | 0.0% | 0.0% | 0.0% |
| | propylene | 1.5% | 1.7% | 1.1% | 1.0% |
| | i-butane | 0.1% | 0.1% | 0.0% | 0.0% |
| | n-butane | 0.0% | 0.0% | 0.0% | 0.0% |
| | 1-butene | 0.1% | 0.2% | 0.3% | 0.0% |
| | (trans-2, i)-Butene | 0.4% | 0.5% | 0.4% | 0.0% |
| | cis-Butene | 0.1% | 0.1% | 0.0% | 0.0% |
| | pentane | 0.0% | 0.0% | 0.0% | 0.0% |
| | benzene | 23.1% | 21.1% | 1.5% | 0.1% |
| | toluene | 1.5% | 1.5% | 0.0% | 0.0% |
| | ethyl-benzene | 0.0% | 0.0% | 0.0% | 0.0% |
| | xylene | 0.6% | 0.5% | 0.0% | 0.0% |
| | trimethyl-benzene | 0.0% | 0.0% | 0.0% | 0.0% |
| | naphthalene | 8.2% | 6.9% | 0.0% | 0.0% |
| | Total | 56.8% | 57.3% | 46.2% | 60.0% |
| STY (mol-product/ kg-cat/h) | ethylene | 8.6 | 8.4 | 4.5 | 3.5 |
| | benzene | 3.5 | 2.7 | 0.1 | 0.0 |
| | naphthalene | 0.7 | 0.5 | 0.0 | 0.0 |
| | Total | 14.6 | 13.3 | 5.4 | 4.3 |

TABLE 10

| In this example the conversion, selectivity, yield, and Secondary Temperature T2 setting (° C.) | | 1030 960 | 1030 960 | 1030 960 |
|---|---|---|---|---|
| SV (mL/g/h) | | 12500 | 12500 | 12500 |
| N2/Feed ratio | | 0 | 1:1 | 2:1 |
| Conversion | | 19.5% | 17.1% | 16.9% |
| TOF (mol/h/m²) | | 1.0 | 0.9 | 0.9 |
| Selectivity (carbon basis) | ethane | 1.6% | 1.1% | 1.0% |
| | ethylene | 19.2% | 20.1% | 17.7% |
| | acetylene | 0.4% | 1.1% | 3.9% |
| | propane | 0.0% | 0.0% | 0.0% |
| | propylene | 1.5% | 1.8% | 1.6% |
| | i-butane | 0.1% | 0.2% | 0.3% |
| | n-butane | 0.0% | 0.0% | 0.0% |
| | 1-butene | 0.1% | 0.2% | 0.1% |
| | (trans-2, i)-Butene | 0.4% | 0.6% | 0.6% |
| | cis-Butene | 0.1% | 0.1% | 0.0% |
| | pentane | 0.0% | 0.0% | 0.0% |
| | benzene | 23.1% | 23.9% | 21.6% |
| | toluene | 1.5% | 1.7% | 1.7% |
| | ethyl-benzene | 0.0% | 0.0% | 0.0% |
| | xylene | 0.6% | 0.7% | 0.7% |
| | trimethyl-benzene | 0.0% | 0.0% | 0.0% |
| | naphthalene | 8.2% | 8.7% | 7.5% |
| | Total | 56.8% | 60.3% | 56.6% |
| STY (mol-product/kg-cat/h) | ethylene | 8.6 | 7.9 | 6.9 |
| | benzene | 3.5 | 3.1 | 2.8 |
| | naphthalene | 0.7 | 0.7 | 0.6 |
| | Total | 14.6 | 13.5 | 13.0 |

As will be appreciated by one of skill in the art, and with the help of this disclosure, the addition of either a product or additional reactant will shift the reaction equilibrium, changing the extent of reaction, the conversion, and the final product mix. Without wishing to be limited by theory, the addition of hydrogen, a product of the non-oxidative coupling of methane reaction, can control the reaction equilibria in both the gas phase and on the catalytic surface.

As it can be seen from Tables 9 and 10, the conversion, selectivity, yield, and STY to the major products were controlled by the hydrogen/methane ratio in the reactor. As will be appreciated by one of skill in the art, and with the help of this disclosure, co-feeding hydrogen can suppress coke formation in certain reactions. As it can be seen from Table 9, hydrogen was co-fed at 1:10, 1:1 and 2:1 $H_2$/feed volumetric ratios, while maintaining the total gas hourly space velocity at 12500 mL/g/h. The data in Table 9 indicate that methane conversion significantly decreased with increasing $H_2$/feed volumetric ratio. While keeping the same weight hourly space velocity and temperature, methane conversion decreased significantly from 19.5% to 16.4%, 5.3% and 3.1% with increasing hydrogen/feed ratios from 0 to 1:10, 1:1, and 2:1, respectively. Without wishing to be limited by theory, this decrease in conversion with increasing the amount of hydrogen introduced to the reactor corresponds to a negative reaction order for hydrogen on the catalytic surface, which can inhibit the rate of methyl radical generation. Furthermore, the final product distribution was largely changed by $H_2$/feed ratio although the overall hydrocarbon selectivity was affected only to a small extent. When increasing hydrogen/feed ratio from 0 to 2:1, ethane and ethylene selectivities increased from 1.6% to 10.3%, and from 19.2% to 48.4%, respectively; and benzene and naphthalene selectivities decreased from 23.1% to 0.1% and from 8.2% to 0.0%, respectively. These results indicate a hydrogenation/hydrocracking mechanism in the gas phase, which can lead to changes in the final product distribution, wherein the final product distribution can display a higher content of lighter hydrocarbons and less aromatics.

Further, the data in Table 10 indicate that the decrease in methane conversion with increasing the hydrogen content in the reactor was not a result of hydrogen dilution, as nitrogen dilution did not lead to a significant decrease in methane conversion or product selectivities. Without wishing to be limited by theory, the decrease in methane conversion with increasing the amount of hydrogen introduced to the reactor could be due to competitive adsorption of hydrogen on catalytically active sites for methyl radical generation and/or hydrogenation of methyl radicals back to methane. Further, without wishing to be limited by theory, hydrogen can control the non-oxidative coupling of methane reaction equilibria in both the gas phase and on the catalytic surface.

As it can be seen from Tables 9 and 10, co-feeding hydrogen did not improve total hydrocarbon selectivity; however, co-feeding hydrogen drastically changed the product distribution. With higher $H_2$/feed volumetric ratios, lighter hydrocarbons had increased selectivity while aromatics had decreased selectivity, suggesting a hydrogenation or hydrocracking pathway of heavier hydrocarbons to lighter ones.

Example 9

The methane conversion, as well as selectivity, yield, and STY to the major products were investigated as a function of the upstream pressure in the reactor for non-oxidative coupling of methane reactions. The reactor was a continuous flow, fixed bed reactor (7.0 mm ID×9.6 mm OD×24" tube) with 0.117 mL (0.1 g) of fine catalyst particles (e.g., fused $Fe_2SiO_4/SiO_2$ fine powder) with an average size of 400-635 mesh, which catalyst particles were packed in the primary reaction zone of the reactor on a bed of quartz wool/felt, unless otherwise stated. The reactor was heated to 950° C. under Ar and then the feed gas was turned on at the appropriate flowrate. The catalyst was activated under these conditions for two hours before introducing the reactant mixture to the reactor. A feed gas (reactant mixture) contained 90 vol. % $CH_4$ and 10 vol. % $N_2$, wherein the $N_2$ in the feed gas was used as internal standard. The primary and secondary reaction zones were held constant at different temperatures (i.e., 1030° C. and 960° C., respectively), as outlined in Table 11.

TABLE 11

| Primary Temperature T1 setting (° C.) | | 1030 | 1030 | 1030 |
|---|---|---|---|---|
| Secondary Temperature T2 setting (° C.) | | 960 | 960 | 960 |
| SV (mL/g/h) | | 12500 | 12500 | 12500 |
| Upstream gauge pressure (psig) | | 2.0 | 5.0 | 9 |
| Conversion | | 22.1% | 25.1% | 28.6% |
| Selectivity (carbon basis) | ethane | 1.9% | 2.1% | 2.5% |
| | ethylene | 17.9% | 15.0% | 11.0% |
| | acetylene | 1.3% | 0.8% | 0.2% |
| | propane | 0.0% | 0.0% | 0.0% |
| | i-butane | 0.1% | 0.0% | 0.0% |
| | n-butane | 0.0% | 0.0% | 0.0% |
| | 1-butene | 0.1% | 0.1% | 0.0% |
| | (trans-2, i)-Butene | 0.3% | 0.2% | 0.1% |
| | cis-Butene | 0.0% | 0.0% | 0.0% |
| | pentane | 0.1% | 0.1% | 0.1% |
| | benzene | 28.0% | 26.0% | 24.0% |
| | toluene | 1.7% | 1.3% | 1.0% |
| | ethyl-benzene | 0.0% | 0.0% | 0.0% |
| | xylene | 0.6% | 0.5% | 0.3% |
| | trimethyl-benzene | 0.6% | 0.4% | 0.3% |
| | naphthalene | 25.3% | 24.2% | 16.7% |
| | Total | 78.8% | 71.5% | 56.5% |
| STY (mol-product/kg-cat/h) | ethylene | 9.1 | 8.7 | 7.2 |
| | benzene | 4.8 | 5.0 | 5.2 |
| | naphthalene | 2.6 | 2.8 | 2.2 |

As it can be seen from Table 11, selectivity, yield, and STY to the major products were controlled by pressure. With increasing the pressure, volumetric flow rate decreased, leading to increasing contact time in catalyst bed, further leading to increased conversion and decreased selectivity.

Example 10

Non-oxidative coupling of methane reactions were carried out in a continuous flow, fixed bed quartz tube reactor. In all reaction tests, 0.75 g of quartz chips catalyst was packed in the reactor, unless otherwise stated. A feed gas (reactant mixture) contained 90 vol. % $CH_4$ and 10 vol. % $N_2$ wherein the $N_2$ in the feed gas was used as internal standard. The effluent composition (product mixture) was monitored by an online Gas Chromatography (GC) (Agilent 7890B), equipped with an FID detector with CP-SilicaPlot capillary column; and a TCD detector with ShinCarbon ST packed column.

Three different catalyst (e.g., catalyst bed) placement positions were investigated: bed position #1, at 13 inches from a reactant mixture inlet position; bed position #2, at 12 inches from a reactant mixture inlet position; and bed position #3, at 9 inches from a reactant mixture inlet position. The space velocity, temperature, and residence time in each zone (e.g., contact time) were varied. Selectivities and conversions were calculated as outlined in equations (1)-(7), and the data are displayed in FIGS. 11 through 14 and Table 12.

the upstream end of the reactor, the total hydrocarbon selectivity increases. Without wishing to be limited by theory, it is possible that more heavies are formed as the secondary products formed from the wall effects react with the catalyst bed near the outlet end. These secondary products can react with the catalyst in the catalyst bed and forms higher polyaromatic hydrocarbons (PAHs), which are lost as "coke".

The trend of increased selectivity diminished as the temperature was increased and as the space velocity decreased. The higher total hydrocarbon selectivity at higher conversions is counter intuitive as one normally would expect lower selectivity as one increases conversion. Without wishing to be limited by theory, the results in FIGS. 11 through 14 and Table 12 indicate the complex interplay between the mass and heat transport, that when the temperature is high and the flow rate is low, the surface reaction dominates; and when the temperature is low and the flow rate is high, the gas phase chemistry dominates. Therefore, by varying the space velocity, temperature, pressure, extent of mixing and residence time, the conversion and selectivity to individual product mixture components can be controlled, and such control would be dependent on the activity of the catalyst as well as the reactor design. The data in Table 12 further indicate that it could be advantageous to use an

TABLE 12

| Bed position | Temperature (° C.) | SV (mL/g/h) | Conversion (%) | Hydrocarbon Selectivity (%) | Ethane Selectivity (%) | Ethylene Selectivity (%) | Acetylene Selectivity (%) | Benzene Selectivity (%) | Naphthalene Selectivity (%) |
|---|---|---|---|---|---|---|---|---|---|
| 1 | 950 | 4840 | 5.8 | 7.0 | 3.6 | 3.0 | 0.0 | 0.0 | 0.0 |
| 2 | 950 | 4840 | 5.0 | 9.5 | 5.5 | 3.4 | 0.1 | 0.2 | 0.0 |
| 3 | 950 | 4840 | 3.6 | 20.2 | 4.5 | 11.3 | 1.3 | 0.3 | 0.1 |
| 2 | 1030 | 2420 | 18.9 | 39.7 | 1 | 16.3 | 5.9 | 8.3 | 2.1 |
| 3 | 1030 | 2420 | 14.5 | 46.3 | 1.6 | 16.3 | 7.3 | 10 | 2.8 |
| 2 | 1030 | 1210 | 27.1 | 35.5 | 0.7 | 14.3 | 2.9 | 10.6 | 3.2 |
| 3 | 1030 | 1210 | 17.9 | 43.9 | 1.0 | 16.0 | 5.5 | 10.9 | 4.6 |

The data in FIGS. 11 through 14 and Table 12 indicate the complex interplay between the catalyzed surface reactions, the homogeneous gas phase reactions, and the mass and heat transport connecting the two zones. The catalytic bed (quartz chips) and the reactor walls provide the same amount of active sites in all three configurations, but as the catalyst bed is moved from the downstream end of the reactor towards integrated catalyst-reactor design having a primary reaction zone for the catalytic chemistry, a secondary zone for the homogeneous uncatalyzed thermal cracking chemistry to occur, and/or quench zone to stop the chemistry and utilize the heat value of the reactor effluent.

The STY was also calculated, and the data are displayed in Table 13.

TABLE 13

| Catalyst | Bed position | Temp. (° C.) | SV (mL/g/h) | Ethane STY (g/kg/h) | Ethylene STY (g/kg/h) | Acetylene STY (g/kg/h) | Benzene STY (g/kg/h) | Naphthalene STY (g/kg/h) |
|---|---|---|---|---|---|---|---|---|
| Quartz chips | 1 | 950 | 4840 | 6 | 5 | 0 | 0 | 0 |
| Quartz chips | 2 | 950 | 4840 | 8 | 5 | 0 | 0 | 0 |
| Quartz chips | 3 | 950 | 4840 | 5 | 12 | 1 | 0 | 0 |
| Quartz chips | 2 | 1030 | 2420 | 3 | 45 | 16 | 23 | 6 |
| Quartz chips | 3 | 1030 | 2420 | 3 | 46 | 19 | 35 | 10 |
| Quartz chips | 2 | 1030 | 1210 | 1 | 28 | 6 | 21 | 6 |
| Quartz chips | 3 | 1030 | 1210 | 1 | 21 | 7 | 14 | 6 |

The data in Table 13 indicate that by varying the space velocity, temperature, and residence time, the yield of each individual product mixture component can be controlled.

Example 11

Figure 15:
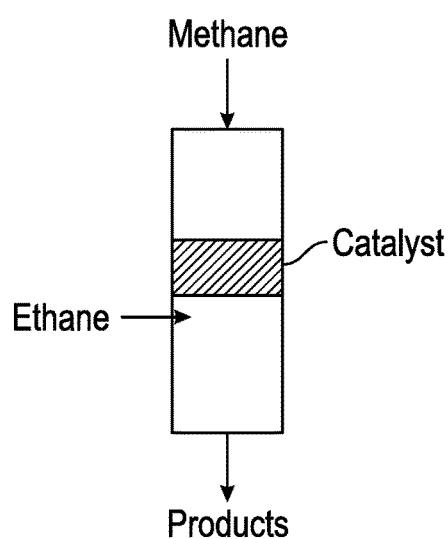
FIG. 15 displays a reactor configuration for conducting non-oxidative coupling of methane reactions, wherein ethane is introduced to the reactor in the secondary reaction zone.

Non-oxidative coupling of methane reactions were carried out in a continuous flow, fixed bed reactor, as displayed in FIG. 15. The fixed bed contained quarts chips catalyst. The reaction was carried out at 1050° C. Ethane was added to the reactor after the catalyst zone for quenching of reaction products, wherein ethane participated in an endothermic reaction of cracking to ethylene ($C_2H_6 \rightarrow C_2H_4+H_2$), while consuming part of the heat produced exothermically via the non-oxidative coupling of methane reaction. The reactor had two zones, comprising a catalyst zone and a post catalyst zone (with no catalyst). The post catalyst zone had a simple additional inlet where the ethane was fed to the reactor. The ethane was mixed with hot gases present in the post catalyst zone and was cracked under the heat of the hot gases. Ethane feed could be regulated by a separate mass flow controller (MFC) which can allow for regulating $CH_4/C_2H_6$ ratios.

Conversion of methane in the catalytic reaction zone was 17%, while ethane conversion was 90%. While hydrocarbon products such as ethylene, ethane, benzene, naphthalene were produced from methane and ethane, hydrocarbon selectivity was not calculated. Selectivity of coke formation in relation to converted methane and ethane was 50%. As will be appreciated by one of skill in the art, and with the help of this disclosure, when low amounts of acetylene are produced (as is expected in the case of this example), quenching of the gas mixture by ethane does not need addition of water (e.g., steam). Further, as will be appreciated by one of skill in the art, and with the help of this disclosure, acetylene is a very reactive species which can lead to the formation of coke fragments. Further, as will be appreciated by one of skill in the art, and with the help of this disclosure, water can be added to the quench zone if an acetylene concentration is more than about 3 mol %; for example, at acetylene concentrations of about 15 mol %, addition of water is needed to get more ethylene in the products. Therefore, depending on the desired product distribution (e.g., whether the target product distribution is more ethylene or more benzene), one can regulate an amount of water added to the quenching zone. For example, if it is desired to produce more benzene, addition of water is not necessary. Generally, dilution of water reduces a partial pressure of acetylene and its oligomerization to ethylene.

Example 12

Figure 16A:
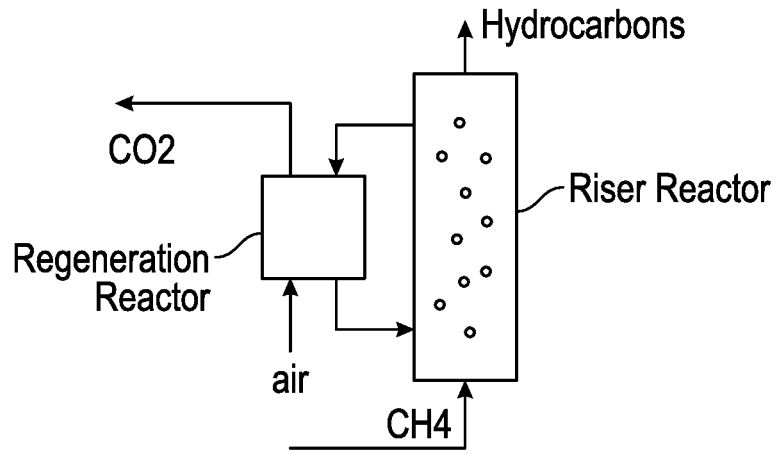
FIGS. 16A-C display a reactor configurations for conducting non-oxidative coupling of methane reactions in a riser reactor, wherein a $C_{2+}$ alkane can be also introduced to the reactor with the feed.
Figure 16B:
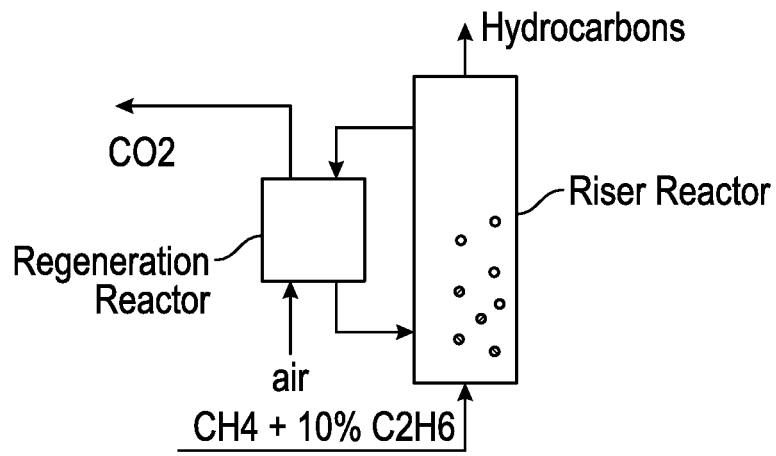
Figure 16C:
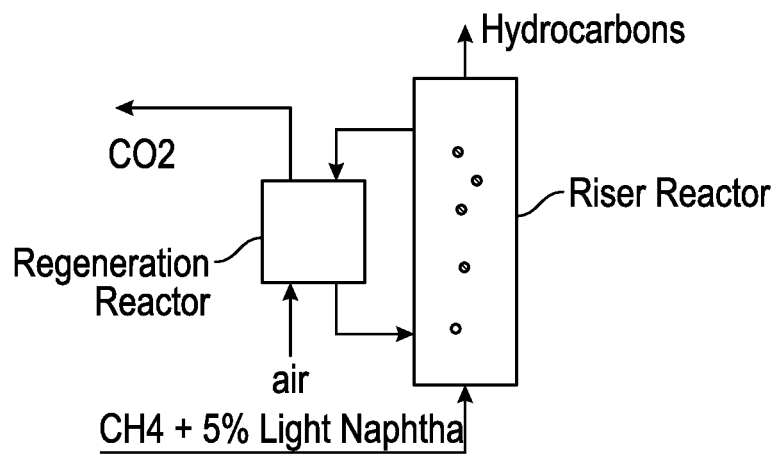

Non-oxidative coupling of methane reactions were carried out in a riser reactor, under thermo-catalytic conditions, as displayed in FIGS. 16A-C. The catalyst was quartz sand with a linear velocity of gas-solid mixture of 4 m/sec. The space velocity was about 7200 $h^{-1}$. The quartz sand used as contact material after the reaction zone was allowed to fall down into a regeneration reactor where the coke accumulated on sand was burned out with formation of $CO_2$. The quartz sand carried the heat accumulated from regeneration zone to the reaction zone for the conversion of methane to a mixture of hydrocarbons. The methane conversion in a riser reactor can transport a portion of the heat generated in the regeneration reactor with the quartz sand, wherein the heat in the regeneration reactor can be produced from combustion of the coke accumulated on its surface during reactions in the riser reactor.

The temperature in the reaction and regeneration zone was about 1000° C. The gas mixture recovered from the reaction zone comprised $CH_4$, CAL, $C_2H_6$, $C_2H_2$, $C_6H_6$, $C_{10}H_8$ and $C_{10}H_6$. The gas mixture formed in regeneration zone comprised $N_2$ and $CO_2$.

For the reactor configuration illustrated in FIG. 16A, the conversion of methane in reaction zone was 15%.

For the reactor configuration illustrated in FIG. 16B, a 10 vol. % ethane was co-fed with the methane to the riser reactor. The conversion of methane in reaction zone was 22%, while the conversion of ethane was 95%.

For the reactor configuration illustrated in FIG. 16C, a 5 vol. % light naphtha was co-fed with the methane to the riser reactor. The conversion of methane in reaction zone was 25%, while the conversion of light naphtha was 100%. As will be appreciated by one of skill in the art, and with the help of this disclosure, riser reactors with quartz sand are generally used in pyrolysis of hydrocarbons such as light gases and heavy crude cracking where the target is cracking of high molecular hydrocarbons to olefins. However, the transport feature of quartz sand in the reactor can change the product distribution in the product mixture. For example, at linear velocities of less than about 4 m/sec (e.g., slow transportation rate), for example 3 m/sec, coke formation can increase (when compared with higher linear velocities). As another example, increasing the linear velocity from about 4 m/sec to about 5-6 m/sec can increase hydrocarbon selectivity and reduce coke production. Further, riser reactors can control olefin/aromatics ratio as well.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed herein are provided solely for their disclosure prior to the filing date of the present application. Nothing herein is to be construed as an admission that the inventors are not entitled to antedate such disclosure by virtue of prior invention.

In any application before the United States Patent and Trademark Office, the Abstract of this application is provided for the purpose of satisfying the requirements of 37 C.F.R. § 1.72 and the purpose stated in 37 C.F.R. § 1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

The present disclosure is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, can be suggest to one of ordinary skill in the art without departing from the spirit of the present invention or the scope of the appended claims.

ADDITIONAL DISCLOSURE

A first aspect, which is a method for producing $C_{2+}$ hydrocarbons and hydrogen comprising (a) introducing a reactant mixture to a reactor, wherein the reactant mixture comprises methane ($CH_4$), and wherein the reactor comprises a preheat zone, a primary reaction zone, a secondary reaction zone, and a quench zone; (b) heating the reactant mixture to a preheating temperature in the preheat zone to yield a heated reactant mixture; (c) generating free radicals in at least a portion of the heated reactant mixture in the primary reaction zone to form a primary effluent mixture comprising free radicals, $C_{2+}$ hydrocarbons, hydrogen and unreacted methane; (d) reacting at least a portion of the primary effluent mixture in the secondary reaction zone to form a secondary effluent mixture comprising $C_{2+}$ hydrocarbons, hydrogen, free radicals, and unreacted methane, wherein the secondary reaction zone is characterized by a secondary reaction zone temperature, wherein the secondary reaction zone temperature is greater than the preheating temperature, wherein an amount of unreacted methane in the primary effluent mixture is greater than an amount of unreacted methane in the secondary effluent mixture, and wherein an amount of free radicals in the primary effluent mixture is greater than an amount of free radicals in the secondary effluent mixture; (e) cooling at least a portion of the secondary effluent mixture in the quench zone to a quench temperature to yield a product mixture comprising $C_{2+}$ hydrocarbons, hydrogen and unreacted methane, wherein the quench temperature is lower than the secondary reaction zone temperature; and (f) recovering at least a portion of the product mixture from the reactor.

A second aspect, which is the method of the first aspect, wherein the reactant mixture excludes oxygen.

A third aspect, which is the method of any one of the first and the second aspects, wherein the reactant mixture further comprises a diluent.

A fourth aspect, which is the method of the third aspect, wherein the diluent comprises nitrogen, inert gases, argon, neon, helium, krypton, xenon, carbon monoxide, carbon dioxide, hydrogen, steam, ethane, propane, butanes, unsaturated hydrocarbons, or combinations thereof.

A fifth aspect, which is the method of any one of the first through the fourth aspects, wherein the reactant mixture further comprises a promoter.

A sixth aspect, which is the method of the fifth aspect, wherein the promoter comprises alkanes, ethane, propane, alkenes, naphthalene, functionalized hydrocarbons, halogenated hydrocarbons, halogenated alkanes, chlorinated alkanes, methyl chloride, methylene chloride, carbon tetrachloride, chloroethane, brominated alkanes, methyl bromide, radical initiators, alcohols, ethers, or combinations thereof.

A seventh aspect, which is the method of any one of the first through the sixth aspects, wherein the reactor comprises a tubular reactor, a continuous flow reactor, a riser reactor, a reformer reactor, a fixed bed reactor, a shock tube reactor, a multi-tubular reactor, a membrane reactor, a dual flow reactor, a gauze reactor, a fluidized bed reactor, a moving bed reactor, a continuous stirred-tank reactor, a plug flow reactor, a microchannel reactor, a modular reactor, a modular microchannel reactor, a honeycombed monolithic reactor, a honeycombed wall filter monolithic reactor, or combinations thereof.

An eighth aspect, which is the method of any one of the first through the seventh aspects, wherein the preheating temperature is from about 200° C. to about 800° C.

A ninth aspect, which is the method of any one of the first through the eighth aspects, wherein the primary reaction zone is characterized by a primary reaction zone temperature of from about 700° C. to about 1,300° C.

A tenth aspect, which is the method of any one of the first through the ninth aspects, wherein the primary reaction zone temperature is equal to or greater than the secondary reaction zone temperature.

An eleventh aspect, which is the method of any one of the first through the tenth aspects, wherein the free radicals are generated by plasma sources.

A twelfth aspect, which is the method of the eleventh aspect, wherein the plasma sources comprise dielectric barrier discharge, cold plasma, corona discharge, glow discharge, gliding arc, spark discharge, microwave plasma, or combinations thereof.

A thirteenth aspect, which is the method of any one of the first through the twelfth aspects, wherein the free radicals are generated by a supersonic hot gas stream.

A fourteenth aspect, which is the method of any one of the first through the thirteenth aspects, wherein the free radicals are generated by photo-dissociation under irradiation with UV radiation.

A fifteenth aspect, which is the method of any one of the first through the fourteenth aspects, wherein the free radicals are generated catalytically, and wherein the primary reaction zone is a catalyzed reaction zone.

A sixteenth aspect, which is the method of the fifteenth aspect, wherein the catalyzed reaction zone is characterized by a catalyzed reaction zone residence time of from about 0.01 ms to about 3,500 ms.

A seventeenth aspect, which is the method of any one of the first through the sixteenth aspects, wherein the catalyzed reaction zone comprises a catalyst.

An eighteenth aspect, which is the method of the seventeenth aspect, wherein the catalyst comprises a catalytically active metal.

A nineteenth aspect, which is the method of the eighteenth aspect, wherein the catalytically active metal comprises Li, Na, K, Mg, Al, B, Ca, Sr, Ba, Y, La, Ti, Zr, Ce, V, Nb, Ta, Cr, Mo, W, Re, Fe, Ru, Co, Rh, Ir, Ni, Pd, Pt, Cu, Zn, Ge, In, Sn, Pb, Bi, Mn, Pr, Nd, Pm, Sm, Eu, Gd, Tb, Dy, Ho, Er, Tm, Yb, alloys thereof, intermetallic alloys thereof, oxides thereof, carbides thereof, nitrides thereof, silicides thereof, silicates thereof, germanides thereof, germanates thereof, titanates thereof, zirconates thereof, phosphides thereof, or combinations thereof.

A twentieth aspect, which is the method of any one of the first through the eighteenth aspects, wherein the catalyst further excludes silicon.

A twenty-first aspect, which is the method of the twentieth aspect, wherein the catalyst comprises a catalytically active metal comprising Li, Na, K, Mg, Al, B, Ca, Sr, Ba, Y, La, Ti, Zr, Ce, V, Nb, Ta, Cr, Mo, W, Re, Fe, Ru, Co, Rh, Ir, Ni, Pd, Pt, Cu, Zn, Ge, In, Sn, Pb, Bi, Mn, Pr, Nd, Pm, Sm, Eu, Gd, Tb, Dy, Ho, Er, Tm, Yb, alloys thereof, intermetallic alloys thereof, oxides thereof, carbides thereof, nitrides thereof, germanides thereof, germanates thereof, titanates thereof, zirconates thereof, phosphides thereof, or combinations thereof.

A twenty-second aspect, which is the method of any one of the first through the nineteenth aspects, wherein the catalytically active metals are doped in a lattice of amorphous-molten-state materials made from one or more of B, Al, Si, Ti, Zr, and Ge bonded with one or more of C, N and O.

A twenty-third aspect, which is the method of any one of the first through the seventeenth aspects, wherein the catalyst further excludes a catalytically active metal.

A twenty-fourth aspect, which is the method of the twenty-third aspect, wherein the catalyst comprises a silicon based material; Si bonded with one or more of C, N and O; silica; quartz, α-quartz, β-quartz; cristobalite; tridymite, α-tridymite, β-tridymite; silica glass; or combinations thereof.

A twenty-fifth aspect, which is the method of any one of the first through the twenty-fourth aspects, wherein the secondary reaction zone temperature is from about 700° C. to about 1,300° C.

A twenty-sixth aspect, which is the method of any one of the first through the twenty-fifth aspects, wherein the quench temperature is from about room temperature to about 700° C.

A twenty-seventh aspect, which is the method of any one of the first through the twenty-sixth aspects, wherein the quench zone is cooled by external heat exchange, external heat exchange to preheat the reactant mixture, removing supplied heat, removing heat, expansive cooling, converting thermal energy into work, dilution, endothermic reactions, addition of $C_{2+}$ alkanes, or combinations thereof.

A twenty-eighth aspect, which is the method of any one of the first through the twenty-seventh aspects, wherein the reactor is characterized by an inner diameter of from about 0.1 mm to about 5,000 mm, for example, a cylindrical or tubular reactor.

A twenty-ninth aspect, which is the method of any one of the first through the twenty-eighth aspects, wherein the reactor is characterized by a length of from about 10 mm to about 100 m, for example, a cylindrical or tubular reactor.

A thirtieth aspect, which is the method of any one of the first through the twenty-ninth aspects, wherein the reactor is characterized by a total pressure of from about 0.1 bar to about 40 bar.

A thirty-first aspect, which is the method of any one of the first through the thirtieth aspects, wherein the reactor is characterized by a gas hourly space velocity of from about 1,000 $h^{-1}$ to about 500,000 $h^{-1}$.

A thirty-second aspect, which is the method of any one of the first through the thirty-first aspects, wherein the reactor is characterized by a weight hourly space velocity of from about 1,000 $h^{-1}$ to about 500,000 $h^{-1}$.

A thirty-third aspect, which is the method of any one of the first through the thirty-second aspects, wherein the reactor is characterized by a laminar flow.

A thirty-fourth aspect, which is the method of any one of the first through the thirty-third aspects, wherein a methane conversion is from about 1% to about 85%.

A thirty-fifth aspect, which is the method of any one of the first through the thirty-fourth aspects, wherein a selectivity to $C_{2+}$ hydrocarbons is from about 5% to about 100%.

A thirty-sixth aspect, which is the method of any one of the first through the thirty-fifth aspects, wherein a selectivity to hydrogen is from about 40% to about 100%.

A thirty-seventh aspect, which is the method of any one of the first through the thirty-sixth aspects, wherein the $C_{2+}$ hydrocarbons comprise ethylene, ethane, acetylene, propylene, propane, benzene, substituted benzenes, naphthalene, or combinations thereof.

A thirty-eighth aspect, which is the method of the thirty-seventh aspect, wherein a selectivity to ethylene is from about 2% to about 85%.

A thirty-ninth aspect, which is the method of any one of the first through the thirty-eighth aspects, wherein a selectivity to benzene is from about 0% to about 60%.

A fortieth aspect, which is the method of any one of the first through the thirty-ninth aspects, wherein a selectivity to naphthalene is from about 0% to about 60%.

A forty-first aspect, which is the method of any one of the first through the fortieth aspects, wherein a selectivity to aromatic hydrocarbons is from about 0% to about 95%.

A forty-second aspect, which is the method of any one of the first through the forty-first aspects, wherein at least a portion of $C_{2+}$ hydrocarbons are separated from the product mixture by cryogenic distillation.

A forty-third aspect, which is the method of any one of the first through the forty-second aspects, wherein at least a portion of the unreacted methane is separated from the product mixture to yield recovered methane.

A forty-fourth aspect, which is the method of the forty-third aspect, wherein at least a portion of the recovered methane is recycled to the reactant mixture.

A forty-fifth aspect, which is the method of any one of the first through the forty-fourth aspects, wherein at least a portion of hydrogen is separated from the product mixture by cryogenic distillation.

A forty-sixth aspect, which is the method of any one of the first through the forty-fifth aspects, wherein the secondary reaction zone comprises a catalyst.

A forty-seventh aspect, which is the method of any one of the first through the forty-sixth aspects, wherein both the primary reaction zone and the secondary reaction zone comprise a catalyst.

A forty-eighth aspect, which is a method for producing $C_{2+}$ hydrocarbons and hydrogen comprising (a) introducing a reactant mixture to a reactor, wherein the reactant mixture comprises methane ($CH_4$), wherein the reactor comprises a preheat zone, a catalyzed reaction zone, an uncatalyzed reaction zone, and a quench zone, and wherein the catalyzed reaction zone comprises a catalyst; (b) heating the reactant mixture to a preheating temperature in the preheat zone to yield a heated reactant mixture; (c) contacting at least a portion of the heated reactant mixture with the catalyst in the catalyzed reaction zone to form a catalyst effluent mixture comprising free radicals, $C_{2+}$ hydrocarbons, hydrogen and unreacted methane, wherein the catalyzed reaction zone is characterized by a catalyzed reaction zone temperature and a catalyzed reaction zone residence time, and wherein the catalyzed reaction zone temperature is greater than the preheating temperature; (d) reacting at least a portion of the catalyst effluent mixture in the uncatalyzed reaction zone to form a reaction zone effluent mixture comprising $C_{2+}$ hydrocarbons, hydrogen, free radicals, and unreacted methane, wherein the uncatalyzed reaction zone is characterized by an uncatalyzed reaction zone temperature and an uncatalyzed reaction zone residence time, wherein the uncatalyzed reaction zone residence time is greater than the catalyzed reaction zone residence time; (e) cooling at least a portion of the reaction zone effluent mixture in the quench zone to a quench temperature to yield a product mixture comprising $C_{2+}$ hydrocarbons, hydrogen, and unreacted methane, wherein the quench temperature is lower than the uncatalyzed reaction zone temperature; and (f) recovering at least a portion of the product mixture from the reactor.

A forty-ninth aspect, which is the method of the forty-eighth aspect, wherein the catalyst comprises quartz pieces.

A fiftieth aspect, which is the method of the forty-ninth aspect, wherein the quartz pieces comprise chips, beads, rings, quartz felt, quartz wool, coated quartz, modified quartz, or combinations thereof.

A fifty-first aspect, which is the method of any one of the forty-eighth through the fiftieth aspects, wherein the quartz pieces have a size of from about 10 nm to about 10 cm.

A fifty-second aspect, which is the method of any one of the forty-eighth through the fifty-first aspects, wherein the product mixture comprises benzene.

A fifty-third aspect, which is the method of the fifty-second aspect, wherein at least a portion of benzene is separated from the product mixture.

A fifty-fourth aspect, which is the method of any one of the forty-eighth through the fifty-third aspects, wherein the uncatalyzed reaction zone comprises a chemically reactive material that preferentially reacts with one or more components of the catalyst effluent mixture.

A fifty-fifth aspect, which is the method of any one of the forty-eighth through the fifty-fourth aspects, wherein the uncatalyzed reaction zone comprises a mixture of chemically reactive materials, wherein the mixture preferentially reacts with one or more components of the catalyst effluent mixture.

A fifty-sixth aspect, which is a method for producing $C_{2+}$ hydrocarbons and hydrogen comprising (a) introducing a reactant mixture to a reactor, wherein the reactant mixture comprises methane ($CH_4$), and wherein the reactor comprises a preheat zone, a catalyzed reaction zone, an uncatalyzed reaction zone, and a quench zone, and wherein the catalyzed reaction zone comprises a catalyst; (b) heating the reactant mixture to a preheating temperature in the preheat zone to yield a heated reactant mixture; (c) contacting at least a portion of the heated reactant mixture with the catalyst in the catalyzed reaction zone to form a catalyst effluent mixture comprising free radicals, $C_{2+}$ hydrocarbons, hydrogen and unreacted methane, wherein the catalyzed reaction zone is characterized by a catalyzed reaction zone temperature and a catalyzed reaction zone residence time, and wherein the catalyzed reaction zone temperature is greater than the preheating temperature; (d) reacting at least a portion of the catalyst effluent mixture in the uncatalyzed reaction zone to form a reaction zone effluent mixture comprising $C_{2+}$ hydrocarbons, hydrogen, free radicals, and unreacted methane, wherein the uncatalyzed reaction zone is characterized by an uncatalyzed reaction zone temperature and an uncatalyzed reaction zone residence time, wherein the uncatalyzed reaction zone residence time is greater than the catalyzed reaction zone residence time; (e) cooling at least a portion of the reaction zone effluent mixture in the quench zone to a quench temperature to yield a product mixture comprising $C_{2+}$ hydrocarbons, hydrogen, and unreacted methane, wherein the quench temperature is lower than the uncatalyzed reaction zone temperature; (f) recovering at least a portion of the product mixture from the reactor; and, about concurrently with one or more of steps (a)-(f), (g) introducing hydrogen to one or more of the preheat zone, the catalyzed reaction zone, the uncatalyzed reaction zone, and the quench zone; wherein a selectivity to ethylene is increased when compared to a selectivity to ethylene in an otherwise similar process having steps (a)-(f) and lacking a step (g) of introducing hydrogen; and wherein a coke yield is decreased when compared to a coke yield in an otherwise similar process having steps (a)-(f) and lacking a step (g) of introducing hydrogen.

A fifty-seventh aspect, which is a method for producing $C_{2+}$ hydrocarbons and hydrogen comprising (a) introducing a reactant mixture to a reactor, wherein the reactant mixture comprises methane ($CH_4$), and wherein the reactor comprises a preheat zone, a catalyzed reaction zone, an uncatalyzed reaction zone, and a quench zone, and wherein the catalyzed reaction zone comprises a catalyst; (b) heating the reactant mixture to a preheating temperature in the preheat zone to yield a heated reactant mixture; (c) contacting at least a portion of the heated reactant mixture with the catalyst in the catalyzed reaction zone to form a catalyst effluent mixture comprising free radicals, $C_{2+}$ hydrocarbons, hydrogen and unreacted methane, wherein the catalyzed reaction zone is characterized by a catalyzed reaction zone temperature and a catalyzed reaction zone residence time, and wherein the catalyzed reaction zone temperature is greater than the preheating temperature; (d) reacting at least a portion of the catalyst effluent mixture in the uncatalyzed reaction zone to form a reaction zone effluent mixture comprising $C_{2+}$ hydrocarbons, hydrogen, free radicals, and unreacted methane, wherein the uncatalyzed reaction zone is characterized by an uncatalyzed reaction zone temperature and an uncatalyzed reaction zone residence time, wherein the uncatalyzed reaction zone residence time is greater than the catalyzed reaction zone residence time; (e) cooling at least a portion of the reaction zone effluent mixture in the quench zone to a quench temperature to yield a product mixture comprising $C_{2+}$ hydrocarbons, hydrogen, and unreacted methane, wherein the quench temperature is lower than the uncatalyzed reaction zone temperature; (f) recovering at least a portion of the product mixture from the reactor; and, about concurrently with one or more of steps (a)-(f), (g) introducing a $C_{2+}$ alkane to the uncatalyzed reaction zone and/or the quench zone; wherein an olefin yield is increased when compared to an olefin yield in an otherwise similar process having steps (a)-(f) and lacking a step (g) of introducing a $C_{2+}$ alkane.

A fifty-eighth aspect, which is the method of the fifty-seventh aspect, wherein the $C_{2+}$ alkane comprises ethane, propanes, butanes, light naphtha, liquefied petroleum gas, or combinations thereof.

A fifty-ninth aspect, which is a reactor system for producing $C_{2+}$ hydrocarbons and hydrogen, the reactor system comprising a preheat zone, a primary reaction zone, a secondary reaction zone, and a quench zone; wherein the preheat zone is configured to receive a reactant mixture and to produce a heated reactant mixture, and wherein the preheat zone is characterized by a preheating temperature; wherein the primary reaction zone is configured to receive at least a portion of the heated reactant mixture, to generate free radicals, and to produce a primary effluent mixture, wherein the primary reaction zone comprises a catalyst, wherein the primary reaction zone is characterized by a primary reaction zone temperature and a primary reaction zone residence time, and wherein the primary reaction zone temperature is greater than the preheating temperature; wherein the secondary reaction zone is configured to receive at least a portion of the primary effluent mixture and to produce a secondary effluent mixture, wherein the secondary reaction zone is characterized by a secondary reaction zone temperature and a secondary reaction zone residence time, wherein the primary reaction zone temperature is equal to or greater than the secondary reaction zone temperature, and wherein the secondary reaction zone residence time is greater than the primary reaction zone residence time; and wherein the quench zone is configured to receive at least a portion of the secondary effluent mixture and to produce a product mixture, wherein the quench zone is characterized by a quench temperature, wherein the quench temperature is lower than the secondary reaction zone temperature, and wherein the product mixture comprises $C_{2+}$ hydrocarbons and hydrogen.

A sixtieth aspect, which is the reactor system of the fifty-ninth aspect, wherein each of the preheat zone, the primary reaction zone, the secondary reaction zone, and the quench zone is independently selected from the group consisting of a plug flow reactor and a continuous stirred-tank reactor.

A sixty-first aspect, which is the reactor system of any one of the fifty-ninth and the sixtieth aspects, wherein the primary reaction zone comprises a catalyst bed, wherein the catalyst bed comprises catalyst particles, a monolithic catalyst, a honeycomb catalyst, a honeycombed wall filter design catalyst, a monolithic foam of ceramic construction, a monolithic foam of metal construction, or combinations thereof.

A sixty-second aspect, which is the reactor system of any one of the fifty-ninth through the sixty-first aspects, wherein a diameter of the quench zone is greater than a diameter of the secondary reaction zone.

A sixty-third aspect, which is the reactor system of any one of the fifty-ninth through the sixty-second aspects, wherein each of the primary reaction zone, the secondary reaction zone, and the quench zone comprise one or more injection quills, one or more injection nozzles, or combinations thereof.

A sixty-fourth aspect, which is the reactor system of any one of the fifty-ninth through the sixty-third aspects, wherein the secondary reaction zone comprises a high temperature resistance membrane to separate and recover at least a portion of olefins or at least a portion of hydrogen from the secondary reaction zone.

A sixty-fifth aspect, which is the reactor system of any one of the fifty-ninth through the sixty-fourth aspects further comprising a heat exchanger configured to provide thermal contact between a reactant mixture and a product mixture, thereby increasing a temperature of the reactant mixture.

A sixty-sixth aspect, which is the reactor system of the sixty-fifth aspect, wherein the reactor system comprises an "U" shaped reactor, and wherein the heat exchanger provides thermal contact between the reactant mixture and the product mixture for the same reactor.

A sixty-seventh aspect, which is the reactor system of the sixty-fifth aspect, wherein the heat exchanger provides thermal contact between the product mixture recovered from the quench zone of a first reactor and the reactant mixture that is introduced to the preheat zone of a second reactor.

A sixty-eighth aspect, which is the reactor system of the fifty-ninth aspect, wherein the preheat zone, the primary reaction zone, the secondary reaction zone, and the quench zone are not separated by physical structure into discrete zones and thus one or more of said zones may overlap at a transitory boundary or area between said zones (e.g., along the length of a cylindrical or tubular reactor).

While aspects and embodiments of the disclosure have been shown and described, modifications thereof can be made without departing from the spirit and teachings of the invention. The aspects, embodiments and examples described herein are exemplary only, and are not intended to be limiting. Many variations and modifications of the invention disclosed herein are possible and are within the scope of the invention.

Accordingly, the scope of protection is not limited by the description set out above but is only limited by the claims which follow, that scope including all equivalents of the subject matter of the claims Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A method for producing $C_{2+}$ hydrocarbons and hydrogen comprising:
   (a) introducing a reactant mixture to a reactor, wherein the reactant mixture comprises methane ($CH_4$) and excludes oxygen, and wherein the reactor comprises a preheat zone, a primary reaction zone, a secondary reaction zone, and a quench zone;
   (b) heating the reactant mixture to a preheating temperature in the preheat zone to yield a heated reactant mixture;
   (c) generating free radicals by plasma sources, by a supersonic hot gas stream, by photo-dissociation under irradiation with UV radiation, catalytically, or a combination thereof, in at least a portion of the heated reactant mixture in the primary reaction zone to form a primary effluent mixture comprising free radicals, $C_{2+}$ hydrocarbons, hydrogen, and unreacted methane;
   (d) reacting at least a portion of the primary effluent mixture in the secondary reaction zone to form a secondary effluent mixture comprising $C_{2+}$ hydrocarbons, hydrogen, free radicals, and unreacted methane, wherein the secondary reaction zone is characterized by a secondary reaction zone temperature, wherein the secondary reaction zone temperature is greater than the preheating temperature, wherein an amount of unreacted methane in the primary effluent mixture is greater than an amount of unreacted methane in the secondary effluent mixture, and wherein an amount of free radicals in the primary effluent mixture is greater than an amount of free radicals in the secondary effluent mixture;
   (e) cooling at least a portion of the secondary effluent mixture in the quench zone to a quench temperature to yield a product mixture comprising $C_{2+}$ hydrocarbons, hydrogen and unreacted methane, wherein the quench temperature is lower than the secondary reaction zone temperature; and
   (f) recovering at least a portion of the product mixture from the reactor.

2. The method of claim 1, wherein the reactant mixture further comprises a diluent, and wherein the diluent comprises nitrogen, argon, neon, helium, krypton, xenon, carbon monoxide, carbon dioxide, hydrogen, steam, ethane, propane, butanes, unsaturated hydrocarbons, or combinations thereof.

3. The method of claim 1, wherein the reactant mixture further comprises a promoter, and wherein the promoter comprises alkanes, alkenes, naphthalene, functionalized hydrocarbons, radical initiators, alcohols, ethers, or combinations thereof.

4. The method of claim 1, wherein the reactor comprise a tubular reactor, a continuous flow reactor, a riser reactor, a reformer reactor, a fixed bed reactor, a shock tube reactor, a multi-tubular reactor, a membrane reactor, a dual flow reactor, a gauze reactor, a fluidized bed reactor, a moving bed reactor, a continuous stirred-tank reactor, a plug flow reactor, a microchannel reactor, a modular reactor, a modular microchannel reactor, a honeycombed monolithic reactor, a honeycombed wall filter monolithic reactor, or combinations thereof.

5. The method of claim 1, wherein the preheating temperature is from about 200° C. to about 800° C.

6. The method of claim 1, wherein the primary reaction zone is characterized by a primary reaction zone temperature of from about 700° C. to about 1,300° C.

7. The method of claim 1, wherein the primary reaction zone temperature is equal to or greater than the secondary reaction zone temperature.

8. The method of claim 1, wherein the primary reaction zone is a catalyzed reaction zone comprising a catalyst.

9. The method of claim 8, wherein the catalyzed reaction zone is characterized by a catalyzed reaction zone residence time of from about 0.01 ms to about 3,500 ms.

10. The method of claim 8, wherein the catalyst comprises a catalytically active metal, wherein the catalytically active metal comprises Li, Na, K, Mg, Al, B, Ca, Sr, Ba, Y, La, Ti, Zr, Ce, V, Nb, Ta, Cr, Mo, W, Re, Fe, Ru, Co, Rh, Ir, Ni, Pd, Pt, Cu, Zn, Ge, In, Sn, Pb, Bi, Mn, Pr, Nd, Pm, Sm, Eu, Gd, Tb, Dy, Ho, Er, Tm, Yb, alloys thereof, intermetallic alloys thereof, oxides thereof, carbides thereof, nitrides thereof, silicides thereof, silicates thereof, germanides thereof, germanates thereof, titanates thereof, zirconates thereof, phosphides thereof, or combinations thereof.

11. The method of claim 10, wherein the catalytically active metals are doped in a lattice of amorphous-molten-state materials made from one or more of B, Al, Si, Ti, Zr, and Ge bonded with one or more of C, N and O.

12. The method of claim 8, wherein the catalyst further excludes a catalytically active metal, and wherein the catalyst comprises a silicon based material; Si bonded with one or more of C, N and O; silica; quartz, α-quartz, β-quartz; cristobalite; tridymite, α-tridymite, β-tridymite; silica glass; or combinations thereof.

13. The method of claim 1, wherein the secondary reaction zone temperature is from about 700° C. to about 1,300° C.

14. The method of claim 1, wherein the quench temperature is from about room temperature to about 700° C.

15. The method of claim 1, wherein the quench zone is cooled by external heat exchange, removing supplied heat, expansive cooling, converting thermal energy into work, dilution, endothermic reactions, addition of $C_{2+}$ alkanes, or combinations thereof.

16. A method for producing $C_{2+}$ hydrocarbons and hydrogen comprising:
(a) introducing a reactant mixture to a reactor, wherein the reactant mixture comprises methane ($CH_4$) and excludes oxygen, and wherein the reactor comprises a preheat zone, a catalyzed reaction zone, an uncatalyzed reaction zone, and a quench zone, and wherein the catalyzed reaction zone comprises a catalyst;
(b) heating the reactant mixture to a preheating temperature in the preheat zone to yield a heated reactant mixture;
(c) contacting at least a portion of the heated reactant mixture with the catalyst in the catalyzed reaction zone to form a catalyst effluent mixture comprising free radicals, $C_{2+}$ hydrocarbons, hydrogen and unreacted methane, wherein the catalyzed reaction zone is characterized by a catalyzed reaction zone temperature and a catalyzed reaction zone residence time, and wherein the catalyzed reaction zone temperature is greater than the preheating temperature;
(d) reacting at least a portion of the catalyst effluent mixture in the uncatalyzed reaction zone to form a reaction zone effluent mixture comprising $C_{2+}$ hydrocarbons, hydrogen, free radicals, and unreacted methane, wherein the uncatalyzed reaction zone is characterized by an uncatalyzed reaction zone temperature and an uncatalyzed reaction zone residence time, wherein the uncatalyzed reaction zone residence time is greater than the catalyzed reaction zone residence time;
(e) cooling at least a portion of the reaction zone effluent mixture in the quench zone to a quench temperature to yield a product mixture comprising $C_{2+}$ hydrocarbons, hydrogen, and unreacted methane, wherein the quench temperature is lower than the uncatalyzed reaction zone temperature;
(f) recovering at least a portion of the product mixture from the reactor; and
(g) introducing hydrogen to one or more of the preheat zone, the catalyzed reaction zone, the uncatalyzed reaction zone, and the quench zone;
wherein a selectivity to ethylene is increased when compared to a selectivity to ethylene in an otherwise corresponding process that lacks a step (g) of introducing hydrogen; and wherein a coke yield is decreased when compared to a coke yield in an otherwise corresponding process that lacks a step (g) of introducing hydrogen.

17. A method for producing $C_{2+}$ hydrocarbons and hydrogen comprising:
(a) introducing a reactant mixture to a reactor, wherein the reactant mixture comprises methane ($CH_4$) and excludes oxygen, and wherein the reactor comprises a preheat zone, a catalyzed reaction zone, an uncatalyzed reaction zone, and a quench zone, and wherein the catalyzed reaction zone comprises a catalyst;
(b) heating the reactant mixture to a preheating temperature in the preheat zone to yield a heated reactant mixture;
(c) contacting at least a portion of the heated reactant mixture with the catalyst in the catalyzed reaction zone to form a catalyst effluent mixture comprising free radicals, $C_{2+}$ hydrocarbons, hydrogen and unreacted methane, wherein the catalyzed reaction zone is characterized by a catalyzed reaction zone temperature and a catalyzed reaction zone residence time, and wherein the catalyzed reaction zone temperature is greater than the preheating temperature;
(d) reacting at least a portion of the catalyst effluent mixture in the uncatalyzed reaction zone to form a reaction zone effluent mixture comprising $C_{2+}$ hydrocarbons, hydrogen, free radicals, and unreacted methane, wherein the uncatalyzed reaction zone is characterized by an uncatalyzed reaction zone temperature and an uncatalyzed reaction zone residence time, wherein the uncatalyzed reaction zone residence time is greater than the catalyzed reaction zone residence time;
(e) cooling at least a portion of the reaction zone effluent mixture in the quench zone to a quench temperature to yield a product mixture comprising $C_{2+}$ hydrocarbons, hydrogen, and unreacted methane, wherein the quench temperature is lower than the uncatalyzed reaction zone temperature;
(f) recovering at least a portion of the product mixture from the reactor; and
(g) introducing a $C_{2+}$ alkane to the uncatalyzed reaction zone and/or the quench zone;
wherein an olefin yield is increased when compared to an olefin yield in an otherwise corresponding process that lacks a step (g) of introducing a $C_{2+}$ alkane.

18. The method of claim 17, wherein the $C_{2+}$ alkane comprises ethane, propane, butanes, light naphtha, liquefied petroleum gas, or combinations thereof.

* * * * *